US006214794B1

(12) United States Patent
Beachy et al.

(10) Patent No.: US 6,214,794 B1
(45) Date of Patent: *Apr. 10, 2001

(54) METHOD OF USING HEDGEHOG POLYPEPTIDES TO REGULATE NEURONAL CELL GROWTH

(75) Inventors: Philip A. Beachy, Baltimore, MD (US); Randall T. Moon, Seattle, WA (US); Jeffrey A. Porter, Baltimore, MD (US)

(73) Assignees: The Johns Hopkins University School of Medicine, Baltimore, MD (US); University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/729,743

(22) Filed: Oct. 7, 1996

Related U.S. Application Data

(63) Continuation-in-part of application No. 08/567,357, filed on Dec. 4, 1995, which is a continuation-in-part of application No. 08/349,498, filed on Dec. 2, 1994.

(51) Int. Cl.[7] .......................... C07K 14/475; A61K 38/18
(52) U.S. Cl. ................................ 514/12; 514/2; 530/300; 530/350
(58) Field of Search .................................. 530/300, 350; 435/7.1, 7.2, 7.21, 7.8; 514/2, 12

(56) References Cited

U.S. PATENT DOCUMENTS

| | | | |
|---|---|---|---|
| 5,143,830 | 9/1992 | Holland et al. | 435/69.7 |
| 5,789,543 | 8/1998 | Ingham et al. | 530/350 |
| 5,844,079 | 12/1998 | Ingham et al. | 530/350 |

OTHER PUBLICATIONS

Ngo et al (1994) in: The Protein Folding Problem and Tertiary Structure Prediction. Merz et al. (eds) Birkhauser, Boston pp. 433, 492–495.*
Echelard et al. (1993) Cell 75:1417–1430.*
Placzck et al. (1993) Development 117:205–218.*
Hamerschnt et al. (1997) Trends Genet. 13:14–15.*

Lee et al., "Autoproteolysis in hedgehog Protein Biogenesis", *Science*, 266:1528–1537, Dec. 2, 1994.
Tabata and Kornberg, "Hedgehog is a Signaling Protein with a Key Role in Patterning Drosphila Imaginal Discs", *Cell*, 76:89–102, Jan. 14, 1994.
Krauss et al., "A Functionally Conserved Homolog of the Drosophila Segment Polarity Gene hh Is Expressed in Tissues with Polarizing Activity in Zebrafish Embryos", *Cell*, 75:1431–1444, Dec. 31, 1993.
Ganong, William F., Review of Medical Physiology, Norwalk, Connecticut: Appleton and Lange, 1995, pp. 273 and 438.
Mohler et al., "Molecular organization and embryonic expression of the hedgehog gene involved in cell–cell communication in segmental patterning of Drosphila, " *Development*, 1992, vol. 115, pp. 957–971.
Lee et al., "Secretion and localized transcription suggest a role in positional signalling for products of the segmentation gene hedgehog", *Cell*, Oct. 2, 1992, vol. 71, pp. 33–50.
Clarke et al., "Cellular lipid binding proteins: expression, function and nutritional regulation," *FESEB J.*, Nov. 1989, vol. 3, pp. 2480–2487.
Ingham, P.W., "Signalling by hedgehog family proteins in Drosphila and vertebrate development", *Cur. Opin. Gen. Dev.*, 1995, vol. 5, pp. 492–498.
Reeck et al., "Homology" in proteins and nucleic acids: a terminology muddle and a way out of it, Cell, 50:667 (Aug. 1987).*
Hynes et al., Induction of midbrain dopaminergic neurons by Sonic hedgehog, Neuron, 15: 35–44, 1995.*

\* cited by examiner

*Primary Examiner*—Lorraine Spector
*Assistant Examiner*—Claire M. Kaufman
(74) *Attorney, Agent, or Firm*—Gray Cary Ware & Freidenrich LLP; Lisa A. Haile, Ph.D.

(57) ABSTRACT

The present invention provides two novel polypeptides, referred to as the "N" and "C" fragments of hedgehog, or N-terminal and C-terminal fragments, respectively, which are derived after specific cleavage at a Gly↓Cys Phe site recognized by the autoproteolytic domain in the native protein. Methods of identifying compositions which affect hedgehog activity based on inhibition of cholesterol modification of hedgehog protein are described. Also provided are methods of use of the N and C fragments.

14 Claims, 34 Drawing Sheets

|  | 1 | 2 | 3 | 4 | 5 | 6 | 7 |  |
|---|---|---|---|---|---|---|---|---|
| D. mel. hh | L | T | V | T | P | A | H | SEQ ID NO:23 |
| D. hydei hh | L | T | V | T | P | A | H | SEQ ID NO:23 |
| C-Shh | L | L | L | T | A | A | H | SEQ ID NO:19 |
| M-Shh/Hhg-1 | L | L | L | T | A | A | H | SEQ ID NO:20 |
| R vhh-1 | L | L | L | T | A | A | H | SEQ ID NO:24 |
| Z-Shh/Zf vhh-1 | I | T | L | T | A | A | H | SEQ ID NO:18 |
| twhh | L | T | L | T | A | A | H | SEQ ID NO:17 |
| M-Dhh | L | L | L | T | P | W | H | SEQ ID NO:25 |
| M-Ihh | L | A | L | T | P | A | H | SEQ ID NO:26 |

*FIG. 2A*

| CHT | W | V | V | T | A | A | H | SEQ ID NO:27 |
|---|---|---|---|---|---|---|---|---|
| TRP | W | V | V | S | A | A | H | SEQ ID NO:28 |
| ELA | W | V | M | T | A | A | H | SEQ ID NO:29 |
| UKH | W | V | I | S | A | T | H | SEQ ID NO:30 |
| C1R | W | I | L | T | A | A | H | SEQ ID NO:31 |
| C1S | W | V | L | T | A | A | H | SEQ ID NO:32 |
| MCP | F | V | L | T | A | A | H | SEQ ID NO:33 |
| FAX | Y | V | L | T | A | A | H | SEQ ID NO:34 |
| TPA | W | I | L | S | A | A | H | SEQ ID NO:35 |

*FIG. 2B*

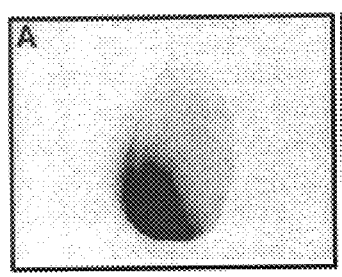 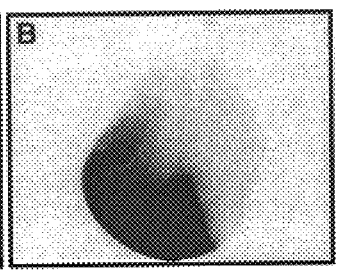 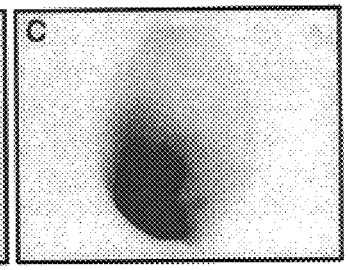
FIG. 7A            FIG. 7B            FIG. 7C
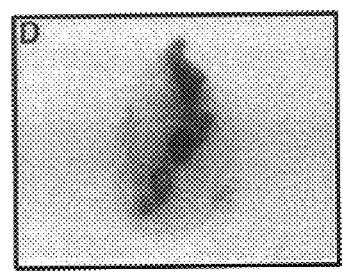 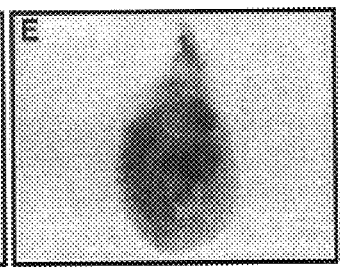 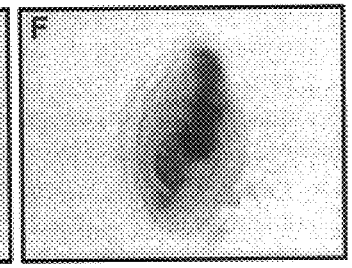
FIG. 7D            FIG. 7E            FIG. 7F
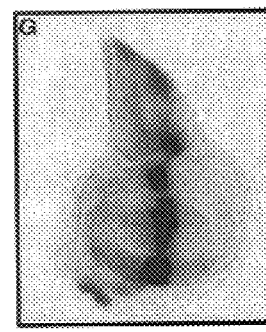 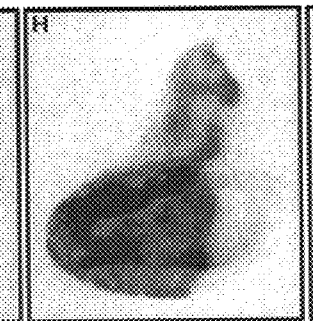 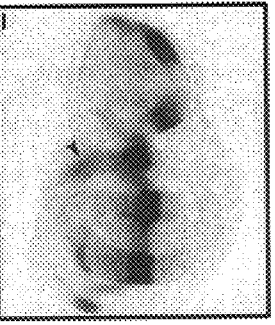
FIG. 7G            FIG. 7H            FIG. 7I
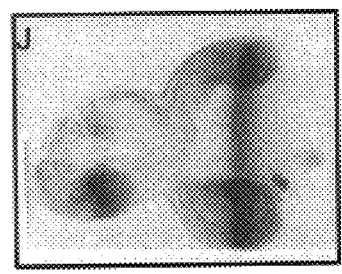 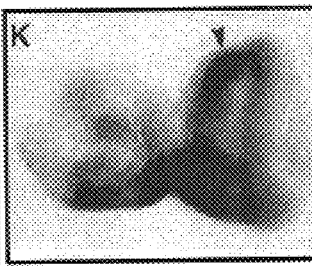 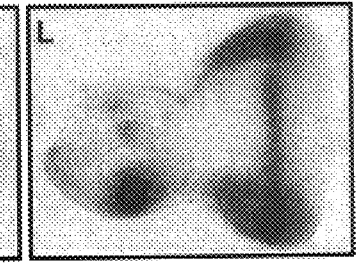
Fig. 7J            Fig. 7K            FIG. 7L
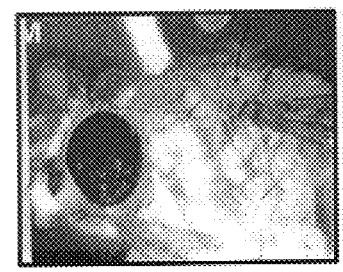 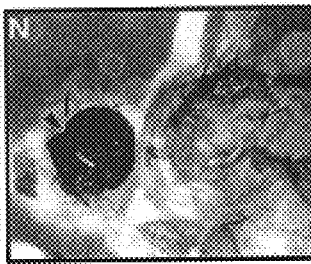 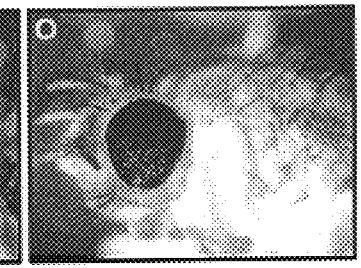
FIG. 7M            FIG. 7N            FIG. 7O

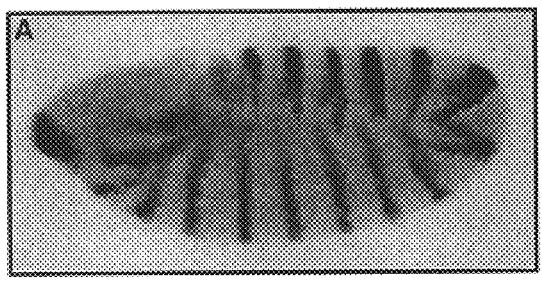
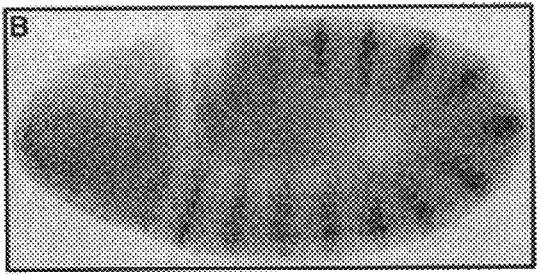
FIG. 9A  FIG. 9B
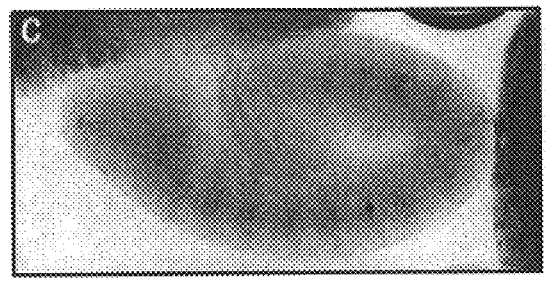
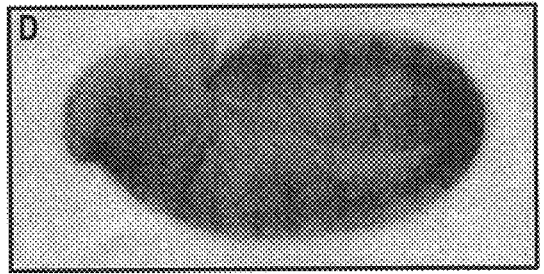
FIG. 9C  FIG. 9D

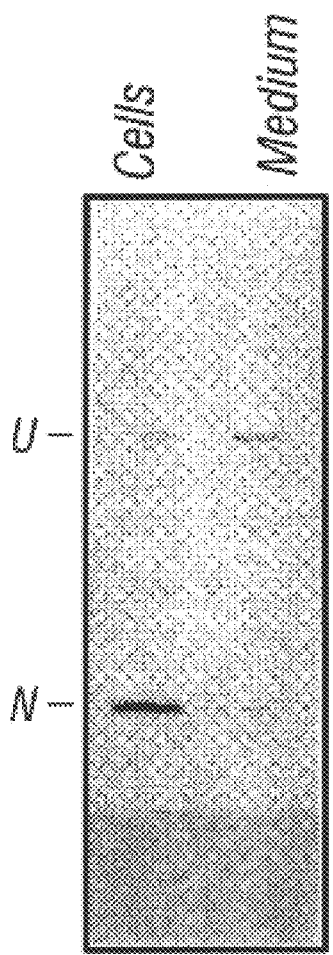
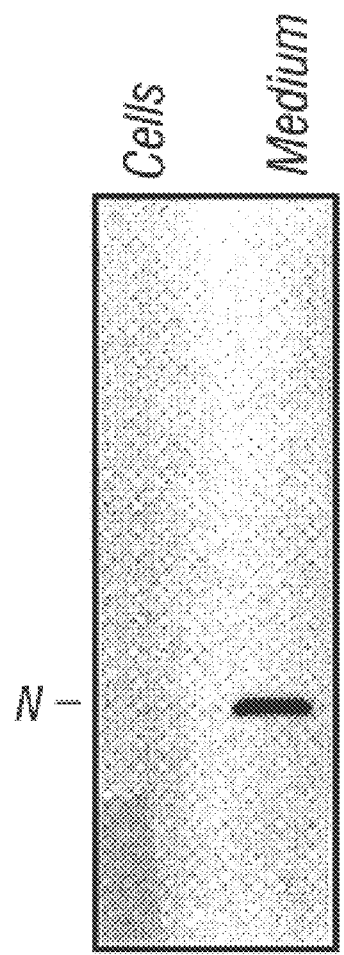
*FIG. 10C*  *FIG. 10D* human hh B -> 1-phase Translation Sonic HHG1
(SEQ ID NO:1) DNA sequence 144 b.p. GTGAAACTGCGG ... CTGGGGGTGGAG linear

```
1/1                                                                 31/11
GTG AAA CTG CGG GTG CTG GAG GGC TGG GAC GAA GAT GGC CAC TCA CAG GAG TCT CTG
Val Lys Leu Arg Val Leu Glu Gly Trp Asp Glu Asp Gly His Ser Gln Glu Ser Leu
61/21                                                               91/31
CAC TAC GAG GGC CGC GCA GTG GAC ATC ACC ACG TCT GAC CGC GAC AGC AAG TAC GGC
His Tyr Glu Gly Arg Ala Val Asp Ile Thr Thr Ser Asp Arg Asp Ser Lys Tyr Gly
121/41
ATG CTG GCC CGC CTG GCG GTG GAG
Met Leu Ala Arg Leu Ala Val Glu
```

FIG. 11A human hh A -> 1-phase Translation HHG2 (probably Desert or Indian)
(SEQ ID NO:2) DNA sequence 144 b.p. GTGAAGGGCTGCGG ... TTGGCAGTGGAG linear

```
1/1                                                                 31/11
GTG AAG CTG CGG GTG ACC GAG GGC TGG GAC GAG GAC GGC CAC CAC TCA GAG GAG TCC CTG
Val Lys Leu Arg Val Thr Glu Gly Trp Asp Glu Asp Gly His His Ser Glu Glu Ser Leu
61/21                                                               91/31
CAT TAT GAG GGC CGC GCG GTG GAC ATC ACC ACA TCA GAC CGC GAC CGC AAT AAG TAT GGA
His Tyr Glu Gly Arg Ala Val Asp Ile Thr Thr Ser Asp Arg Asp Arg Ser Lys Tyr Gly
121/41
CTG CTG GCG CGC TTG GCA GTG GAG
Met Leu Ala Arg Leu Ala Val Glu
```

FIG. 11B

Cleavage Site Sequence
...SHVHG CFTPE...
253    262

| | | |
|---|---|---|
| D. melanogaster hh | ISSHVHGCFTPEST | SEQ ID NO.3 |
| D. hydei hh | SISHMHGCFTPEST | SEQ ID NO.4 |
| m-sonic hh | VAAKSGGCFPGSAT | SEQ ID NO.5 |
| r-sonic hh | VAAKSDGCFPGSAT | SEQ ID NO.6 |
| c-sonic hh | VAAKSGGCFPGSAL | SEQ ID NO.7 |
| z-sonic hh | VAAKSGGCFPGSGT | SEQ ID NO.8 |
| z-twhh | VAAKSGGCFPAGAR | SEQ ID NO.9 |
| x-sonic hh | VAAKTGGCFPAGAQ | SEQ ID NO.10 |
| m-indian hh | VAAKTGGCFPGEAL | SEQ ID NO.11 |
| x-bhh | LGVRSGGCFPGTAM | SEQ ID NO.12 |
| x-hh4 | LGVRSGGCFPGTAM | SEQ ID NO.37 |
| x-hh3 | LGVRSGGCFPGTAM | |
| m-desert hh | LAVRAGGCFPGNAT | SEQ ID NO.13 |

*FIG. 12C*

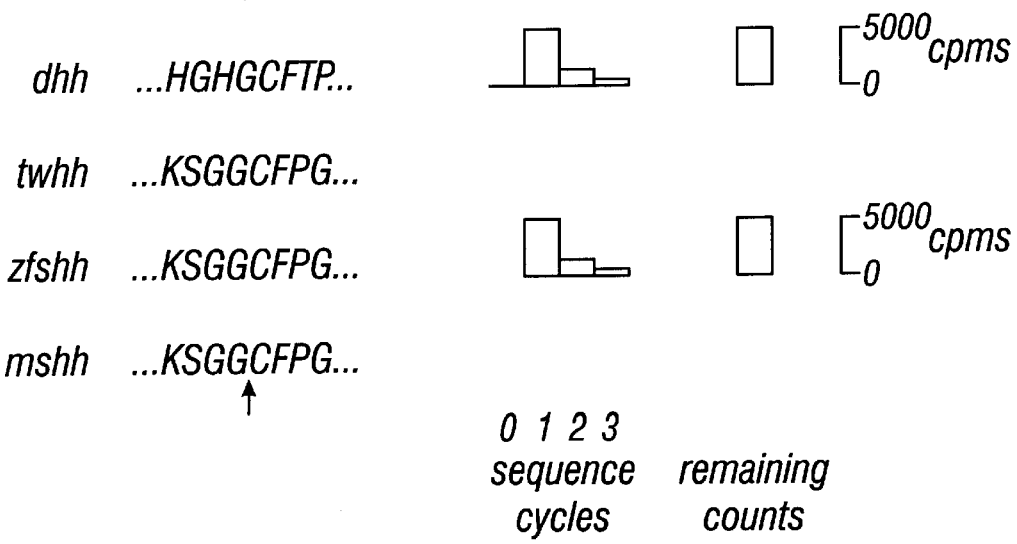

Edman Degradation of In vitro translation Products

```
Zebrafish twhh   VKLRVTEGWDEDGHHLEESLHYEGRAVDITTSDRDKSKYG
hh[zfB]          .R............S...................RN..A
hh[zfC]          .R.....A......PPG.................TK...
hh[zfD]          ..............N.F.D...............RN...
Zebrafish shh    ...............F........................
```

```
                                        ↓
Zebrafish twhh   MDVRLHLKQFALLCFISLLLTPCGLACGPGRGYGKRRHPK
Zebrafish shh    M--RL-LTRVLLVSLLTLSLVVSGLACGPGRGYGRRHPK
Chicken   shh    MVEMLLLTRILLVGFICALLVSSGLTCGPGRGIGKRRHPK
Mouse     shh    M--ILLLARCFLVILASSLLVCPGLACGPGRGFGKRRHPK Zebrafish twhh   FKELTPNYNPDIIFKDEENTNADRLMTKRCKDKLNSLAIS
Zebrafish shh    FKELTPNYNPDIIFKDEENTGADRLMTQRCKDKLNSLAIS
Chicken   shh    FKELTPNYNPDIIFKDEENTGADRLMTQRCKDKLNALAIS
Mouse     shh    FKELTPNYNPDIIFKDEENTGADRLMTQRCKDKLNALAIS Zebrafish twhh   ITTSDRDKSKYGMLSRLAVEAGFDWVYYESKAHIHCSVKA
Zebrafish shh    ITTSDRDKSKYGTLSRLAVEAGFDWVYYESKAHIHCSVKA
Chicken   shh    ITTSDRDRSKYGMLARLAVEAGFDWVYYESKAHIHCSVKA
Mouse     shh    ITTSDRDRSKYGMLARLAVEAGFDWVYYESKAHIHCSVKA Zebrafish twhh   RVLAADEKGNVLISDFIMFIDHDPTTRRQFIVIETSEPFT
Zebrafish shh    KVLAADSAGNLVFSDFIMFIDRDSTTRRVFYVIETQEPVE
Chicken   shh    RVLAADADGRLLYSDFLTFLDRMDSSRKLFYVIETRQPRA
Mouse     shh    RVLAADDQGRLLYSDFLTFLDRDEGAKKVFYVIETLEPRE Zebrafish twhh   KPGDIVLVWEDICESLKSV--TVKRI-YTEEHEGSHAPVT
Zebrafish shh    RAGQKVMV-VDDSGQLKSV--IVQRI-YTEEQRGSHAPVT
Chicken   shh    KPGQRVYVLGEGGQQLLPA--SVHSVSLREEASGAYAPLT
Mouse     shh    RPGQRVYVVAERGGDRRLLPAAVHSVTLREEFAGAYAPLT Zebrafish twhh   KLMIWLFP--------ARESNVNFQED--------GIHWY
Zebrafish shh    YVSSFLFP-----QNSSSRSNATLQQE--------GVHWY
Chicken   shh    GLLAALCP-----D--GAIPTAATTTT--------GIHWY
Mouse     shh    ALLAALAPARTDGGGGSIPAAQSATEARGAEPTAGIHWY
```

| | | | | | |
|---|---|---|---|---|---|
| MLSRLAVE | Z-twhh | | | | |
| ..A..... | Z-twhh | 100 | Z-shh | | |
| L.AQ.... | Z-shh | 73 | 100 | C-Shh | |
| ..A..... | C-Shh | 69 | 68 | 100 | M-Shh |
| T....... | M-Shh | 66 | 68 | 82 | 100 |

| | |
|---|---|
| KLTPLAYKQFIPNVAEKTLGASGKYEGKITRNSER | 75 |
| KLTPLAYKQFIPNVAEKTLGASGRYEGKITRNSER | 72 |
| KLTPLAYKQFIPNVAEKTLGASGRYEGKITRNSER | 75 |
| KLTPLAYKQFIPNVAEKTLGASGRYEGKITRNSER | 73 |
| | |
| VMNHWPGVKLRVTEGWDEDGHHLEESLHYEGRAVD | 150 |
| VMNHWPGVKLRVTEGWDEDGHHFEESLHYEGRAVD | 147 |
| VMNQWPGVKLRVTEGWDEDGHHSEESLHYEGRAVD | 150 |
| VMNQWPGVRLRVTEGWDEDGHHSEESLHYEGRAVD | 148 |
| | |
| ENSVAAKSGGCFPGSGIVILGDGIRKPIKDLKVGD | 225 |
| ENSVAAKSGGCFPGSALVSLQDGGQKAVKDLNPGD | 222 |
| ENSVAAKSGGCFPGSATVHLEHGGIKLVKDLSPGD | 225 |
| ENSVAAKSGGCFPGSATVHLEQGGIKLVKDLRPGD | 223 |
| | |
| KLTILTAAHLVFVG-NSSAAS--GITAT---FASNV | 294 |
| KTTILTAAHLLFVL-DNSTEDLHIMTAA---YASSV | 293 |
| RLLLTAAHLLFVAPQHNQSEATGSTSGQALFASNV | 300 |
| RLLLTAAHLLFVAPHNDSGPTPGPSAL---FASRV | 295 |
| | |
| AHGTTIVDQVLASCYAVIENHKWAHWAFAPVRLCH | 366 |
| AHGTIVVDRILASCYAVIEDQGLAHLAFAPARLYY | 364 |
| AQGTILINRVLASCYAVIEEHSWAHWAFAPFRLAQ | 373 |
| AHGTILINRVLASCYAVIEEHSWAHRAFAPFRLAH | 370 |
| | |
| SNMLFHIGSWLLDRDSFHPLGI-LHLS | 416 |
| SRLLYQMGIWLLDSNMLHPLGMSVNSS | 418 |
| SRLLYRIGSWVLDGDALHPLGMVAPAS | 425 |
| SQLLYHIGIWLLDSEIMHPLGMAVKSS | 437 |

FIG. 13B

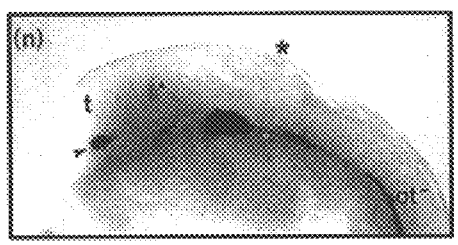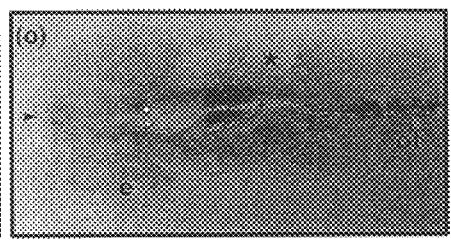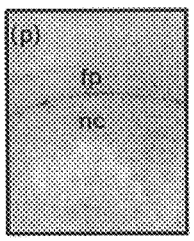
FIG. 14N   FIG. 14O   FIG. 14P
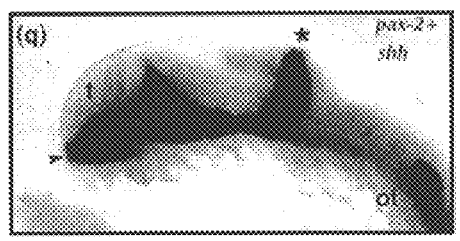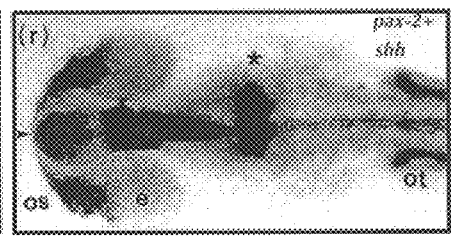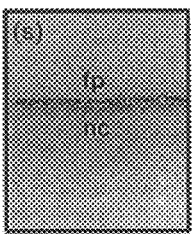
FIG. 14Q   FIG. 14R   FIG. 14S

| b-gal-injected | twhh-injected | shh or twhh-injected |
|---|---|---|
|  |  |  |
| FIG. 15A | FIG. 15B | FIG. 15C |
|  | 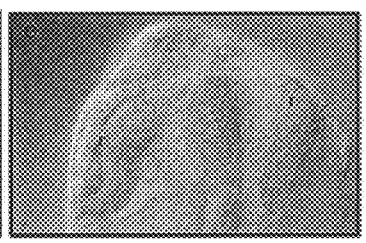 | 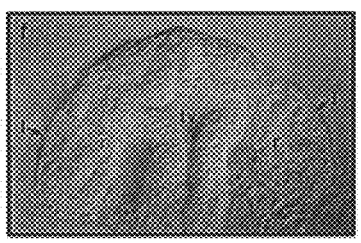 |
| FIG. 15D | FIG. 15E | FIG. 15F |
|  | 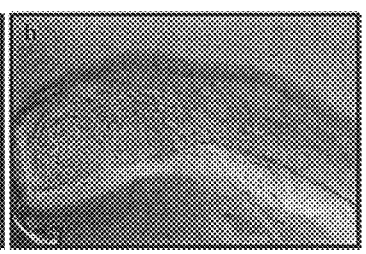 | 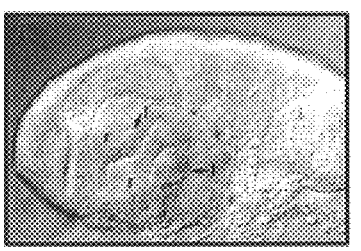 |
| FIG. 15G | FIG. 15H | FIG. 15I |

| Table 1. Effects of ectopic expression of ssh, twhh, twhh-N, twhh-$U_{HA}$ and lacZ on zebrafish embryonic development. | | | | | |
|---|---|---|---|---|---|
| Injected mRNA | shh | twhh | twhh-N | twhh-$U_{HA}$ | lac-Z |
| 12.5 h | | | | | |
| Ectopic pax-2 in eye | 89% (35) | 82% (22) | 92% (26) | 90% (30) | 0% (31) |
| 22h | | | | | |
| Ectopic pax-2 in eye | 22% (54) | 62% (50) | 76% (42) | 21% (39) | 0% (34) |
| Reduced pax-6 in eye | 20% | 68% | 54% | 1% | 0% |
| Reduced pax-6 in ventral forebrain | 0% | 43% | 79% | 0% | 0% |
| Reduced pax-6 in hindbrain | 0% (35) | 18% (40) | 61% (28) | 0% (68) | 0% (14) |
| 28h | | | | | |
| Lens absent | 16% | 86% | 100% | 9% | 0% |
| Lens smaller | 48% | 9% | 0% | 36% | 0% |
| Reduced eye pigment | 80% | 91% | 100% | 64% | 0% |
| No midbrain-hindbrain constriction | 48% (25) | 77% (44) | 100% (16) | 22% (45) | 3% (37) |

FIG. 16

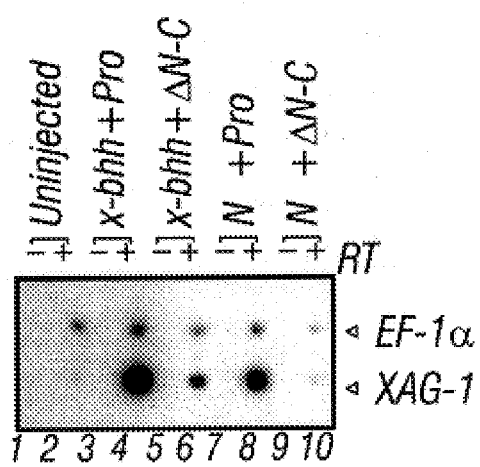
FIG. 21
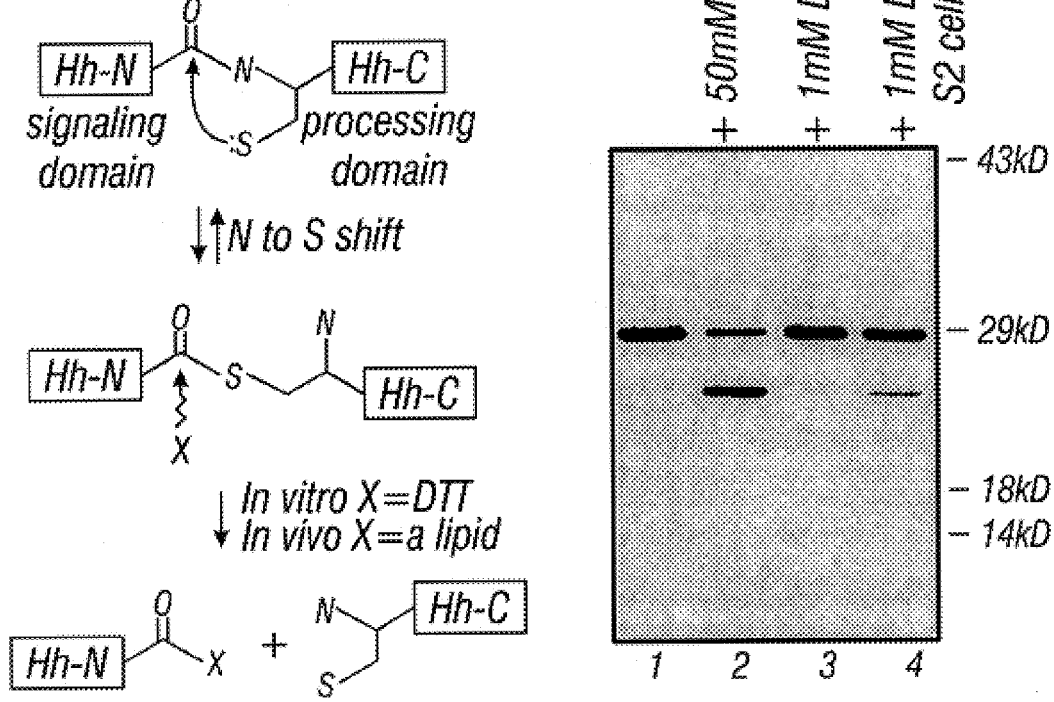
FIG. 22A  FIG. 22B

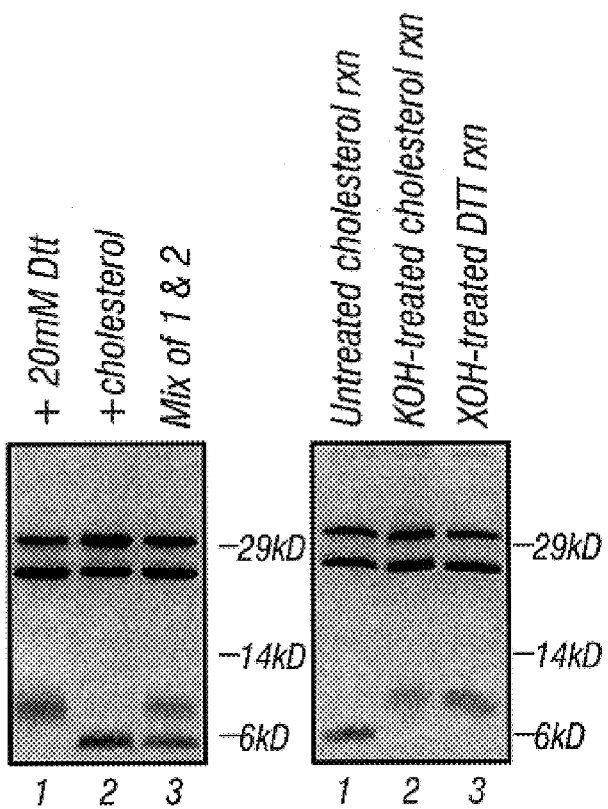
FIG. 24A  FIG. 24B
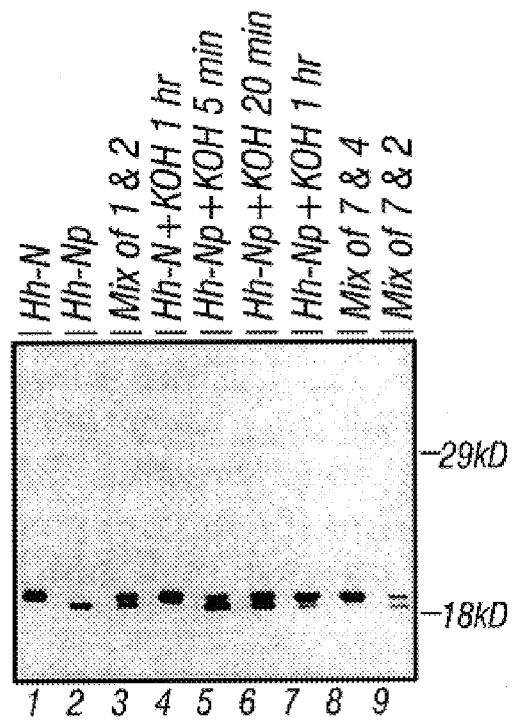
FIG. 24C

METHOD OF USING HEDGEHOG POLYPEPTIDES TO REGULATE NEURONAL CELL GROWTH

This application is a continuation-in-part of U.S. patent application Ser. No. 08/567,357 filed Dec. 4, 1995 which is a continuation-in-part of application Ser. No. 08/349,498 filed on Dec. 2, 1994.

BACKGROUND OF THE INVENTION

1. Field of the Invention

This invention relates generally to the field of protein processing and protein signalling pathways and specifically to two novel proteins having distinct activities, which are derived from a common hedgehog protein precursor.

2. Description of the Related Art

Embryologists have long performed experimental manipulations that reveal the striking abilities of certain structures in vertebrate embryos to impose pattern upon surrounding tissues. Speculation on the mechanisms underlying these patterning effects usually centers on the secretion of signaling molecule that elicits an appropriate response from the tissues begin patterned. More recent work aimed at the identification of such signaling molecules implicates secreted proteins encoded by individual members of a small number of gene families. One such family of proteins which may have an influential effect upon patterning activities are those proteins encoded by the hedgehog gene family.

The hedgehog (hh) gene was initially identified based on its requirement for normal segmental patterning in Drosophila (Nüsslein-Volhard, C. & Wieschaus, E, *Nature* 287:795–801, 1980). Its functions include local signaling to coordinate the identities of adjacent cells within early embryonic segments (Hooper, J. E., & Scott, M. P. *Early Embryonic Development of Animals*, pp.1–48, 1992) and a later function in cuticle patterning that extends across many cell diameters (Heernskerk, J. & DiNardo, S., *Cell*, 76:449–460, 1994). The hh gene also functions in the patterning of imaginal precursors of adult structures, including the appendages and the eye (Mohler, *J. Genetics*, 120:1061–1072, 1988; Ma, et al., *Cell*, 75:927–938, 1993; Heberlein, et al, *Cell*, 75:913–926, 1993; Tabata, T. & Kornberg, T. D., *Cell*, 76:89–102, 1992; Basler, K. & Struhl, G., *Nature*, 368:208–214,1994). Genetic and molecular evidence indicates that hedgehog proteins are secreted and function in extracellular signaling (Mohler, J., supra; Lee, et al, *Cell*, 71:33–50, 1992; Taylor, et al., *Mech. Dev*, 42:89–96, 1993).

In vertebrates activities encoded by hh homologues have been implicated in anterior/posterior patterning of the limb (Riddle, et al., *Cell*, 75:1401–1416, 1993; Chang, et al., *Development*, 120:3339, 1994), and in dorsal/ventral patterning of the neural tube (Echelard, et al., *Cell*, 75:1417–1430, 1993; Krauss, et al., *Cell*, 75:1431–1444, 1993; Roelink, et al., *Cell*, 76:761–775, 1994).

The vertebrate ventral midbrain contains neurons whose degeneration or abnormal function are linked to a number of diseases, including Parkinson's disease and schizophrenia. It is known that motor neurons develop in close proximity to the floor plate in the ventral midbrain. Midbrain projections to the striatum are involved in the control of voluntary movement (Bjorklund and Lindvall, In: *Handbook of Chemical Neuroanatomy*, eds., Borklund, et al.,Amsterdam: Elsevier, pp55–122, 1984) and loss of these neurons results in the motor disorders of Parkinson's disease (Hirsch, et al., *Nature*, 334:345, 1988). Midbrain dopaminergic neurons that innervate limbic structures and the cortex influence emotional and cognitive behavior, respectively, and abnormal function of these neurons has been associated with schizophrenia and drug addiction (Seeman, et al., *Nature*, 365:441, 1993).

While the molecular nature of the factors that specify neuronal cell fate have not been established, members of the transforming growth factor-$\beta$ (TGF-$\beta$) (Lyons, et al., *Trends in Genetics*, 7:408, 1991) or the hedgehog protein family (Smith, J. C., *Cell*, 76:193, 1994) may possess the characteristics expected from such factors as they participate in specification of cell fate, mediate inductive interactions between tissues, and in many cases act at a distance of only a few cell diameters.

The present invention establishes that hh activities encoded by these genes play a crucial role in early patterning of the developing eye and in patterning of the brain. For the first time, the invention shows that internal cleavage of hedgehog protein product is critical for full function, and that the two novel products of this auto-proteolytic cleavage display distinguishable activities, thus demonstrating that hh signaling activity is a composite effect of two separate signaling proteins that derive from a common hh protein precursor. In so doing, the invention provides the means for specific patterning and proliferation of desired neuronal cell types for addressing disorders which arise from neuronal degeneration or abnormal function.

SUMMARY OF THE INVENTION

The present invention is based on the seminal discovery that hedgehog proteins undergo auto-proteolytic cleavage which results in two separate proteins having distinct functional and structural characteristics. The two polypeptides, referred to as the "N" and "C" fragments of hedgehog, or N-terminal and C-terminal fragments, respectively, are produced after specific cleavage at a Gly↓Cys Phe site recognized by the autoproteolytic domain in the native protein. The "C" fragment functions as a cholesterol transferase during autoproteolysis thus allowing cholesterol modification of the "N" fragment.

Thus, in one embodiment, the invention provides a substantially pure polypeptide characterized by having an amino acid sequence derived from amino terminal amino acids of a hedgehog protein and having at its carboxy terminus, a Gly↓Cys Phe cleavage site specifically recognized by a proteolytic activity of the carboxy terminal fragment of the native hedgehog polypeptide.

In another embodiment, the invention provides a substantially pure polypeptide characterized by having an amino acid sequence derived from carboxy terminal amino acids of a hedgehog protein and having at its amino terminus, a Gly↓Cys Phe cleavage site specifically recognized by a proteolytic activity of the carboxy terminal fragment of the native hedgehog polypeptide.

The invention also provides a method for modulating proliferation or differentiation of neuronal cells, comprising contacting the cells with a hedgehog polypeptide. The native hedgehog polypeptide, the N, or the C fragment, or functional fragments derived therefrom, are most useful for the induction of proliferation or differentiation of neuronal cells substantially derived from floor plate neuronal cells.

In yet another embodiment, the invention provides a method for identifying a compound which affects hedgehog activity comprising incubating the compound with hedgehog polypeptide, or with biologically active fragments thereof, or with a recombinant cell expressing hedgehog, under conditions sufficient to allow the components to interact; and determining the effect of the compound on hedgehog activity or expression. For example, cholesterol level is measured as an indicator of hedgehog activity.

BRIEF DESCRIPTION OF THE DRAWINGS

FIG. 2 shows sequence similarity between hh proteins and serine proteases. hh protein sequences are aligned to residues 323 to 329 of the D. melanogaster protein and numbered as positions 1 to 7 (group A). The catalytic histidines of mammalian serine proteinases (group B) are aligned to the invariant histidine at position 7 in hh proteins.

FIG. 6 shows the embryonic distribution of wingless (wg) RNA as revealed by in situ hybridization is shown in (A) wild-type (homozygous $y^1$ $w_{1118}$), (B) hshh, and (C) hshh H329A embryos that were exposed to two 10 minute heat shocks separated by a 90-minute recovery period (33). Wild-type embryos showed little change in wg expression, whereas the wild-type protein and, to a lesser extent, the H329A protein each induced ectopic wg expression (Table 1). Panels (D), (E), and (F) show the dorsal surfaces of $y^1$ $w^{1118}$, hshh, and hshh H329A larvae, respectively, at the level of the fourth abdominal segment. These larvae were shocked for 30 minutes as embryos and allowed to complete embryogenesis. Cuticle cell types (1°, 2°, 3°, and 4°) are labeled as described (J. Heemskerk and S. DiNardo, Cell 76, 449, 1994). Note the expansion of 2° cell types (naked cuticle) at the expense of 3° and some 4° types in the hshh embryo (E) under conditions where the phenotype of hshh H329A embryos (F) is identical to that of control embryos (D).

FIG. 7 shows X-gal staining to show imaginal disc effects of ubiquitous wild type and H329 hh proteins. X-gal staining was used to follow expression of wg (A-C) or dpp (D-L) in imaginal discs of late third-instar larvae that carry wg-lacZ or dpp-lacZ reporter genes. Leg (A-F), wing (G-I) and eye-antennal discs (J-L) from control larvae (A, D, G, J), larvae carrying the hshh transgene (B, E, H, K) and larvae carrying the hshh H329A transgene (C, F, I, L) are displayed. In all panels anterior is to the left.

FIG. 9 shows the differential localizations of N and C in embryos by in situ localization of the hh transcript. FIG. 9(A) is shown in comparison to the distribution of N and C epitopes detected with Ab1 and Ab2 in panels (B) and (C), respectively. Note that the distribution of N and C epitopes span approximately one-third and one-half of each segmental unit respectively, while the transcript is limited to approximately one-quarter of each unit. In (D), the localization of C epitopes in embryos homozygous for the $hh^{13E}$ allele is detected with the use of Ab2. C epitopes in this mutant, which displays impaired auto-proteolytic activity (see text), are more restricted, and resemble the wild-type localization of N. Homozygous $hh^{13E}$ embryos were identified by loss of a marked balancer from a heterozygous parent stock. All embryos are at mid to late stage 9 (extended germ-band).

FIGS. 11A and B (SEQ ID NO: 1 and SEQ ID NO: 2) show the nucleotide and deduced amino acid sequences for partial human hh clones.

FIGS. 13A–13B shows the predicted amino acid sequences in single letter code. The amino acid sequences of zebrafish twhh and shh are aligned with those of the Shh/vhh-1/Hhg-1 class from chicken and mouse. Residues identical to all four sequences are boxed, and a dash indicates a gap in the alignment. The arrow indicates the end of the predicted signal sequence.

FIG. 15 shows the effects of ectopic hh on zebrafish development. Wild type zebrafish, Danio rerio, Ekkwill Waterlife Resources) were maintained at 28.5° C., some embryos were then cultured overnight at RT. Zebrafish embryos were injected at the 1–8 cell stage with twhh, shh, or lacZRNA and examined at 28 h of development. (a–c) Dorsal view of the midbrain-hindbrain region; anterior is left. (a) lacZ (b) twhh. (c) shh. (d–f) Frontal optical section of the forebrain region; anterior is up. (d) lacZ. (e) twhh. (f) shh. (g–i) (g-1) Lateral view of the eye region; anterior is left. (g) lacZ. (h) twhh. (i) twhh.

FIG. 16 is a table showing the effects of ectopic expression of shh, twhh and twhh mutants on zebrafish embryonic development.

Construct $U356_{HA}$ contains a stop codon in place of amino acid residue 357 as well as the H273A mutation in $U_{HA}$. Construct N encodes just the first 200 amino acids of twhh. Construct C has had the codons for residues 31–197 deleted. 17(b) shows in vitro translation of the expression constructs shown schematically in part a. Constructs were translated in vitro in the presence of $^{35}$S methionine and analyzed by autoradiography after SDS-PAGE.

FIG. 18 shows Northern blot analysis of the effect of hedgehog on expression of various neural markers.

Figure 19A:
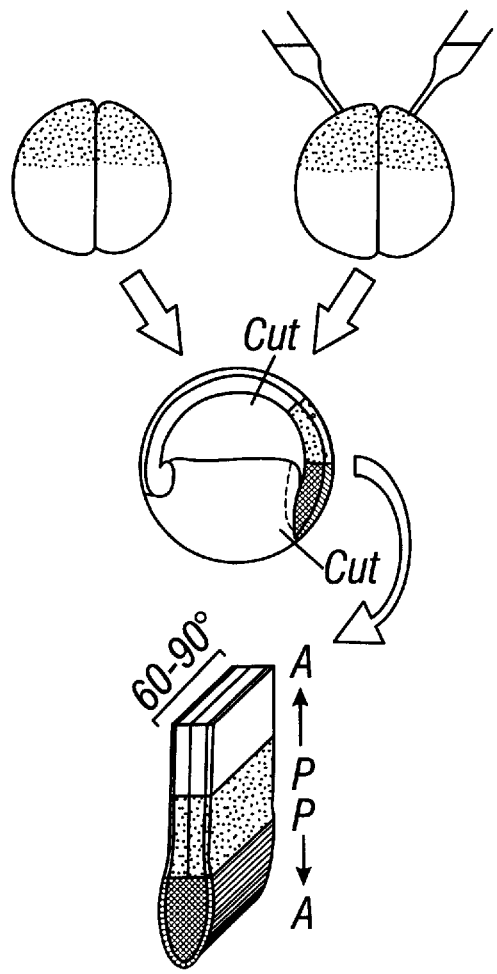
Figure 19B:
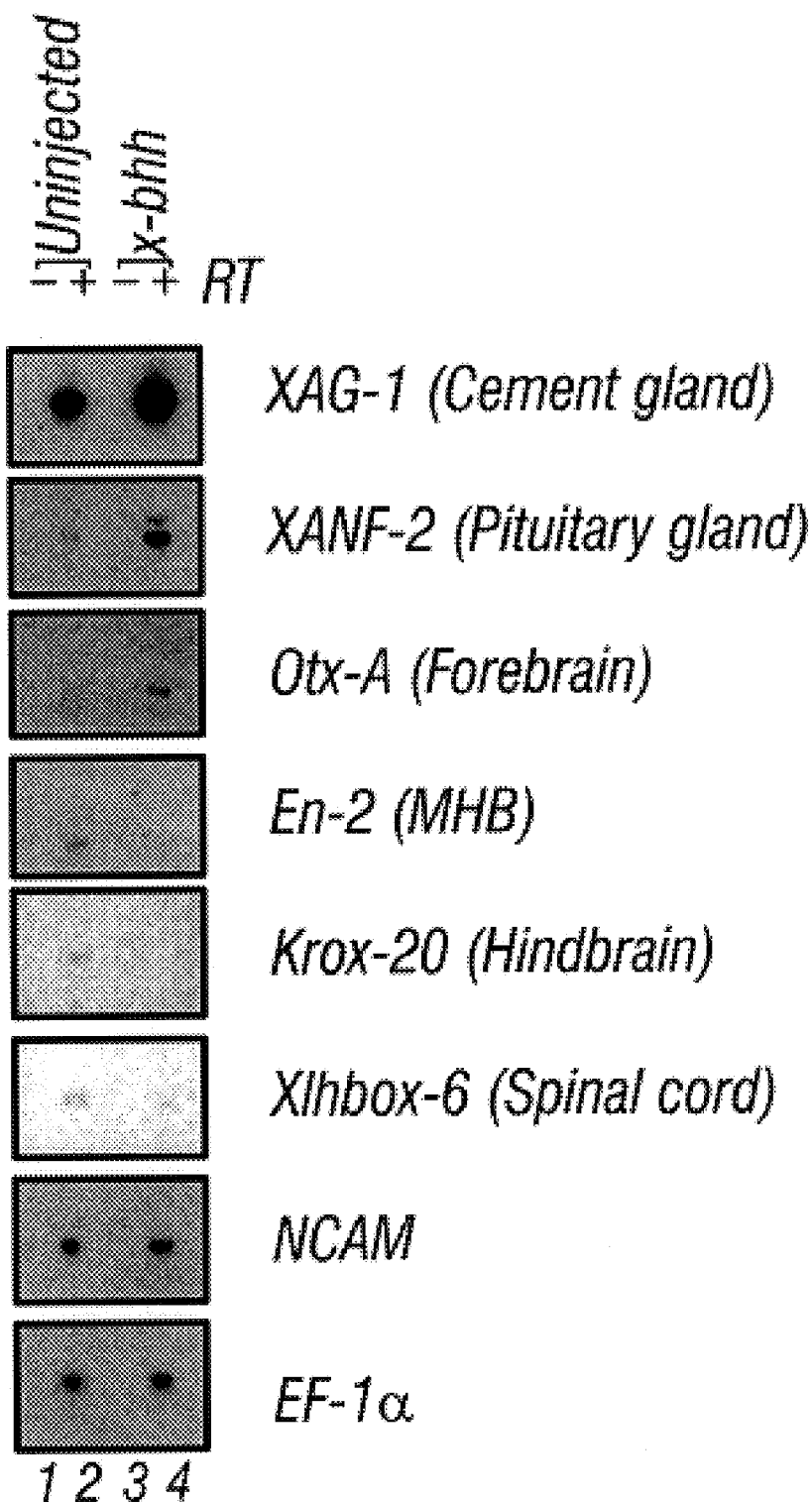

FIG. 19 shows hh synergy with naturally occurring neural markers or agents (e.g., XAG-1, XANF-2, Otx-A, En-2, Krox-20, Xlh box-6, NCAM, and EF-1α).

Figure 20A:
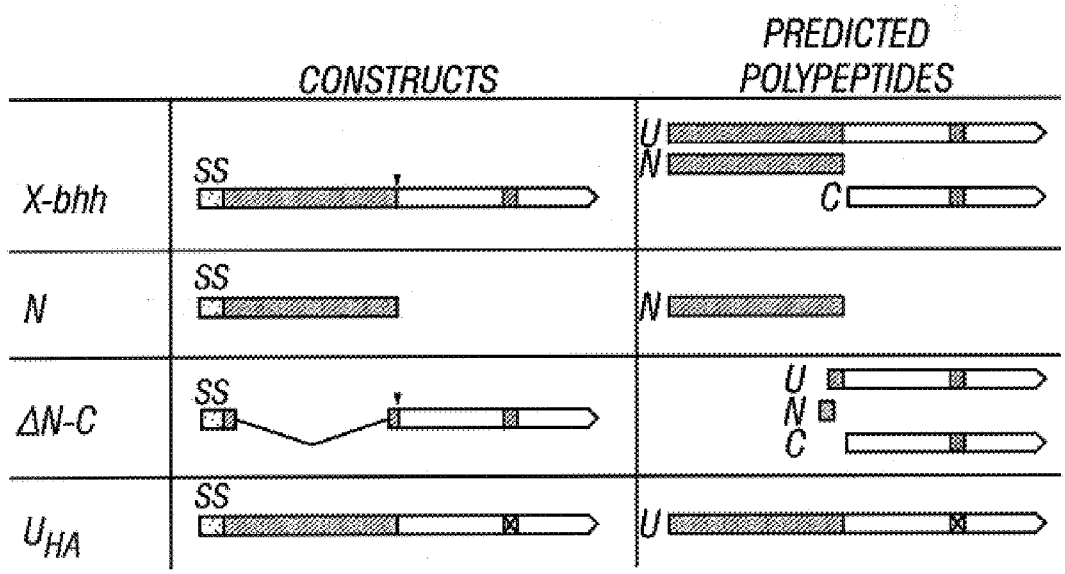
Figure 20B:
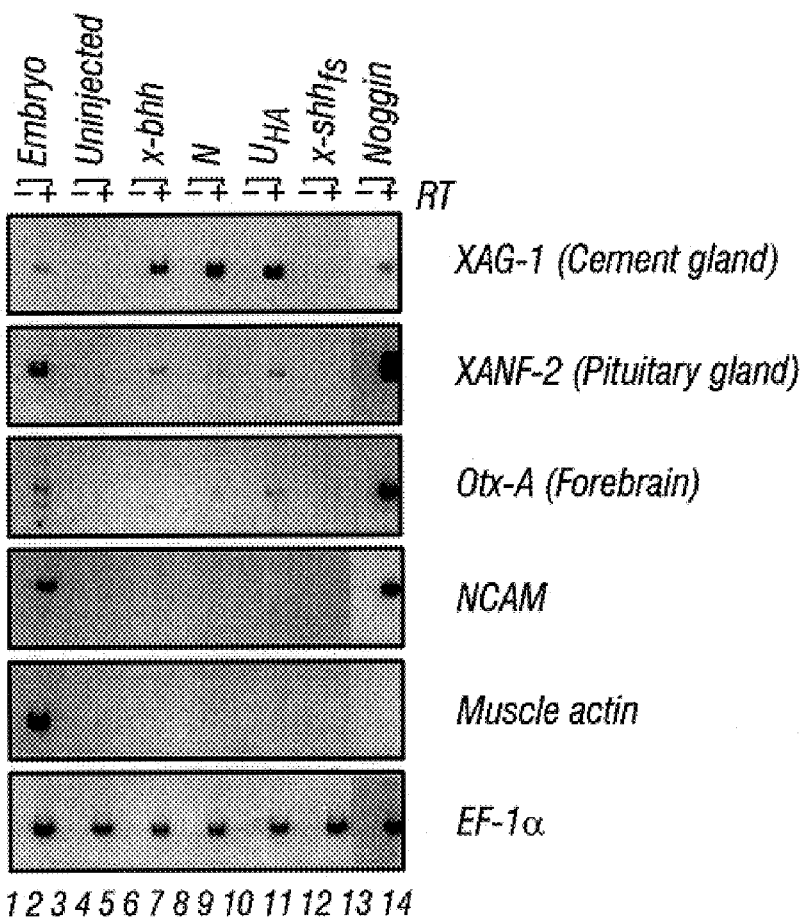

FIG. 20 shows Northern blot analysis of the effect of hedgehog N or C on various neural markers.

FIG. 21 shows ΔN-C interferes with X-bhh and N-activity in animal cap explants as shown by RT-PCR analysis.

FIG. 22A is an illustration of lipid stimulation of hedgehog autoprocessing.

FIG. 22B shows a Coomassie blue stained SDS-PAGE of autocleavage reactions in bacterially expressed $His_6Hh$-C protein.

Figure 23A:
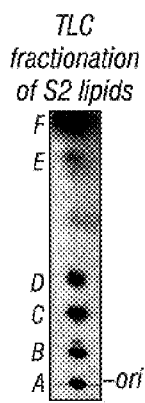

FIG. 23A is a thin layer chromatography (TLC) plate coated with silica gel G (Merck) showing the fractionation of bulk S2 cell lipids using a heptane:ether:formic acid solvent (80:20:2).

Figure 23B:
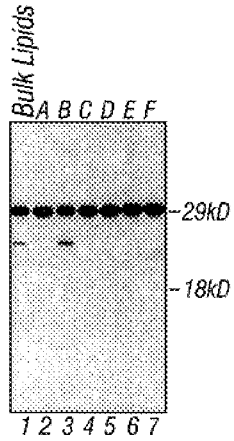

FIG. 23B is a Coomassie blue-stained SDS-polyacrylamide gel showing in vitro autocleavage reactions of the bacterially expressed His6Hh-C protein incubated with 1 mMDTT plus either unfractionated S2 cell lipids (lane 1), or spots A through F (lanes 2–7, respectively).

Figure 23C:
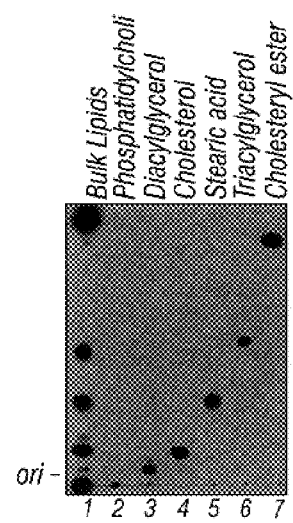

FIG. 23C is TLC of S2 cell lipids (lane 1) along with selected lipid standards: phosphatidylcholine (lane 2), a diacylglycerol (lane 3), cholesterol (lane 4), stearic acid (lane 5), a triacylglycerol (lane 6), and cholesteryl ester (lane 7). Lipid spot B comigrates with cholesterol, as also demonstrated by mixing radio-labeled cholesterol with S2 lipids before TLC fractionation.

Figure 23D:
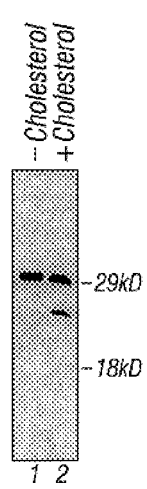

FIG. 23D is a Coomassie blue stained SDS-polyacrylamide gel showing that relative to 1 mMDTT alone (lane 1) cholesterol (0.35 mM)+1 mMDTT (lane 2) stimulates His2Hh-C autocleavage in vitro.

Figure 23E:
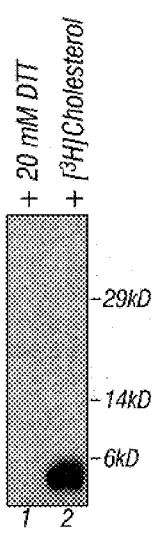

FIG. 23E is an autoradiogram of electrophoretically-resolved products of His6Hh-C autocleavage reactions driven by 20 mMDTT (lane 1) or 1 mMDTT+0.35 mM cholesterol (lane 2).

FIG. 24A shows Coomassie stained gels of His6Hh-C autocleavage reactions carried out in the presence of 20 mMDTT (lane 1), or 1 mMDTT+0.35M cholesterol (lane 2). Lane 3 contains a mixture of the samples loaded in lanes 1 and 2.

FIG. 24B is Coomassie stained gels showing protein products of His6Hh-C autocleavage reactions carried out in the presence of 1 mM DTT+0.35 mM cholesterol (lanes 1 and 2) or with 20 mM DTT (lane 3).

FIG. 24C is an autoradiogram of immunoblotted Hh amino-terminal domains purified from cultured S2 cells.

Figure 25A:
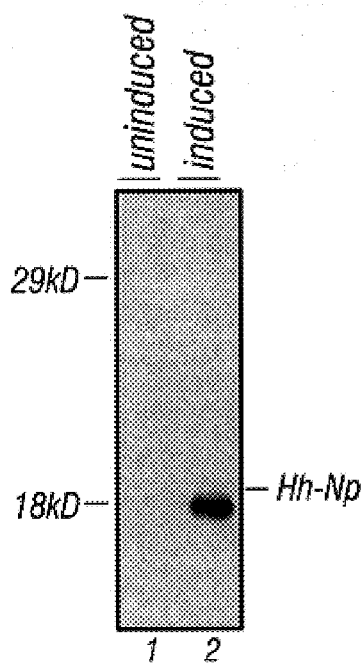

FIG. 25A is an autoradiogram of a gel loaded with total cell proteins from S2 cells containing a stably integrated Cu++-inducible hedgehog gene.

Figure 25B:
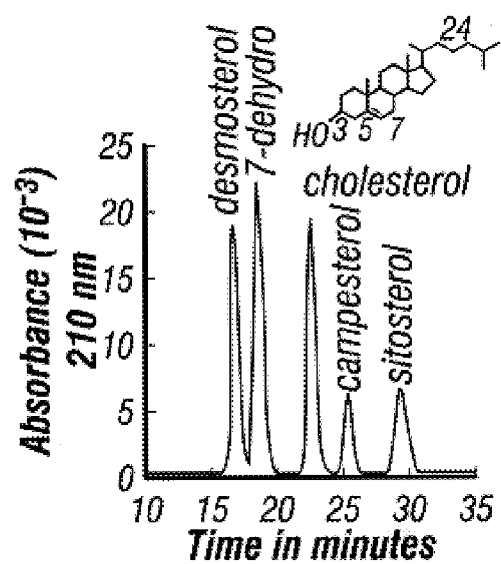

FIG. 25B is an HPLC profile of sterols separated on a C18 column by isocratic elution with a solvent containing methanol:ethanol:water (86:10:4).

Figure 25C:
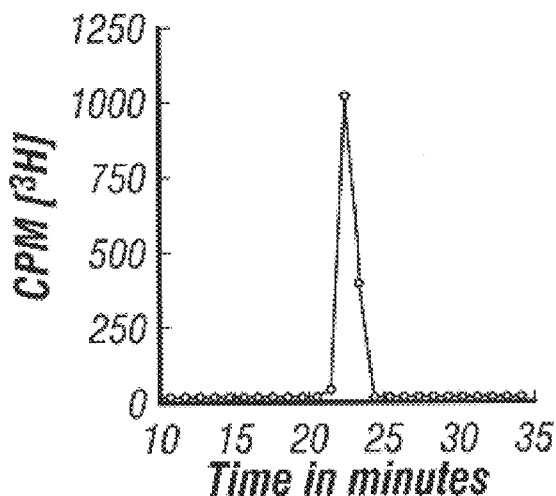

FIG. 25C shows HPLC analysis as in (B) of the adduct released by base treatment of Hh-Np metabolically labeled with [3H]cholesterol (A).

Figure 25D:
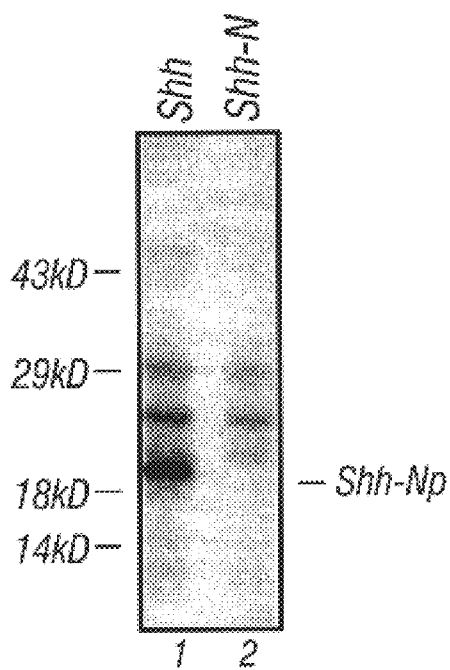

FIG. 25D shows metabolic labeling of vertebrate Sonic hedgehog protein with [3H]cholesterol. Autoradiogram of a gel loaded with total cell proteins from COS-7 cells transfected with a wild-type Sonic hedgehog expression construct (Shh, lane 1) or a construct that generates an unprocessed amino-terminal protein truncated after the conserved glycine at the site of autocleavage (Shh-N, lane 2).

DETAILED DESCRIPTION OF THE INVENTION

The present invention provides two novel polypeptides originally derived from a single precursor protein, both of which have distinct structural and functional characteristics. The proteins are derived from a hedgehog protein and can be naturally produced by auto-proteolytic cleavage of the full-length hedgehog protein. Based on evidence provided herein, which indicates that hedgehog precursor protein and the auto-proteolytic products of hedgehog precursor protein are expressed in the floorplate of the ventral midline of the neural tube and notochord, the invention now provides a method for the induction of proliferation or differentiation of neuronal cells associated with or in close proximity to the floorplate and notochord.

In a first embodiment, the invention provides a substantially pure polypeptide characterized by having an amino acid sequence derived from amino terminal amino acids of a hedgehog protein and having at its carboxy terminus, a glycine-cysteine-phenylalanine (Gly↓Cys Phe) cleavage site specifically recognized by a proteolytic activity of the carboxy terminal fragment of the native hedgehog polypeptide. This fragment is denoted the N-terminal fragment or polypeptide or "N", herein. For example, in the case of the Drosophila hedgehog, the N fragment includes amino acids 1–257 of hedgehog protein, wherein amino acids 85–257 have a molecular weight of about 19 kD by non-reducing SDS-PAGE (Amino acid residue numbers 1–257 include non-structural features such as signal sequences.). The Gly↓Cys Phe cleavage site in Drosophila hedgehog precursor protein occurs at amino acid residues 257–259. Those of skill in the art will be able to identify the Gly↓Cys Phe cleavage site in other hedgehog genes, as the amino acid location will be similar and the site will be specifically recognized by the autoproteolytic activity of the corresponding C fragment.

The N-terminal polypeptide is also characterized by being cell-associated in cells expressing the polypeptide in vitro, and being specifically localized in vertebrate or Drosophila cells or embryos, for example. In other words, this N-terminal fragment of hedgehog, remains close to the site of cellular synthesis. The association of N with the cell is a result of the processing event which involves lipophilic modification of the amino terminal domain. (See FIG. 1E and Example 19) This modification is initiated by the action of the carboxy terminal domain, generating a thioester intermediate; the carboxy-terminal domain thus does not act simply as a protease, although cleavage of a peptide bond does ultimately result from its action. Specifically, the lipid modification is a cholesterol moiety. In addition, the N fragment binds to heparin agarose in vitro.

The N polypeptide of the invention is characterized by having an amino acid sequence derived from amino terminal amino acids of hedgehog protein, e.g., 1–257 in Drosophila, wherein amino acids 1–257 have a molecular weight of about 19 kD by non-reducing SDS-PAGE. The N polypeptide includes smaller fragments which retain the functional characteristics of full length N, e.g., bind to heparin. The hedgehog protein from which N is derived includes, but is not limited to Drosophila, Xenopus, chicken, zebrafish, mouse, and human. Crystallographic analysis shows the structure of SHH-N includes the presence of a zinc ion. While not wanting to be bound by a particular theory, the presence of the zinc ion is suggestive of zinc hydrolase activity. Zinc hydrolases include proteases such as carboxypeptidase A and thermolysin, lipases such as phospholipase C, and other enzymes such as carbonic anhydrase. Alterations in the zinc hydrolase site of the amino terminal signaling domain may be useful for modulating the range of diffusion of a hedgehog protein or to alter the signaling characteristics of the amino terminal signaling domain. For example, a mutation in the zinc hydrolase site may result in a tethered protein where ordinarily the protein is secreted at a distance. The result would be induction of a cell type not typically induced. Alteration in the zinc site may result in a molecule capable of inducing motor neurons and not floor plate, and vice versa.

The identification of a cell-surface, or extracellular matrix localization of N and its expression in notochord and floor plate-associated cells, provides a means for isolation or specific selection of cells expressing N, e.g., to isolate a notochord sample or to isolate floor plate cells. In addition, antibodies directed to N are useful for histological analysis of tissues suspected of expressing N protein.

The invention also provides a substantially pure polypeptide characterized by having an amino acid sequence derived from carboxy terminal amino acids of a hedgehog protein and having at its amino terminus a Gly↓Cys Phe cleavage site specifically recognized by a proteolytic activity of the carboxy terminal fragment of the native hedgehog polypeptide. This fragment is denoted the C-terminal fragment or polypeptide or "C", herein. For example, in Drosophila this "C" polypeptide derives from the C-terminal domain of hedgehog precursor protein beginning at amino acid residue 258, wherein the full length C-terminal domain has a molecular weight of about 25 kD by non-reducing SDS-PAGE, a histidine residue at position 72, and has protease activity. The Gly↓Cys Phe cleavage site specifically recognized by the proteolytic activity of the carboxy terminal fragment of the native hedgehog polypeptide is located at amino acid residues 257–259. As described above for the N fragment, now that the present invention has shown the precise cleavage recognition site for the autoproteolytic domain of hedgehog, those of skill in the art can readily discern the cleavage site in other hedgehog proteins thereby allowing the ready identification of any N or C polypeptide of any hedgehog precursor protein.

The "C" polypeptide of the invention is derived from the C-terminus of a hedgehog precursor protein, beginning at the autoproteolytic cleavage site identified at the GCF amino acid sequence, which in Drosophila corresponds to amino acids 257–259. In Drosophila the histidine residue found invariably at amino acid residue 329 of the native hedgehog protein, and at amino acid residue 72 of the C polypeptide, is essential for auto-proteolytic cleavage between amino acids 257 and 258 (G and C). Corresponding C-polypeptides of the invention will likewise contain a similarly located histidine residue which can be readily identified, such as by comparison to the Drosophila C-polypeptide. Among various species, the proteolytic domain can be characterized by the amino acid sequence-XTXXHLXX-(SEQ ID NO: 36).

The C polypeptide of the invention, unlike N, does not significantly bind to heparin agarose. C is characterized by being released into the culture supernatant of cells expressing C polypeptide in vitro and by being localized diffusely in cells and embryos. Because C polypeptide diffuses freely, it would be detectable in various body fluids and tissues in a subject. Identification of C polypeptide expression near the midline of the neural tube, as described herein, provides a useful assay for neural tube closure in an embryo/fetus, for example. The presence of C polypeptide in amniotic fluid would be diagnostic of a disorder in which the neural tube may be malformed.

Altered levels of C polypeptide in cerebrospinal fluid may be indicative of neuro-degenerative disorders, for example. Because C polypeptide is released from the cell after synthesis and autoproteolysis of native hedgehog precursor polypeptide, tumors synthesizing and releasing high levels of C polypeptide would be detectable without prior knowledge of the exact location of the tumor.

C fragment is effective in inducing genes of the pituitary and anterior brain as well. In particular, induction is increased by the addition of a member of the TGF-β family of growth factors. For example, human activin in combination with C fragment may be effective in enhancing pituitary cell growth and activity or development. C fragment possesses cholesterol transferase activity thereby effecting precursor cleavage and transfer of a cholesterol moiety to N fragment, resulting in a biologically active N fragment.

C fragment is effective in inducing posterior markers of the brain by inhibiting N. Such a fragment is exemplified in Example 18 as ΔN-C. Therefore in another embodiment, the invention includes a polypeptide deleting amino acid residues 28–194 of X-bhh. (Autoproteolysis gives a C domain of 198–409 as well as a seven amino acid peptide, representing aa 24–27 and 195–197). This polypeptide blocks the activity of X-bhh and N in explants and reduces dorsoanterior structures in embryos. Also included are polynucleotide sequences encoding ΔN-C. ΔN-C is useful for increasing expression of posterior neural markers (e.g., En-2, Krox-20, Xlttbox-6) and decreasing expression of anterior neural markers (e.g., XANF-2, XAG-1, Otx-A) when desirable to do so to modulate neural patterning.

The term "substantially pure" as used herein refers to hedgehog N or C polypeptide which is substantially free of other proteins, lipids, carbohydrates, nucleic acids or other materials with which it is naturally associated. One skilled in the art can purify hedgehog N or C polypeptide using standard techniques for protein purification. The substantially pure polypeptide will yield a single major band on a non-reducing polyacrylamide gel. The purity of the hedgehog N or C polypeptide can also be determined by aminoterminal amino acid sequence analysis.

The invention includes a functional N or C polypeptide, and functional fragments thereof. As used herein, the term "functional polypeptide" or "functional fragment" refers to a polypeptide which possesses a biological function or activity which is identified through a defined functional assay and which is associated with a particular biologic, morphologic, or phenotypic alteration in the cell. Functional fragments of the hedgehog N or C polypeptide include fragments of N or C polypeptide as long as the activity, e.g., proteolytic activity or cholesterol transferase activity of C polypeptide remains. Smaller peptides containing the biological activity of N or C polypeptide are therefore included in the invention. The biological function, for example, can vary from a polypeptide fragment as small as an epitope to which an antibody molecule can bind to a large polypeptide which is capable of participating in the characteristic induction or programming of phenotypic changes within a cell. A "functional polynucleotide" denotes a polynucleotide which encodes a functional polypeptide as described herein.

Minor modifications of the N or C polypeptide primary amino acid sequence may result in polypeptides which have substantially equivalent activity as compared to the N or C polypeptide described herein. Such modifications may be deliberate, as by site-directed mutagenesis, or may be spontaneous. All of the polypeptides produced by these modifications are included herein as long as the proteolytic activity of C polypeptide, for example, is present. Further, deletion of one or more amino acids can also result in a modification of the structure of the resultant molecule without significantly altering its activity. This can lead to the development of a smaller active molecule which would have broader utility. For example, it is possible to remove amino or carboxy terminal amino acids which may not be required for N or C polypeptide activity.

The N or C polypeptide of the invention also includes conservative variations of the polypeptide sequence. The term "conservative variation" as used herein denotes the replacement of an amino acid residue by another biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The N fragment of the invention includes both the active form of the polypeptide and the N fragment including the uncleaved signal sequence. For example, in Drosophila where the signal sequence is internal (at about amino acids 60–80), the entire uncleaved N fragment beginning at the initiating methionine is included in the invention. Those of skill in the art can readily ascertain the nature and location of the signal sequence by using, for example, the algorithm described in von Heijne, G., *Nucl. Acids Res.* 14:4683, (1986).

The invention also provides an isolated polynucleotide sequence consisting essentially of a polynucleotide sequence encoding a polypeptide having the amino acid sequence of N or C polypeptide of the invention. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode N or C polypeptide. It is understood that all polynucleotides encoding all or a portion of N or C polypeptide are also included herein, as long as they encode a polypeptide with N or C polypeptide activity. Such polynucleotides include naturally occurring, synthetic, and intentionally manipulated polynucleotides. For example, N or C polypeptide polynucleotide may be subjected to site-directed mutagenesis. The polynucleotide sequence for N or C polypeptide also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of N or C polypeptide encoded by the nucleotide sequence is functionally unchanged. In addition, the invention also includes a polynucleotide consisting essentially of a polynucleotide sequence encoding a polypeptide having an amino acid sequence of N or C and having at least one epitope for an antibody immunoreactive with N or C polypeptide.

The polynucleotide encoding N or C polypeptide includes the entire polypeptide or fragments thereof, as well as nucleic acid sequences complementary to that sequence. A complementary sequence may include an antisense nucleotide. When the sequence is RNA, the deoxynucleotides A, G, C, and T are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein under physiological conditions. Preferably, the fragments hybridize under stringent conditions.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences; 2) antibody screening of expression libraries to detect cloned DNA fragments with shared structural features; and 3) PCR amplification of a desired nucleotide sequence using oligonucleotide primers.

Preferably the hedgehog, N, or C polynucleotide of the invention is derived from a vertebrate organism, and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981).

The development of specific DNA sequences encoding hedgehog can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A preferred method for obtaining genomic DNA, for example, is Polymerase Chain Reaction (PCR), which relies on an in vitro method of nucleic acid synthesis by which a particular segment of DNA is specifically replicated. Two oligonucleotide primers that flank the DNA fragment to be amplified are utilized in repeated cycles of heat denaturation of the DNA, annealing of the primers to their complementary sequences, and extension of the annealed primers with DNA polymerase. These primers hybridize to opposite strands of the target sequence and are oriented so that DNA synthesis by the polymerase proceeds across the region between the primers. Since the extension products themselves are also complementary to and capable of binding primers, successive cycles of amplification essentially double the amount of the target DNA synthesized in the previous cycle. The result is an exponential accumulation of the specific target fragment, approximately $2^n$, where n is the number of cycles of amplification performed (see PCR Protocols, Eds. Innis, et al., Academic Press, Inc., 1990, incorporated herein by reference).

A cDNA expression library, such as λgt11, can be screened indirectly for hedgehog, N, or C polypeptides having at least one epitope, using antibodies specific for hedgehog, N, or C. Such antibodies can be either polyclonally or monoclonally derived and used to detect expression product indicative of the presence of the desired hedgehog cDNA.

The polynucleotide sequence for hedgehog, N, or C, also includes sequences complementary to the polynucleotide encoding hedgehog, N or C (antisense sequences). Antisense nucleic acids are DNA or RNA molecules that are complementary to at least a portion of a specific mRNA molecule (Weintraub, *Scientific American*, 262:40, 1990). The invention embraces all antisense polynucleotides capable of inhibiting production of hedgehog, N, or C polypeptide. In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to cause problems than larger molecules when introduced into the target hedgehog, N, or C-producing cell. The use of antisense methods to inhibit the translation of genes is well known in the art (Marcus-Sakura, *Anal. Biochem.*, 172:289, 1988). Inhibition of target nucleotide would be desirable, for example, in inhibiting cellproliferative disorders, such as certain tumors, which are mediated by hedgehog, N or C.

In addition, ribozyme nucleotide sequences for hedgehog, N or C are included in the invention. Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

There are two basic types of ribozymes namely, tetrahymena-type (Hasselhoff, Nature, 334:585, 1988) and "hammerhead" -type. Tetrahymena-type ribozymes recognize sequences which are four bases in length, while "hammerhead" -type ribozymes recognize base sequences 11–18 bases in length. The longer the recognition sequence, the greater the likelihood that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

DNA sequences encoding hedgehog, N or C can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the hedgehog, N or C polynucleotide sequences may be inserted into a recombinant expression vector. The term "recombinant expression vector" refers to a plasmid, virus or other vehicle known in the art that has been manipulated by insertion or incorporation of the hedgehog, N or C genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J. Biol. Clem., 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding hedgehog, N or C can be expressed in either prokaryotes or eukaryotes, although post-translational modification of eukaryotically derived polypeptides, such as carboxylation, would occur in a eukaryotic host. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Methods which are well known to those skilled in the art can be used to construct expression vectors containing the hedgehog, N or C coding sequence and appropriate transcriptional/translational control signals. These methods include in vitro recombinant DNA techniques, synthetic techniques, and in vivo recombination/genetic techniques. See, for example, the techniques described in Maniatis, et al., 1989 Molecular Cloning A Laboratory Manual, Cold Spring Harbor Laboratory, N.Y.

A variety of host-expression vector systems may be utilized to express the hedgehog, N or C coding sequence. These include but are not limited to microorganisms such as bacteria transformed with recombinant bacteriophage DNA, plasmid DNA or cosmid DNA expression vectors containing the hedgehog, N or C coding sequence; yeast transformed with recombinant yeast expression vectors containing the hedgehog, N or C coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the Hedgehog, N or C coding sequence; insect cell systems infected with recombinant virus expression vectors (e.g., baculovirus) containing the hedgehog, N or C coding sequence; or animal cell systems infected with recombinant virus expression vectors (e.g., retroviruses, adenovirus, vaccinia virus) containing the hedgehog, N or C coding sequence, or transformed animal cell systems engineered for stable expression.

Depending on the host/vector system utilized, any of a number of suitable transcription and translation elements, including constitutive and inducible promoters, transcription enhancer elements, transcription terminators, etc., may be used in the expression vector (see e.g., Bitter, et al., 1987, Methods in Enzymology, 153:516–544). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted hedgehog, N or C coding sequence.

In bacterial systems a number of expression vectors may be advantageously selected depending upon the use intended for the expressed. For example, when large quantities of hedgehog, N or C are to be produced, vectors which direct the expression of high levels of fusion protein products that are readily purified may be desirable. Those which are engineered to contain a cleavage site to aid in recovering are preferred. Such vectors include but are not limited to the E. coli expression vector pUR278 (Ruther, et al., EMBO J, 2:1791, 1983), in which the Hedgehog, N or C coding sequence may be ligated into the vector in frame with the lac Z coding region so that a hybrid -lac Z protein is produced; pIN vectors (Inouye and Inouye, Nucleic Acids Res., 13:3101, 1985; Van Heeke and Schuster, J. Biol. Chem. 264:5503, 1989) and the like.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu and Grossman, 31987, Acad. Press, N.Y., Vol. 153, pp.516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger and Kimmel, Acad. Press, N.Y., Vol. 152, pp. 673–684; and The Molecular Biology of the Yeast Saccharomyces, 1 982, Eds. Strathern, et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

In cases where plant expression vectors are used, the expression of the hedgehog, N or C coding sequence may be driven by any of a number of promoters. For example, viral promoters such as the 35S RNA and 19S RNA promoters of CaMV (Brisson, et al., Nature, 310:511, 1984), or the coat protein promoter to TMV (Takamatsu, et al., EMBO J., 6:307, 1987) may be used; alternatively, plant promoters such as the small subunit of RUBISCO (Coruzzi, et al., EMBO J., 3:1671–1680, 1984; Broglie, et al., Science, 224:838, 1984); or heat shock promoters, e.g., soybean hsp 17.5-E or hsp 17.3-B (Gurley, et al., Mol. Cell. Biol., 6:559, 1986) may be used. These constructs can be introduced into plant cells using Ti plasmids, Ri plasmids, plant virus vectors, direct DNA transformation, microinjection, electroporation, etc. For reviews of such techniques see, for example, Weissbach and Weissbach, 1988, Methods for Plant Molecular Biology, Academic Press, N.Y., Section VIII, pp. 421–463; and Grierson and Corey, 1988, Plant Molecular Biology, 2d Ed., Blackie, London, Ch. 7–9.

An alternative expression system which could be used to express is an insect system. In one such system, Autographa californica nuclear polyhedrosis virus (AcNPV) is used as a vector to express foreign genes. The virus grows in Spodoptera frugiperda cells. The hedgehog, N or C coding sequence may be cloned into non-essential regions (for example the polyhedrin gene) of the virus and placed under control of an AcNPV promoter (for example the polyhedrin promoter). Successful insertion of the hedgehog, N or C coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (e.g., see Smith, et al., J. Viol., 46:584, 1983; Smith, U.S. Pat. No. 4,215,051).

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, secretion of the gene product may be used as host cells for the expression of hedgehog, N or C. Mammalian cell lines may be preferable. Such host cell lines may include but are not limited to CHO, VERO, BHK, HeLa, COS, MDCK, -293, and WI38.

Mammalian cell systems which utilize recombinant viruses or viral elements to direct expression may be engineered. For example, when using adenovirus expression vectors, the hedgehog, N or C coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the protein in infected hosts (e.g., see Logan and Shenk, Proc. Natl. Acad Sci. USA, 81:3655, 1984). Alternatively, the vaccinia virus 7.5K promoter may be used. (e.g., see, Mackett, et al., Proc. Natl. Acad. Sci. USA, 79:7415, 1982; Mackett, et al., J. Virol., 49: 857, 1984; Panicali, et al., Proc. Natl. Acad Sci. USA, 79:4927, 1982). Of particular interest are vectors based on bovine papilloma virus which have the ability to replicate as extrachromosomal elements (Sarver, et al., Mol. Cell. Biol, 1:486, 1981). Shortly after entry of this DNA into mouse cells, the plasmid replicates to about 100 to 200 copies per cell.

Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing an d directing the expression of the hedgehog, N or C gene in host cells (Cone and Mulligan, Proc. Natl. Acad. Sci. USA, 81:6349, 1984). High level expression may also b e achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the hedgehog, N or C cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., Cell, 11: 223, 1977), hypoxanthine-guanine phosphoribosyltransferase (Szybalska and Szybalski, Proc. Natl. Acad. Sci. USA, 48:2026, 1962), and adenine phosphoribosyltransferase (Lowy, et al., Cell, 22: 817, 1980) genes can be employed in tk$^-$, hgprt$^-$ or aprt$^-$ cells respectively. Also, antimetabolite resistance can be used as the basis of selection for dhfr, which confers resistance to methotrexate (Wigler, et al., Natl. Acad. Sci. USA, 77: 3567, 1980; O'Hare, et al., Proc. Natl. Acad. Sci. USA, 78: 1527, 1981); gpt, which confers resistance to mycophenolic acid (Mulligan and Berg, Proc. Natl. Acad. Sci. USA, 78: 2072, 1981; neo, which confers resistance to the aminoglycoside G-418 (Colberre-Garapin, et al., J. Mol. Biol., 150:1, 1981); and hygro, which confers resistance to hygromycin (Santerre, et al., Gene, 30:147, 1984) genes. Recently, additional selectable genes have been described, namely trpB, which allows cells to utilize indole in place of tryptophan; hisD, which allows cells to utilize histinol in place of histidine (Hartman and Mulligan, Proc. Natl. Acad. Sci. USA, 85:8047, 1988); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Transformation of a host cell with recombinant DNA may be carried out by conventional techniques as are well known to those skilled in the art. Where the host is prokaryotic, such as *E coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the hedgehog, N or C of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with or which bind to hedgehog, N or C polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature*, 256:495, 1975). The term antibody as used in this invention is meant to include intact molecules as well as fragments thereof, such as Fab and F(ab')$_2$, which are capable of binding an epitopic determinant on hedgehog, N or C. The antibodies of the invention include antibodies which bind to the N or C polypeptide and which bind with immunoreactive fragments N or C.

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable genetically fused single chain molecule.

Methods of making these fragments are known in the art. (See for example, Harlow and Lane, *Antibodies: A Laboratory Manual*, Cold Spring Harbor laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the hedgehog, N or C polypeptide of the invention can be prepared using an intact polypeptide or fragments containing small peptides of interest as the immunizing antigen. The polypeptide such as N or C, or fragments thereof used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference). It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Antibodies as described herein as having specificity for N polypeptide, e.g., Ab1 (residues 83–160), are useful for specific identification of cells or tissues expressing the N fragment of hedgehog. Similarly, antibodies described herein as having specificity for C polypeptide, e.g., Ab2 (residues 300–391), are useful for specific identification of cells or tissues expressing the C fragment of hedgehog. Both antibodies, naturally, will also detect native hedgehog polypeptide.

The N and C-specific antibodies of the invention are useful for purification of N and C polypeptide, respectively, especially using the antibodies immobilized on solid phase. By contacting a sample with anti-N antibody, both N and native hedgehog polypeptides can be isolated. By next contacting the sample removed by anti-N antibodies, with anti-C antibodies, the native hedgehog polypeptide is removed, thus allowing purification of N polypeptide. In a similar manner, C polypeptide can be antibody purified from a sample.

Monoclonal antibodies of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "immunometric assay" or "sandwich immunoassay", includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Monoclonal antibodies can be bound-to many different carriers and used to detect the presence of N or C polypeptide. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

For purposes of the invention, N or C polypeptide may be detected by the monoclonal antibodies when present in biological fluids and tissues. Any sample containing a detectable amount of N or C can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis. C polypeptide in particular is detectable in biological samples, since it tends to diffuse more readily than N polypeptide.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-C or N immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

The invention also provides a method for modulating proliferation or differentiation of neuronal cells comprising contacting the cells with a hedgehog polypeptide. The hedgehog polypeptide may be a native hedgehog polypeptide, or a N or C polypeptide, or functional fragments thereof. Preferably, the modulation is induction of proliferation or differentiation of a particular cell type. This can involve either synergistic positive induction of neuronal cells by N, or negative modulation by delta N–C for example (Lai, et al., *Development* 121:2349, 1995). Delta N–C enhances expression of posterior relative to anterior neural genes and does so through inhibition of N (see EXAMPLE 18 and FIG. 18D). In addition to hedgehog polypeptide, a TGF-β factor may also be utilized in the method of the invention.

Previous studies with the rat hedgehog gene showed that co-culture of cells expressing rat hedgehog precursor gene, with explant from neural tube, was sufficient to induce formation of motor neurons and floor plate from the explant (Jessesl, T., and Dodd, J., In *Cell-Cell Signaling in Vertebrate Development* (ed. E. J. Robertson, et al., pp 139–155, San Diego, Calif.), 1993). Therefore, based on the Examples herein showing that hedgehog is expressed near the floor plate of the ventral midline of the neural tube and notochord, neuronal cells substantially derived from floor plate neuronal cells can be induced by contacting the cells with hedgehog, N or C polypeptide. As used herein, the term "substantially derived", refers to those cells from the floor plate or proximate to the floor plate. For example, such cells include motor neurons and dopaminergic neurons. Those of skill in the art will be able to identify other neuronal cells substantially derived from the floor plate. Preferably the cells are vertebrate cells and most preferably, human cells.

In addition, as described herein in the Examples, hedgehog, and particularly C fragment, induces the expression of pituitary genes. Hedgehog is also effective in inducing anterior brain gene expression as exemplified by the OTX-A marker. Further, the addition of a TGF-β family member, for example activin, may be used to further induce expression of such genes. Other TGF-β family members will be known to those of skill in the art. This apparent synergy of hh fragments with TGF-β family members occurs through the TGF-β protein inducing expression of neural inducers such as noggin and follistatin. The hh fragment then synergizes with these inducers to pattern neural gene expression.

hh fragments may also be useful as nerve-sparing agents or in restoring or promoting appropriate patterning during the healing of major limb trauma. In addition, the N and C fragments may be useful in the area of genetic counseling. Specifically, familial midline defects such as cyclopia, polydactyly or neural tube defects may be diagnosed by mapping close to hh. Since autoproteolytic defects may be responsible for the disorders, N or C therapy could be provided.

The invention also provides an autoproteolytic fusion protein comprising a first polypeptide including the proteolytic domain of the C polypeptide of the invention, a cleavage site recognized by the first polypeptide, and a second polypeptide. (It is understood that the first and second polypeptides can be reversed.) The auto-proteolytic activity of the native hedgehog protein is found entirely within the C polypeptide, therefore, the C polypeptide is useful for producing a fusion polypeptide which can then be cleaved at the junction of the C polypeptide and the second polypeptide. The fusion protein may optionally have a purification tag, such as a poly-histidine tag for isolation on a nickel column, or an antibody epitope tag, preferably on the C fragment. The cleavage site includes the sequence "GCF", which is recognized by the proteolytic domain of the C polypeptide and is utilized to cleave the second polypeptide from the C fragment. Also included in the invention is a polynucleotide encoding the fusion protein of the invention.

The invention also provides a method for producing an autoproteolytic fusion protein comprising operably linking a first polynucleotide, wherein the first polynucleotide encodes a first polypeptide including the proteolytic domain of the C polypeptide of the invention and the cleavage site recognized by the proteolytic domain, and a second polynucleotide encoding a second polypeptide. As described above, the fusion protein may also include a carrier peptide and/or a purification tag.

The C polypeptide or functional fragment thereof is useful as a fusion partner to cause lipophilic modification and tethering of other proteins in vivo or in vitro. Such fusion proteins may be desirable for factors whose activity is required in a localized manner, either by targeting DNA constructs to specific cells or by introducing cells transfected with specific DNA constructs, for example. It may be desirable to lipid-modify a normally secreted protein in order to produce a cell-associated protein. For example, it may be desirable to produce a viral antigen that remains cell associated. Specifically, cholesterol is covalently attached to the N-terminal protein during autoprocessing and the C polypeptide acts as an intramolecular cholesterol transferase.

Alternatively, the C polypeptide or functional fragments thereof can be used as a fusion partner with a protein of interest (e.g., Protein X fused to hh-C domain). Such fusions form thioesters at the junction between Protein X and hh-C (via an S to N shift). The thioesters are then available as substrates for a peptide ligation reaction in which any peptide or protein having an amino terminal cysteine (Peptide Y) is added and undergoes spontaneous rearrangement (S to N shift) that generates a stable peptide bond between Protein X and Peptide Y (Protein X-peptide bond-Peptide Y). For example, a protein that is toxic when produced in vivo could be produced in vitro using the hh-C domain fusion protein method.

The fusion polypeptide may also include an optional carrier peptide. The "carrier peptide", or signal sequence, is located at the amino terminal end of the fusion peptide sequence. In the case of eukaryotes, the carrier peptide is believed to function to transport the fusion polypeptide across the endoplasmic reticulum. The secretory protein is then transported through the Golgi apparatus, into secretory vesicles and into the extracellular space or, preferably, the external environment. Carrier peptides which can be utilized according to the invention include pre-pro peptides which contain a proteolytic enzyme recognition site. Acceptable carrier peptides include the amino terminal pro-region of calcitonin or other hormones, which undergo cleavage at the flanking dibasic sites. However, it should be noted that the invention is not limited to the use of any particular peptide as a carrier.

Other carrier peptides are known to those skilled in the art or can be readily ascertained without undue experimentation.

In one embodiment of the invention, a carrier peptide which is a signal sequence is included in the expression vector, specifically located adjacent to the N-terminal end of the fusion polypeptide. This signal sequence allows the fusion protein to be directed toward the endoplasmic reticulum. Typically, the signal sequence consists of a leader of from about 16 to about 29 amino acids, starting with two or three polar residues and continuing with a high content of hydrophobic amino acids; there is otherwise no detectable conservation of sequence known. Such signal sequences are known to those of skill in the art, and include the naturally occurring signal sequence derived from a hedgehog protein.

The fusion polypeptide of the invention includes a polypeptide encoded by a structural gene, preferably at the amino-terminus of the fusion polypeptide. Any structural gene is expressed in conjunction with the C-polypeptide (polynucleotide) and optionally a carrier peptide. The structural gene is operably linked with the carrier in an expression vector so that the fusion polypeptide is expressed as a single unit.

The identification of the autoproteolysis of hedgehog into the N and C domains is useful in a screening method to identify compounds or compositions which affect this processing activity. Thus, in another embodiment, the invention provides a method for identifying a composition which affects hh processing, which can be determined by activity or gene expression, comprising incubating the components, which include the composition to be tested (e.g., a drug, a small molecule, a protein) and a hh polypeptide or a recombinant cell expressing hedgehog or a gene encoding a C domain or functional fragment thereof operably linked to an N domain or functional fragment thereof, under conditions sufficient to allow the components to interact, then subsequently measuring the effect the composition has on hedgehog activity or expression. Fragments of hedgehog polypeptide or polynucleotide can be used in the method of the invention as long as autoproteolytic activity remains (e.g., the construct exemplified in FIGS. 12*a* and 12*b*, Example 10). The observed effect on hh may be either inhibitory or stimulatory. For example, one can determine whether the N domain is associated with the cell, or whether the N domain is secreted into the medium, in other words, whether incomplete processing has occurred. Such methods for determining the effect of the compound or composition on hh processing include those described herein (see Example 10, FIGS. 12*a* and 12*b*) such as time course of autoproteolytic cleavage or course of cleavage based on concentration ranges. Alternatively, the effect of the composition on hh can be determined by the expression of anterior or posterior neural markers. Other methods for determining the effect of a composition on processing of N and C will be known to those of skill in the art. Various labels can be used to detect the N and C domains, for example, a radioisotope, a fluorescent compound, a bioluminescent compound, a chemiluminescent compound, a metal chelator or an enzyme could be used. Those of ordinary skill in the art will know of other suitable labels or will be able to ascertain such, using routine experimentation.

The identification of the lipid modification of the N domain of hedgehog by the C domain, resulting in a biologically active N domain, is useful in a screening method to identify compounds or compositions which affect the cholesterol transferase/processing activity. Thus, in another embodiment, the invention provides a method for identifying a composition which affects hh biological activity, which can be determined by activity or lipid modification (i.e., cholesterol), comprising incubating the components, which include the composition to be tested (e.g., a drug, a small molecule, a protein) and a hh polypeptide or a recombinant cell expressing hedgehog or a gene encoding a C domain or functional fragment thereof operably linked to an N domain or functional fragment thereof, under conditions sufficient to allow the components to interact, then subsequently measuring the effect the composition has on hedgehog activity. Fragments of hedgehog polypeptide or polynucleotide can be used in the method of the invention as long as cholesterol transferase activity remains. The effect on hh may be either inhibitory or stimulatory. For example, one can determine whether the N domain is associated with the cell, or whether the N domain is secreted into the medium, in other words, whether incomplete processing and modification has occurred. Such methods for determining the effect of the compound or composition on hh processing include those described herein (see Example 10, FIGS. 12*a* and 12*b*) such as time course of autoproteolytic cleavage or course of cleavage based on concentration ranges. Alternatively, the effect of the composition on hh can be determined by the level of cholesterol modification as determined by thin layer chromatography (e.g., Example 19, FIG. 23) or incorporation of labeled cholesterol into hh protein (e.g., Example 19, FIG. 25) or into a fragment appended to the transferase (c) domain. Other methods for determining the effect of a composition on processing and cholesterol modification of N and C will be known to those of skill in the art. Various labels can be used to detect the N and C domains, for example, a radioisotope, a fluorescent compound, a bioluminescent compound, a chemiluminescent compound, a metal chelator or an enzyme could be used. Those of ordinary skill in the art will know of other suitable labels or will be able to ascertain such, using routine experimentation.

As used herein, "hh activity" as described in the screening method refers preferably to autoproteolytic activity. However, it is understood, that one of skill in the art could use the above-described screening assay to identify a composition having an affect on other hh activities, for example, zinc hydrolase activity or cholesterol transferase activity. Appropriate assays for determining the effect on such activities will be known to those of skill in the art. Example 19 provides lipophilic modification assays useful in the described screening methods above.

Now that the present invention describes the cholesterol modification of N by C, it is possible to design various diagnostic and therapeutic approaches for treatment of hh associated disorders due to defective or altered sterol modification. For example, Smith-Lemli-Optiz syndrome (SLOS) is characterized by a loss of hh function and a sterol profile indicating a cholesterol deficiency. Therefore, SLOS may be diagnosed and/or treated based on the cholesterol profile. Further, a defect in Desert hh in the testes is associated with male sterility (M. Bitgood, L. Shen, A. P. McMahon, Current Biology 6, 298, 1996; A. Vortkamp et al., Science 273, 613, 1996), consequently, it may be possible to design male contraceptives based on defective cholesterol modification of hh. On the other hand, if sterility or decreased fertility was desirable, hh cholesterol transferase activity could be altered to reduce cholesterol modification. Processing of the C and N fragments of hh is required for hh activity, therefore alterations in cholesterol modification of the amino terminal fragment may also be related to developmental defects in vertebrate embryos.

The following examples are intended to illustrate but not limit the invention. While they are typical of those that might be used, other procedures known to those skilled in the art may alternatively be used.

EXAMPLE 1

HEDGEHOG PROTEIN PROCESSING

Figures 1A, 1B, 1C, 1D:
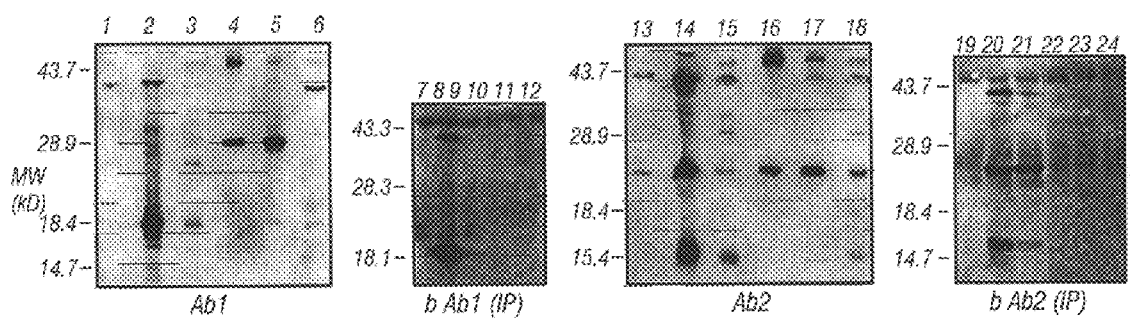
FIG. 1B and D are blots of samples immunoprecipitated with Ab1 (B, lanes 7–9), Ab2 (D, lanes 19–21), or preimmune serum (B, lanes 10–12, and D, lanes 22–24).
Figure 1E:
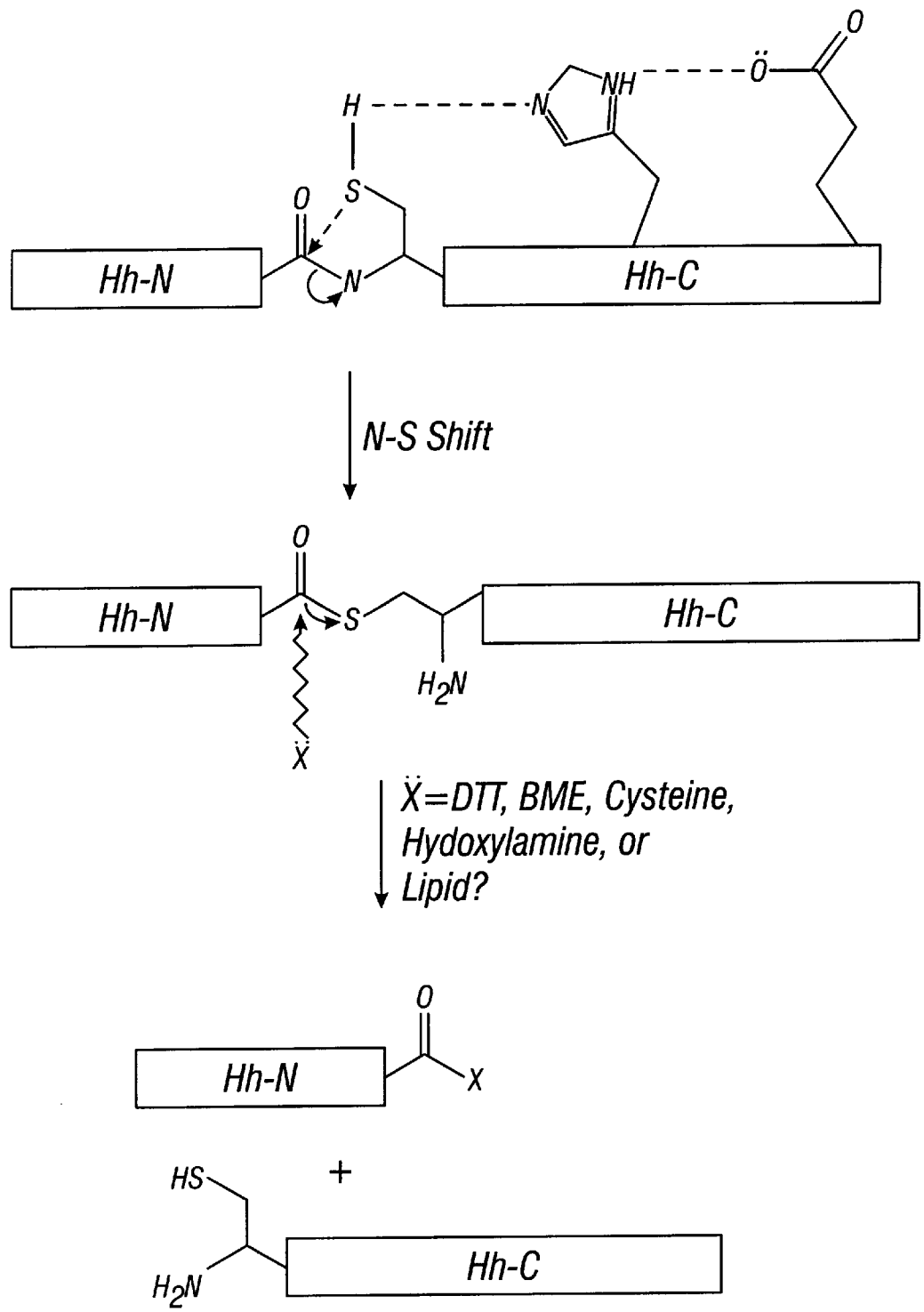
FIG. 1E shows a schematic illustration of the hedgehog cleavage mechanism.

The full length form of the hh protein (F) migrates with a mobility corresponding to a relative molecular mass of 46 kD. FIGS. 1(A) and (C) are immunoblots with antibodies against amino- (Ab1) and carboxy-terminal (Ab2) epitopes. GST fusion proteins containing either residues 83 to 160 or 300 to 391 from HH protein were expressed in *Escherichia coli*, purified as recommended [F. M. Ausubel, et al., *Current Protocols in Molecular Biology* (Greene and Wiley-Interscience, New York, 1991)], and used to immunize rabbits by standard methods. The antibodies were affinity purified on a column of $His_6$-U protein [E. Harlow and D. Lane, *Antibodies: A Laboratory Manual* (Cold Spring Harbor Laboratory, Cold Spring Harbor, N.Y., 1988)] linked to Affi-Gel 10 beads (Bio-Rad). The purification was performed as described (Harlow and Lane, supra) except that the acid and base elutions contained 10 percent dioxane. Biotinylated hh antibodies were prepared by purifying the rabbit antisera over a protein A column, followed by biotinylation with the use of the Immunoprobe biotinylation kit (Sigma).

Immunoprecipitations were performed as described [Harlow and Lane] with the use of cold RIPA lysis buffer containing 0.25 mM phenylmethylsulfonyl fluoride (PMSF) and 5 mM EDTA for tissue homogenization. Lysates were precleared twice with pre-immune rabbit serum plus protein A beads (Gibco-BRL). Affinity-purified antibodies or pre-immune serum was then added, and the immunoprecipitation was performed with protein A beads, with the use of NP-40 lysis buffer for the washes.

Immunoblots were performed with affinity purified Ab1 or Ab2 by either of two chemiluminescence based protocols. In the first protocol (used in FIGS. 1, 3, and 5) samples were resolved on 15 percent or 12 percent SDS-polyacrylamide gels (F. M. Ausubel et al., supra) and transferred to Magnagraph nylon membranes (MSI) by electroblotting. Blots were developed with the use of an alkaline phosphatase conjugated donkey anti-rabbit IgG secondary antibody and Lumi-Phos 530 (Boehringer Mannheim) under recommended conditions. In the second protocol (used in FIG. 8), samples were transferred to nitrocellulose filters (Schleicher and Schuell), and blots were developed using ECL reagents (Amersham) as recommended. The secondary antibody in this case was horseradish peroxidase conjugated goat anti-rabbit IgG (Jackson ImmunoResearch). Lanes contain protein from induced untransfected S2 cells (lanes 1 and 13), transfected S2 cells induced to express hh (lanes 2 and 14), imaginal discs (lanes 3 and 15), wild type embryos (lanes 6 and 18), and in vitro translations of synthetic h mRNA both in the presence (lanes 5 and 17) and absence of microsomes (lanes 4 and 16).

cDNAs encoding various hh protein species were cloned into the pMK33 vector, which allows for inducible expression under metallothionine promoter control (M. R. Koelle et al., *Cell* 67:59,1991). Stable S2 cell lines were made by transfection of the hh/pMK33 plasmids with constant selection for hygromycin resistance. Proteins were expressed by plating a log phase culture of cells diluted to 0.1 $A_{595}$ units, waiting 48 hours, inducing with $CuSO_4$ at 0.2 mM final concentration, and harvesting the cells and/or supernatant 24 hours later. Cell samples for immunoblotting were made by adding 10 volumes of 1×SDS PAGE loading buffer to pelleted cells.

In vitro translations were performed with the use of the TNT coupled transcription-translation system (Promega). $^{35}S$ methionine (DuPont NEN) was used for detection by autoradiography. In the heparin binding experiment in vitro translation lysate with microsomes that produce wild-type hh protein was added to heparin agarose (Sigma) or Sepharose CL-4B (Pharmacia) beads pre-equilibrated with heparin binding buffer (HBB; 20 mM Tris (7.4), 150 mM NaCl, 0.1 percent Triton X-100). Samples were incubated at 4° C. for four hours with gentle rocking. After pelleting the beads, supernatants in some samples were analyzed (lanes 2 and 4). The beads were then washed 5 times with chilled HBB and samples (lanes 3 and 5) were subsequently eluted at 80° C. for 10 minutes in SDS PAGE loading buffer (F. M. Ausubel et al., supra).

Embryos from the wild-type Canton-S line and from the matings, hshh/hshh or hshh H329A/hshh H329A X y; Sco/ CyO, enlacZll::wg (Kassis, et al., *Proc. Natl. Acad. Sci. U.S.A.* 89: 1919, 1992), were collected 0 to 16 hours after egg laying (AEL) at 25° C. They were heat shocked for 30 minutes at 37° C. and allowed to recover for 1 hour at 25° C. Embryos in FIG. 1 (Canton-S) were collected 4 to 8 hours AEL at 25° C. In preparation for immunoblotting, all embryos were dechorionated in 2.6 percent sodium hypochlorite and homogenized in 10 volumes of 1×SDS PAGE loading buffer.

Multiple species were detected and minor cross reactive bands are seen in most samples including extracts of induced untransfected S2 cells (lanes 1 and 13). One of these bands (occurring in both panels) co-migrates with U (at 39 kD) and is particularly abundant in lane 6 of FIG. 1(A).

FIGS. 1(B) and (D) are blots of samples immunoprecipitated with Ab1 (B, lanes 7–9), Ab2 (D, lanes 19–21), or pre-immune serum (B, lanes 10–12 and D, lanes 22–24). Detection was with biotinylated derivatives of Ab1 (B) and Ab2 (D). Samples used were: induced untransfected S2 cells, lanes 7, 10, 19 and 22; transfected S2 cells induced to express hh, lanes 8, 11, 20 and 23; and embryos, lanes 9, 12, 21 and 24. For either antibody, hh protein fragments were specifically immunoprecipitated from hh expressing cells and embryos, but not from untransfected cells. (E) In the schematic diagram, cleavage sites are denoted by arrows. The cleavage site marked by the asterisk is inferred by identification of only one cleavage product and may therefore occur at another location within the C fragment. The first two columns to the right of the diagram indicate the reactivity of Ab1 and Ab2 to each hh fragment. The other columns indicate the presence (+) or absence (−) of each hh fragment in the various samples. Parentheses around F and $N_{SS}$ indicate that these species are detected in in vitro translation reactions but not in vivo.

Figure 1F:
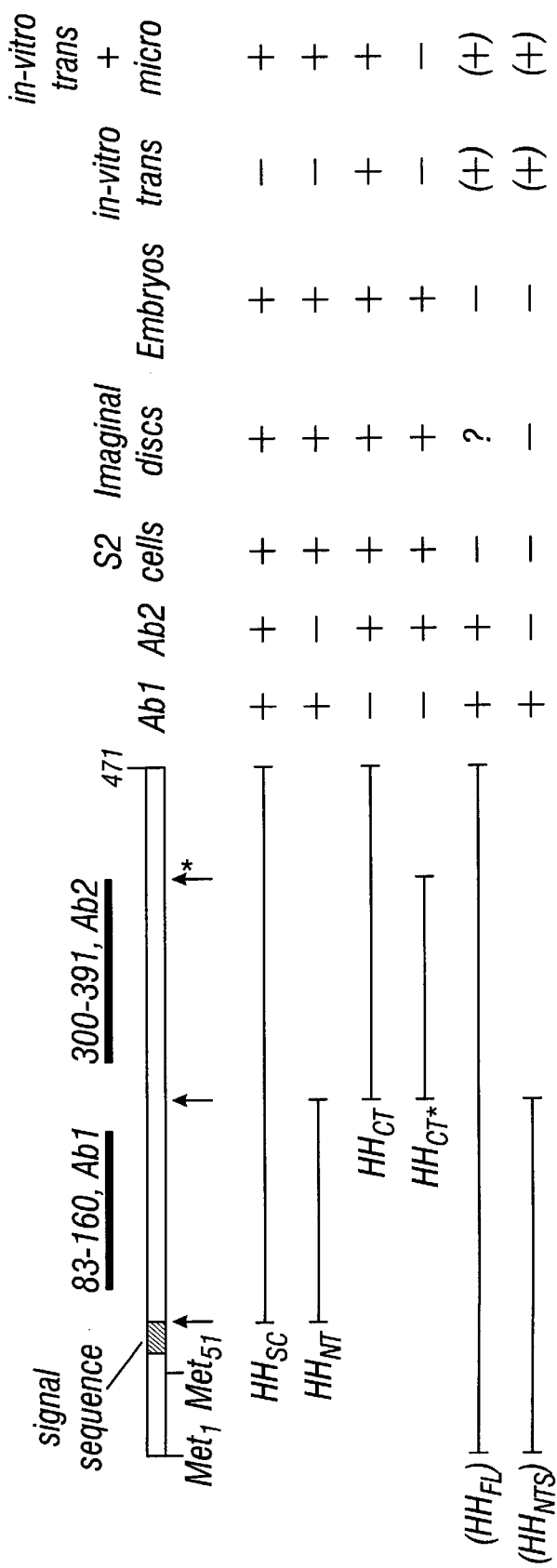
FIG. 1 shows processing of the hh protein by immunoblots (A,C) with antibodies against amino (Ab1) and carboxy-terminal (Ab2) epitopes.

The 46 kD species was detected from in vitro translation extracts by Ab1 and Ab2 (FIG. 1, lanes 4 and 16), and was partially converted to a species of 39 kD (U) when translation occurred in the presence of microsomes (FIG. 1, lanes 5 and 17). A 39 kD species co-migrating with U is also present in extracts from all in vivo sources, but none of these extracts contain detectable levels of F. U represents the signal-cleaved form of F; signal cleavage thus appears to be relatively inefficient in vitro, as reported previously, (J. J. Lee, et al, Cell, 71:33, 1992), but is highly efficient in vivo. To confirm that signal cleavage indeed is occurring at this unusual internal location, a mutation that changes residue $S_{84}$ to N at the predicted signal cleavage site was introduced. This mutation prevented conversion by microsomes of F to U and also produced a species that comigrated with F upon transfection into cultured S2 cells. The effects of independently mutating the two methionine codons present upstream of the signal sequence were also examined. In vitro translation of the sequence in which the first methionine is removed produces a protein species intermediate in mobility between F and U, and this species is converted to a species that comigrates with U in the presence of microsomes or when produced in vivo. Alteration of the second methionine codon caused no change in the electrophoretic mobility of Hh protein produced in vivo or in vitro.

Smaller species of Hh proteins from in vivo sources have been reported previously (T. Tabata and T. B. Kornberg, Cell 76: 89, 1994). The latter study examined not endogenous proteins, but proteins induced to express at high levels from exogenously introduced constructs. The antibody used did not distinguish epitopes from distinct portions of the molecule.

In addition to signal cleavage, a further cleavage of the U precursor is responsible for generating other forms of hh protein observed in vivo. This was deduced from the observation that Ab1 and Ab2 both detected the U (uncleaved) species, but also interacted individually with smaller protein species expressed endogenously in embryos and imaginal discs or with species expressed upon introduction of the hh gene into S2 cells. Ab1 thus interacts with a 19 kD species from all of these tissues (FIG. 1, lanes 2, 3, 6, 8, 9), while Ab2 interacts with a 25 kD species and a 16 kD species (FIG. 1, lanes 14, 15, 18, 20, 21). The 19 kD species hereafter is referred to as N (N-terminal fragment), the 25 kD species as C(C-terminal fragment) and the 16 kD species as C*; these species represent the major forms of endogenous hh protein present in vivo.

The proposed cleavages by which these species arise are shown schematically in the bottom portion of FIG. 1. The N and C species are uniquely detected by Ab1 and Ab2, respectively, and the sum of the relative masses of the two smaller species is roughly equivalent to the relative mass of U. The electrophoretic mobilities of the F and U species are somewhat at variance with their predicted relative masses (52.1 kD and 43.3 kD, respectively). The identities of these species were confirmed by in vitro translation of a variety of hedgehog open reading frames modified to contain different extents of sequence at the $NH_2$— or COOH— terminus, and by insertion of epitope tags. The migration anomalies appear to be associated with protein species in which sequences from both the $NH_2$— and COOH-terminal fragments are simultaneously present. The mobilities of the $NH_2$— and COOH-terminal fragments, in contrast, correspond to relative masses (19 kD and 25 kD, respectively) that sum to yield 44 kD, roughly equivalent to the expected relative mass of U.

A simple mechanism that could account for the derivation of the two smaller species therefore would be a single internal cleavage of the U precursor. Processing of the hh protein when translated in vitro also yields a 25 kD species (C; lanes 16 and 17) and either a 29 kD or 19 kD (N) species (lanes 4 and 5). The 19 kD species comigrates with N, and its formation depends upon the presence of microsomes, consistent with the proposal that N derives from F by signal cleavage and a further internal cleavage. The overall pathway for formation of the predominant forms of hh protein observed in vivo thus appears to involve signal cleavage of F to generate U. U is then cleaved internally to form N and C, which are the predominant forms found in vivo. Further processing of the 25 kD C species might then generate the 16 kD C* species, but whether this processing is a single cleavage event or not is not clear since Ab2 does not recognize the smaller 9 kD fragment that would result. The processing of C to generate C* appears to occur with greater efficiency in imaginal discs as compared to embryos (compare lanes 15 and 18); this may be caused by the more extended mass isolation procedure of imaginal discs (O. M. Eugene, et al., Tissue Culture Assn. Man., 5: 1055, 1979).

EXAMPLE 2

AUTO-PROTEOLYSIS OF THE HEDGEHOG PROTEIN

The comigration of endogenous and in vitro-generated hh protein species suggested that in vitro processing is similar to that observed in vivo. FIG. 2 shows limited sequence similarity between hh proteins and serine proteinases. hh protein sequences are aligned to residues 323 to 329 of the D. melanogaster protein and numbered as positions 1 to 7 (group A). Conserved hh residues are in bold letters. The catalytic histidines (A. J. Barrett, in Proteinase inhibitors A. J. Barrett, G. Salvesen, Eds. (Elsevier, Amsterdam, 1986) pp. 3–22) of mammalian serine proteinases (group B) are aligned to the invariant histidine at position 7 in Hh proteins. Abbreviations are as follows: C-Shh, chicken Sonic hh (R. D. Riddle, et al., Cell 75: 1401, 1993); M-Shh, mouse Sonic hh (Y. Echelard et al., Cell 75: 1417, 1993) (identical to Hhg-1; R vhh-1, rat vhh-1 (H. Roelink et al., Cell 76: 761, 1994); Z-Shh, zebrafish Sonic hh (S. Krauss, et al., Cell 75: 1431, 1993) (identical to shh) and zebrafish vhh-1, (H. Roelink et al., supra); twhh, no other abbreviation; M-Dhh, mouse Desert hh (Y. Echelard et al., Cell 75: 1417, 1993); M-Ihh, mouse Indian hh (Y. Echelard et al., supra); CHT, bovine chymotrypsin; TRP, bovine trypsin; ELA, porcine elastase; UKH, human urokinase; C1R, human complement factor 1R; C1S, human complement factor 1S; MCP, rat mast cell protease; FAX, human blood clotting factor X; TPA, human tissue plasminogen activator.

FIG. 2 shows that a seven residue region of hh coding sequence (residues 323 to 329 in the Drosophila protein) displays some similarity to the sequences of serine proteases. This region lies approximately two thirds of the distance from the signal cleavage site to the carboxy-terminus, and includes Thr and His, residues (positions 4 and 7 in FIG. 2) that are invariant among all hh sequences from all species. In the serine proteases, this conserved sequence contains an invariant His that acts as a general base in catalysis (A. J. Barrett, in *Proteinase inhibitors* A. J. Barrett, G. Salvesen, Eds. Elsevier, Amsterdam, 1986, pp. 3–22).

Figure 3A:
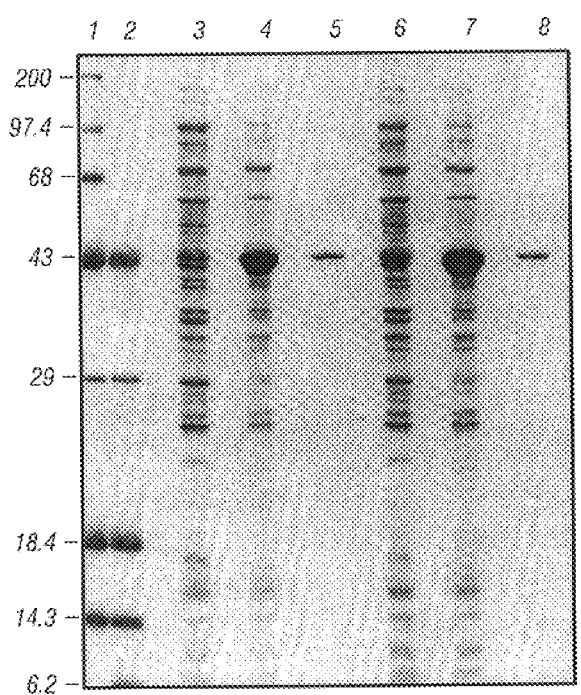
FIG. 3 shows autoproteolysis of the hh protein. 3A shows a Coomasie blue stained polyacrylamide gel showing production and purification of $His_6$-U and $His_6$-$U_{H329A}$ proteins from E. coli. Samples were molecular weight markers (lanes 1 and 2); lysates of E. Coli cells carrying the $His_6$-U expression construct without (lane 3) and with (lane 4) induction by IPTG; purified $His_6$-U protein (lane 5); lysates of E. coli cells that carry the $His_6$-$U_{H329A}$ expression construct without (lane 6) and with (lane 7) induction by IPTG; purified $His_6$-$U_{H329A}$ protein (lane 8).
FIG. 3(B) is an immunoblot detected with Ab2 showing transfected S2 cells induced to express hh (lane 1); $His_6$-U and $His_6$-$U_{H329A}$ proteins incubated in cleavage reaction buffer for 0 hours (lanes 2 and 5), for 20 hours (lanes 3 and 6), and for 20 hours in the presence of 20 mM TAME (a serine protease inhibitor) (lanes 4 and 7).
Figure 3B:
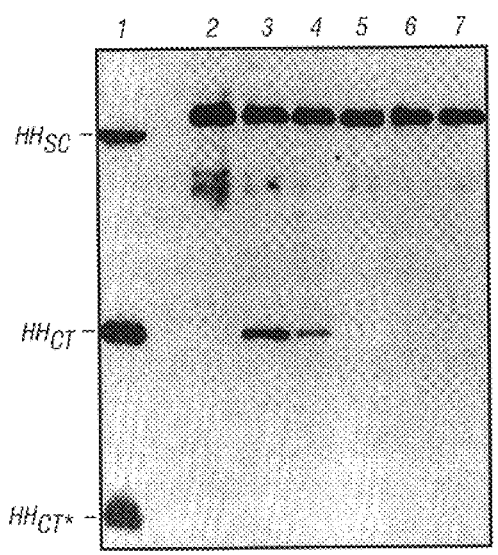

To determine whether this invariant His residue in the hh protein indeed plays a role in auto-proteolysis, two proteins from *E. coli* were purified: one carried the wild type sequence and the other a substitution of an Ala codon for the His codon at position 329 (H329A). Both of these proteins were engineered to contain a hexa-histidine tag at the amino terminus fused to Drosophila sequences extending from a residue just before the signal cleavage site to the carboxy-terminus (residues 83 to 471; the wild type form of this protein is referred to as $His_6$-U). Both proteins were extensively purified under denaturing conditions using a $Ni^{++}$-chelating matrix. FIG. 3(A) is a coomasie blue stained polyacrylamide gel that shows the production and purification of $His_6$-U and $His_6$-$U_{H329A}$ proteins from *E. coli*. Samples were molecular weight markers (lanes 1 and 2); lysates of *E. coli* cells carrying the $His_6$-U expression construct without (lane 3) and with (lane 4) induction by IPTG; purified $His_6$-U protein (lane 5); lysates of *E. coli* cells that carry the $His_6$-$U_{H329A}$ expression construct without (lane 6) and with (lane 7) induction by IPTG; purified $His_6$-$U_{H329A}$ protein (lane 8). Purified proteins were essentially homogeneous except for several minor species of lower relative mass; these species are endogenous breakdown products of the full-length proteins since they were absent in uninduced extracts and were detectable with hh antibodies. FIG. 3(B) is an immunoblot detected with Ab2 showing transfected S2 cells induced to express hh (lane 1); $His_6$-U and $His_6$-$U_{H329A}$ proteins incubated in cleavage reaction buffer for 0 hours (lanes 2 and 5), for 20 hours (lanes 3 and 6), and for 20 hours in the presence of 20 mM TAME (a serine protease inhibitor) (lanes 4 and 7). Upon incubation the $His_6$-U, but not the $His_6$-$U_{H329A}$ protein, released a fragment presumed to be C on the basis of reactivity with Ab2 and co-migration with C produced in S2 cells. Release of C (lane 3) was only partially inhibited by TAME.

Preliminary proteinase inhibitor studies have been performed on in vitro translated Hh protein by adding various inhibitors at the start of the translation reaction. These studies have been complicated by the fact that numerous protease inhibitors lower or block translation efficiency. In some cases the effectiveness of an inhibitor was assayed by determining if addition of an inhibitor to a completed translation reaction will inhibit the self-processing that normally continues to occur. At this time we can only state the following with certainty: (i) the serine protease inhibitor TAME (-p-toluenesulfonyl-L-arginine methyl ester) inhibits auto-proteolysis of in-vitro translated Hh protein; (ii) soybean trypsin inhibitor, a, anti-trypsin, aprotitin, leupeptin, and E-64 do not block auto-proteolysis of translated Hh protein; and (iii) TAME partially inhibits auto-proteolysis of purified $His_6$-U protein (FIG. 3, panel B).

As seen in FIG. 3B, upon dilution of denaturant the wild type protein but not the H329A mutant protein released a 25 kD species detectable by Ab2 and identical in mobility with the C species produced from in vitro translations and various in vivo sources. This cleavage was also observed when the wild type protein was purified and renatured by other protocols and cleaved under distinct conditions. Plasmids encoding the $His_6$-U and $His6$-$U_{H329A}$ proteins were generated by inserting sequences corresponding to residues 83 to 471 from the wild-type or hh H329A ORF into the pRSETB expression vector (Invitrogen). Proteins were induced in BL21 (DE3)/pLysS *E. coli* cells as described (F. M. Ausubel et al., supra). The basic purification was performed on Ni-NTA agarose beads (Qiagen) by a denaturing protocol with the use of 6 M guanidinium HCl and 8 M urea essentially as recommended (a detailed protocol of exact conditions used is available upon request). Washes contained 0.2 percent Tween 20 and 5 mM b-mercaptoethanol. The final wash buffer was: 6 M urea, 100 mM Tris, 500 mM NaCl, 20 percent glycerol, (pH 7.4). Elutions were with the final wash buffer containing 250 mM imidazole. In vitro cleavage reactions were performed by incubating the purified protein (diluted 1:30 in the final mix) in cleavage buffer [50 mM Tris, 500 mM NaCl, 5 percent glycerol, 0.2% Triton X-100, 50 mM DTT, (pH 7.4)]. To isolate soluble full-length $His_6$-U protein free from denaturants or detergents, additional steps were taken (this refers to the other renaturation protocols mentioned in the text). Full-length protein from the eluate described above was further purified from breakdown products by precipitation, by urea removal through dialysis. The precipitate was then re-solubilized in a buffer containing guanidinium HCl and loaded onto another Ni-NTA agarose column. After washing as described, the protein was re-folded (while attached to the beads) by gradual dilution of urea (from 6M to 0.5M) with dilution buffer [(100 mM Tris, 500 mM NaCl, 20 percent glycerol, (pH 7.4)] over an 8 hour period at 4° C. The protein was eluted with dilution buffer containing 250 mM imidazole and 0.5M urea. The eluate was dialyzed in 100 mM Tris, 150 mM NaCl, 10 percent glycerol, (pH 7.4) at 4° C. and stored at −70° C.

EXAMPLE 3

MAPPING THE AUTO-PROTEOLYTIC FUNCTIONS OF hh

To more precisely define the domain of the hh protein responsible for this auto-proteolytic event, the effects of several distinct types of mutations upon in vitro processing were examined. The most informative mutation was a deletion that removes residues 89 to 254 (Δ89–254), which together constitute most of the amino acids within the portion of the molecule presumed to form the N fragment. In vitro translations of wild-type and mutant Hh proteins from Drosophila (FIGS. 4A–C) and zebrafish (FIG. 4D) are shown. The locations of mutations and cleavage sites (arrows) in these proteins are schematically illustrated (FIG. 4E). In the Drosophila protein (FIGS. 4A, B, and C), auto-proteolysis is blocked or severely inhibited by several mutations in the COOH-terminus (H329A, 294 trunc, 410 trunc, flu408 and 456 trunc), but is unaffected by a large deletion (Δ89–254) or insertion of a flu-tag epitope trimer (flu227) in the $NH_2$-terminus. Auto-proteolysis thus depends primarily on residues within the C fragment (sequences to the right of the cleavage site in the diagram below; see FIG. 1). Furthermore, the H329A/flu227 double mutant is not cleaved by wild-type protein in a mixing experiment (lane 11), suggesting an intramolecular mechanism for auto-proteolysis. Hh proteins encoded by the zebrafish genes twhh and shh display a pattern of processing (D) similar to that of the Drosophila protein although the $NH_2$-terminal fragment of each zebrafish protein (23 kD for twhh and 22 kD for shh) has a lower apparent mass than the COOH-terminal fragment (25 kD for twhh and shh). This is the result of a shorter stretch of residues that precedes the signal sequences as compared to the Drosophila protein. Processing is blocked by H273A and H270A mutations in twhh and shh proteins respectively (analogous to the H329A mutation in the Drosophila protein), which suggests an auto-proteolytic processing mechanism is used similar to that observed for the Drosophila protein.

In vitro translations were performed with the use of the TNT coupled transcription-translation system (Promega).$^{35}$S methionine (DuPont NEN) was used for detection by autoradiography. In the heparin binding experiment (FIG. 8C), in vitro translation lysate with microsomes that produce wild-type Hh protein was added to heparin agarose (Sigma) or Sepharose CL-4B (Pharmacia) beads pre-equilibrated with heparin binding buffer (HBB; 20 mM Tris (7.4), 150 mM NaCl, 0.1 percent Triton X-100). Samples were incubated at 4° C. for four hours with gentle rocking. After pelleting the beads, supernatants in some samples were analyzed (lanes 2 and 4). The beads were then washed 5 times with chilled HBB and samples (lanes 3 and 5) were subsequently eluted at 80° C. for 10 minutes in SDS PAGE loading buffer (F. M. Ausubel et al., supra).

All mutations in the hh gene were generated in the plasmid pF1 (J. J. Lee, et al., supra). Mutations in the zebrafish twhh and shh genes were generated with the original cDNA clones as described (Ekker, et al., *Current Biology*, 5(8): 944,1995). All point mutations were generated with the use of recombinant circle PCR (D. H. Jones and S. C. Winistorfer, *Biotechniques* 12: 528, 1992). The flu408 and flu227 mutations were generated by inserting a trimer of the influenza hemagglutinin antigen (42 residues for flu408 and 43 residues for flu227) into the AlwN I and Bgl I sites present in the hh ORF (nucleotide positions 1604 and 1058 respectively) (J. J. Lee, et al., supra). The Δ89–254 mutation was generated by removing sequences between the EcoN I site (644) and the Pml I site (1145). The 294 trunc mutation was generated by removing sequences between the Acc I site (1265) and the Xcm I site (1792). The 410 trunc mutation was previously generated and identified as $Hh_{410}$ (J. J. Lee, et al, supra). To map the mutation in the $hh^{13E}$ allele (base change $C_{1756}$ to A; coding change $Tyr_{457}$ to STOP), DNA isolated from $hh^{13E}$/TM3 was used to seed PCR reactions generating regions of the hh ORF and flanking sequences, which were subcloned into Bluescript KSM (Stratagene). Six clones each, derived from two different PCR amplifications were sequenced.

Figure 4A:
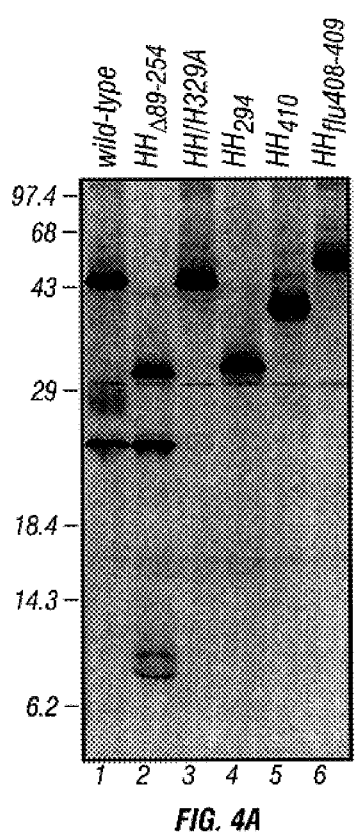
FIG. 4 shows autoproteolytic functions of Drosophila (4A-C) and zebrafish (D) hh proteins map to the carboxy terminal fragments by in vitro translations of wild-type and mutant hh proteins. The locations of mutations and cleavage sites (arrows) in these proteins are illustrated schematically in 4E.

As seen in lanes 1 and 2 of FIG. 4A, this construct generates a full length species of a mobility corresponding to the expected relative mass of 33 kD, and two cleaved products whose apparent relative masses (25 and 9 kD) sum to give the relative mass of the larger species. The smaller of the cleaved products will occasionally migrate as two bands as seen in FIG. 4A. We have chosen the lower of the two bands between the 14.3-kD and 6.2-kD markers for our molecular weight measurement. The larger of the two cleaved products comigrates with the C species produced from the wild type protein, suggesting that the Δ89–254 hh protein contains the residues normally present in C and all of the determinants required for auto-proteolysis, including the normal cleavage site; most of the residues within N are dispensable for auto-proteolytic activity.

Figure 4B:
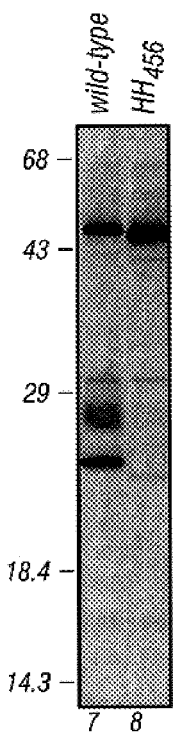

In contrast, lesions affecting residues presumed to lie within C block auto-proteolysis in vitro. All mutations tested by in vitro translation were also examined in S2 cells by immunoblotting. In all cases the patterns of cleavage in S2 cells were identical to those observed in translations except that C* was always present whenever C was formed. The former fragment was not observed in translations. These include the H329A mutation described above, a mutation that inserts an influenza virus epitope between residues 408 and 409 (flu408), and three mutations that cause premature termination of the protein at the carboxy terminus. The two most severe truncations, 294 trunc and 410 trunc, are mutations generated in vitro. They cause a loss of 177 and 61 residues, respectively, from the carboxyl-terminus of the protein, and neither undergoes proteolysis. The 456 trunc hh protein is like that encoded by the EMS-induced $hh^{13E}$ mutant allele, which results in the loss of 15 residues from the carboxy-terminus of the protein. This protein undergoes auto-proteolysis, as demonstrated by the appearance of a 24 kD band in place of C, but the efficiency of the reaction is much impaired in vitro (FIG. 4B). Auto-proteolysis of the hh protein relies mainly upon residues within C; deletion or alteration of residues within this domain is associated with reduced efficiency of processing, and one such deletion appears to be the cause of the $hh^{13E}$ mutation.

Figure 4C:
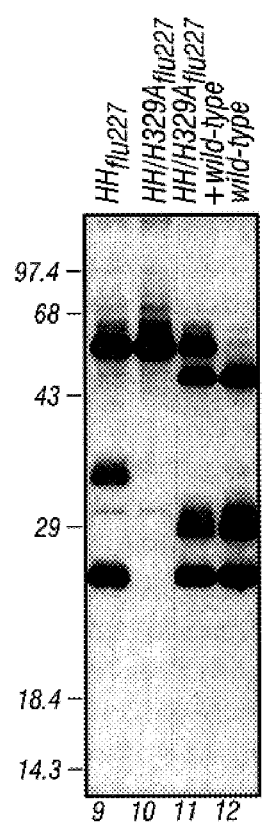

The sequence homology and auto-proteolytic function of the full length hh protein suggested the possibility that F or the C fragment is a sequence-specific protease. As a first step in clarifying the mechanism of auto-proteolysis, an influenza virus epitope tag was introduced into the N-terminus of a hh open reading frame that also carried a H329A mutation. FIG. 4C shows that the insertion of the epitope tag alone does not interfere with auto-proteolysis (lane 9), and yields a normal C fragment and an N fragment of increased relative mass (compare to wild type in lane 12). The protein carrying both mutations does not undergo proteolysis (lane 10), and since the epitope-tagged N fragment migrates differently from N, this double mutant provides an ideal substrate to look for intermolecular cleavage upon mixture with a wild type sequence. Lane 11 shows that in such a mixture, although normal N is formed, no tagged N can be detected. Thus, in this experiment, no appreciable intermolecular cleavage occurs. We also failed to detect intermolecular cleavage in the following two experiments: (i) co-transfection of wild type and 410 trunc sequences into S2 cells (the cleaved 410 trunc protein would yield a smaller and therefore identifiable form of C); (ii) mixing of excess unlabelled, purified $His_6$-U protein with labelled, in vitro translated H329A mutant protein. Thus, although an intermolecular mechanism for regulation of auto-proteolysis or for cleavage of other proteins can not be ruled out, the current evidence suggests that cleavage of the hh protein occurs predominantly by an intramolecular mechanism.

Figure 4D:
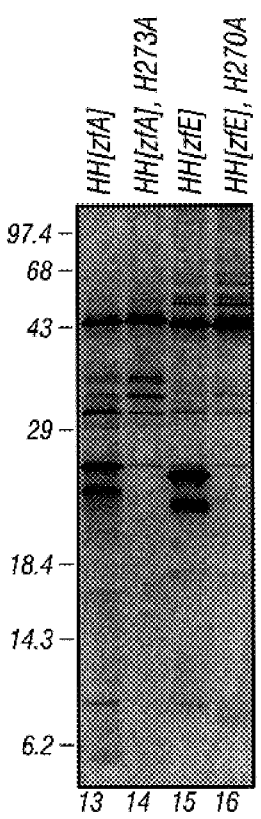
Figure 4E:
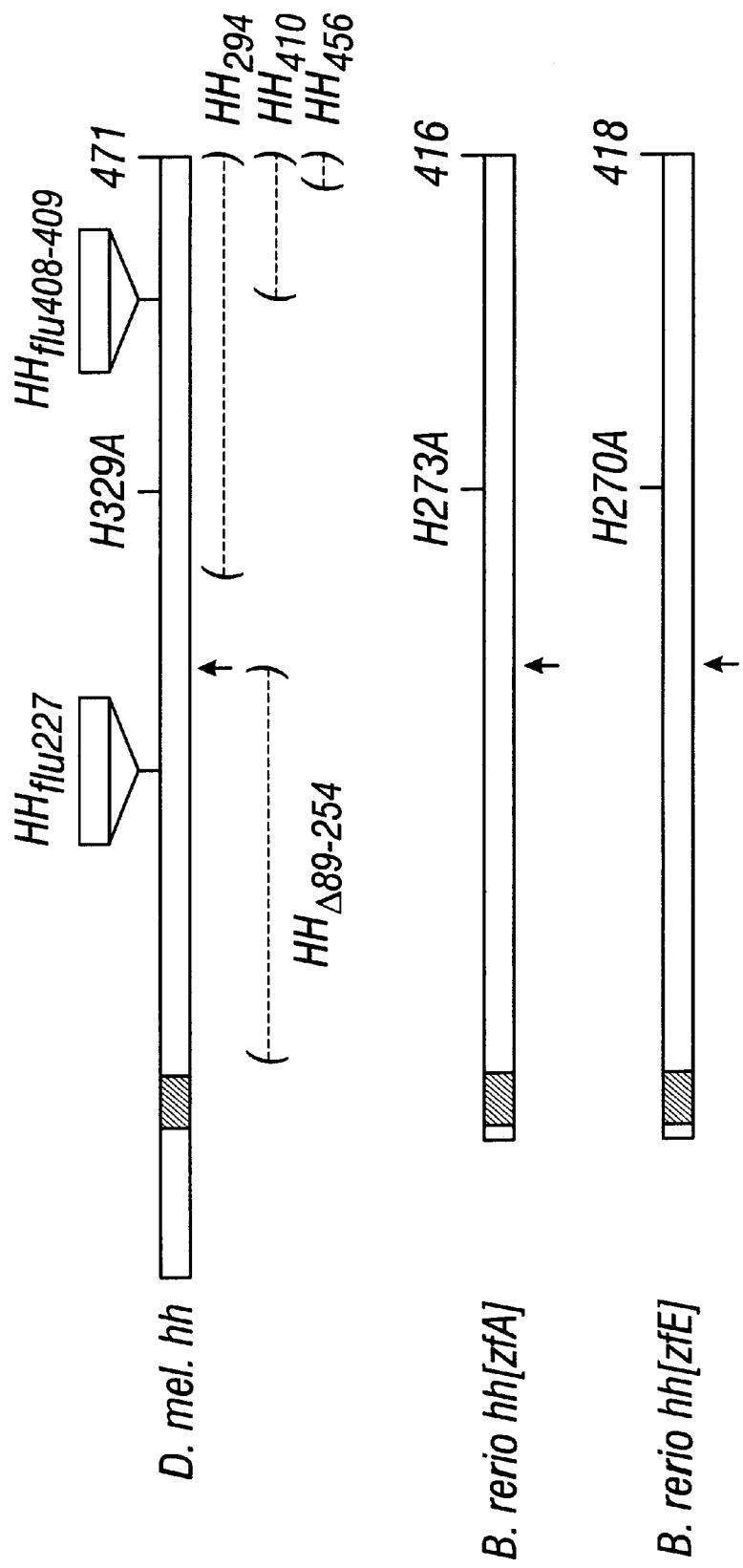

The hh gene has been broadly conserved in evolution, with single homologues unidentified in a wide variety of invertebrate species and multiple distinct homologues in each of several vertebrate species (Y. Echelard et al., *Cell* 75: 1417, 1993; S. Krauss, et al., *Cell* 75: 1431, 1993; H. Roelink et al., *Cell*, supra). As seen in FIG. 2, all of these coding sequences contain an invariant histidine and other conserved residues at a position corresponding to H329 in the Drosophila protein. In addition, the protein encoded by at least one of the mouse genes appears to be processed in vivo to yield two smaller species in a manner resembling the in vivo processing of the Drosophila protein. To determine whether auto-proteolysis may also play a role in vertebrates we examined the behavior of proteins encoded by two distinct hh homologues from the zebrafish, twhh and shh. FIG. 4D demonstrates that when these sequences are translated in vitro, smaller species are generated whose relative masses sum to yield approximately the relative mass of the full length protein (lanes 1 and 3). As seen in lanes 2 and 4, this cleavage reaction is blocked by substitution of Ala codons for the His codons at positions corresponding to H329 in Drosophila (see FIG. 2). Vertebrate hh proteins thus appear to be processed by a similar mechanism as the Drosophila protein.

EXAMPLE 4

ROLE OF AUTO-PROTEOLYSIS IN EMBRYOS

Numerous functions for the hh gene have been described in Drosophila. At the morphological level these include a role in patterning of larval cuticular structures and adult structures such as the eye and appendages (C. N üsslein-Volhard and E. Wieschaus, *Nature* 287: 795, 1980; and J. Mohler, *Genetics* 120: 1061, 1988).; the mechanistic basis for thee morphological effects involves signaling for maintenance or induction of gene expression in embryos and imaginal discs (J. J. Lee, supra; T. Tabata and T. B. Kornberg, *Cell* 76: 89, 1994; and K. Basler and G. Struhl, *Nature* 368: 208, 1994). To ascertain the importance of auto-proteolysis for these functions, the H329A mutant gene under control of the hsp 70 promoter was introduced by P element-mediated transformation into the Drosophila germline. The hshh H329A construct was made identically to the hshh construct with the use of a hh ORF fragment containing the H329A mutation. Transgenic flies were generated from a $y^1$ $w^{1118}$ parental strain using standard methods of P element mediated transformation (A. C. Spradling and G. M. Rubin, *Science* 218: 341 1982). A line, HA3, carrying the hshh H329A P element on the second chromosome was maintained as a homozygous stock. To assay for expansion of wg stripes, embryos collected at 4 to 6 hours after egg laying (AEL) at 25° C. were subjected to the following heat shock protocols prior to fixation. Embryos receiving single shocks (10 or 30 minutes at 37° C.) were allowed to recover for 1 hour at 25° C. Embryos receiving double shocks (two 10 minute or two 30 minute shocks at 37° C.) were allowed to recover 90 minutes after the first shock and 40 minutes after the second (Both recoveries were at 25° C. The double 30 minute protocol was as previously described, (S. Krauss, supra). In situ hybridizations were performed as described (D. Tautz, *Chromosoma* 98: 81, 1989) using a wg specific probe (D. T. Chang et al., supra). Embryos assayed for cuticle phenotype were heat shocked 6 to 8 hours AEL for 30 minutes at 37° C., allowed to develop at 25° C. for 36 hours and then processed and mounted as described (M. Ashburner, *Drosophila. A Laboratory Manual*, Cold Spring Harbor Laboratory Press, New York, 1989). Immunolocalizations (single or double stains) were performed as described. With the use of affinity purified Ab1 or Ab2 for the primary antibody and alkaline phosphatase (AP) or horseradish peroxidase (HRP) conjugated anti rabbit or mouse IgG (Jackson Immunoresearch) for the secondary. Embryos from a hh$^{13E}$/TM3 ftz-lacZ (the balancer chromosome was from the Bloomington Stock Center, strain 3218) stock homozygous for the hh$^{13E}$ allele were identified by the lack of staining with an anti b-galactosidase antibody (Promega) in a double stain with Ab2 (FIG. 9, panel D). Staining in FIG. 9, panels B and C were performed formaldehyde fixed Canton-S embryos with the use of an AP conjugated anti-rabbit IgG secondary. Although standard formaldehyde fixation was generally used, heat and acid-formaldehyde fixation also gave similar results. GST fusion proteins containing either residues 83 to 160 or 300 to 391 from the Hh protein were expressed in *E. coli*, purified as recommended (F. M. Ausubel et al., supra), and used to immunize rabbits by standard methods. The antibodies were affinity purified on a column of His$_6$-U protein (Harlow and Lane, supra) linked to Affi-Gel 10 beads (Bio-Rad). The purification was performed as described (Harlow and Lane, supra) except that the acid and base elutions contained 10 percent dioxane. Biotinylated hh antibodies were prepared by purifying the rabbit antisera over a protein A column, followed by biotinylation with the use of the Immunoprobe biotinylation kit (Sigma). Immunoprecipitations were performed as described (Harlow and Lane, supra) with the use of cold RIPA lysis buffer containing 0.25 mM PMSF and 5 mM EDTA for tissue homogenization. Lysates were pre-cleared twice with pre-immune rabbit serum plus protein A beads (Gibco BRL). Affinity purified antibodies or pre-immune serum was then added, and the immunoprecipitation was performed with protein A beads, with the use of NP-40 lysis buffer for the washes.

Figure 5A:
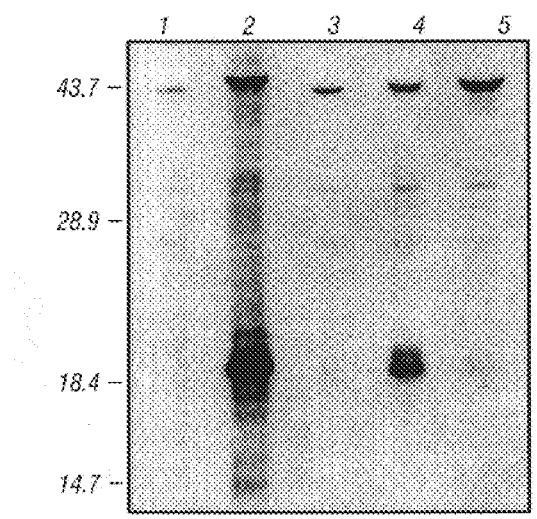
FIG. 5 shows immunoblots showing heat shock induced expression of wild type and H329A mutant hh proteins in Drosophilia embryos (A) and (B) are immunoblots developed using Ab1 and Ab2 antibodies, respectively. Lanes 1 and 6, induced untransfected S2 cells; lanes 2 and 7, transfected S2 cells induced to express hh; lanes 3 and 8, heat shocked wild-type embryos; lanes 4 and 9, heat shocked hshh embryos; lanes 5 and 10, heat shocked hshh H329A embryos.

FIGS. 5(A) and (B) are immunoblots developed with the use of Ab1 and Ab2 antibodies respectively. Lanes 1 and 6, induced untransfected S2 cells; lanes 2 and 7, transfected S2 cells induced to express hh; lanes 3 and 8, heat shocked wild-type embryos; lanes 4 and 9, heat shocked hshh embryos; lanes 5 and 10, heat shocked hshh H329A embryos. In heat shocked hshh embryos, the wild-type Hh protein is both induced and properly processed to generate the U, N C and C* species seen in other expression contexts. In contrast, the H329A is induced but not appreciably processed in hshh H329A embryos (the low levels of processed species in lanes 5 and 10 are probably from endogenous hh expression since they are seen at identical levels in heat shocked wild-type embryos in lanes 3 and 8).

Figure 5B:
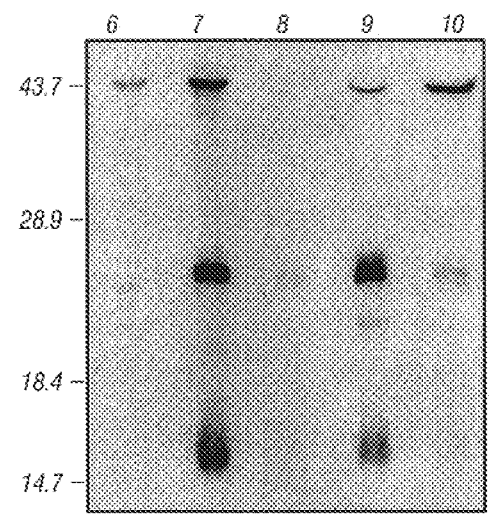

FIG. 5 shows that heat shock induction results in the formation of an abundant species that corresponds to U based on its mobility and its interaction with Ab1 and Ab2 (lanes 5 and 10). In contrast, induction of wild type hh protein using a similar construct resulted in similar levels of the N and C processed products (lanes 4 and 9), with very little uncleaved U. Thus, as observed in vitro and in S2 cells, the H329A mutation in embryos appears to greatly reduce the efficiency of auto-proteolytic cleavage of the hh protein.

Figure 6A:
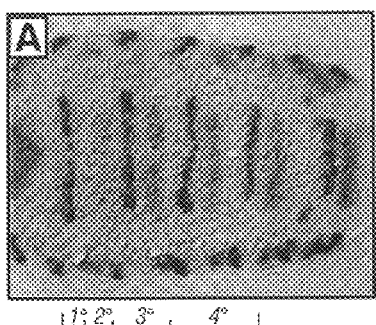
FIG. 6 shows in situ hybridization showing the embryonic effects of ubiquitously expressed wild type and H329A hh proteins.
Figure 6B:
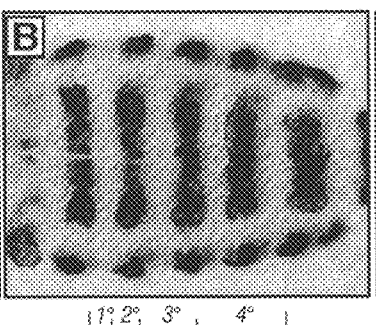
Figure 6C:
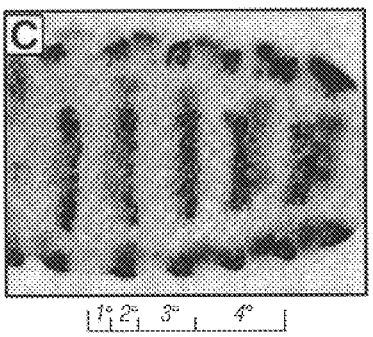
Figure 6D:
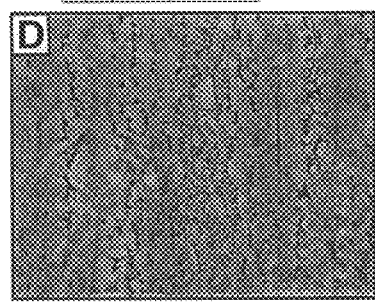
Figure 6E:
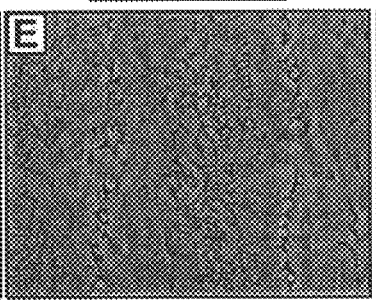

In FIG. 6, the embryonic distribution of wingless (wg) RNA as revealed by in situ hybridization is shown in FIG. 6(A) wild-type (homozygous $y^1$ $w^{1118}$), (B) hshh, and (C) hshh H329A embryos that were exposed to two 10 minute heat shocks separated by a 90-minute recovery period. Wild-type embryos showed little change in wg expression, whereas the wild-type protein and, to a lesser extent, the H329A protein each induced ectopic wg expression (Table 1). Panels (D), (E), and (F) show the dorsal surfaces of $y^1$ $w^{1118}$, hshh, and hshh H329A larvae, respectively, at the level of the fourth abdominal segment. These larvae were shocked for 30 minutes as embryos and allowed to complete embryogenesis. Cuticle cell types (1°, 2°, 3°, and 4°) are labeled as described (J. Heemskerk and S. DiNardo, *Cell* 76: 449, 1994). Note the expansion of 2° cell types (naked cuticle) at the expense of 3° and some 4° types in the hshh embryo (E) under conditions where the phenotype of hshh H329A embryos (F) is identical to that of control embryos (D).

Perhaps the earliest known requirement for Hh protein is in maintenance of an adjacent stripe of wingless (wg) gene expression in each embryonic segment (A. Martinez Arias, et al., *Development* 103: 157, 1988; and S. DiNardo, et al, Nature 332: 604, 1988). This requirement is deduced from the loss of wg expression when hh function is absent; in addition, the ubiquitous expression of wild-type Hh protein induces expansion of the domain of wg gene expression (P. W. Ingham, Nature 366: 560, 1993). The effects of the H329A mutation upon wg expansion were examined by heat shocking embryos carrying the H329A mutant construct in parallel with embryos containing the wild-type construct. Although the H329A mutant protein is able to induce some expansion of the wg domain, the efficiency of this activity is impaired relative to that of the wild-type protein (FIGS. 6, B and C; Table 1). The difference in efficiency ranges nearly as high as threefold depending upon the heat shock regime, and these results suggest that auto-proteolysis of the Hh protein is important for optimal activity in embryonic signaling to induce wg expression.

TABLE 1

Wild-type and mutant hh activity in embryonic induction of wg expression*

| | minutes of heat shock | | | |
|---|---|---|---|---|
| | 10 | 30 | 10/10 | 30/30 |
| hshh | 1.0 ± 0.3 (93) | 1.5 ± 0.6 (120) | 2.9 ± 0.3 (41) | 2.8 ± 0.4 (54) |
| hshh H329A | 0.7 ± 0.5 (190) | 0.9 ± 0.4 (111) | 1.1 ± 0.4 (145) | 1.9 ± 0.5 (93) |

*Expansion of wg expression beyond wild-type controls is given as average number of cell diameters ± standard deviation with number of embryos scored in parentheses.

Figure 6F:
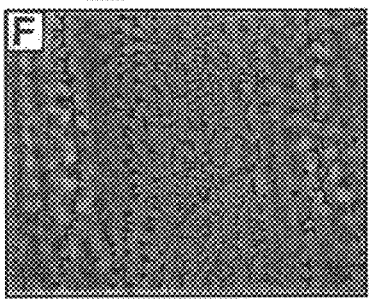

The effects of Hh protein on the patterning of cuticular structures are most clearly visible on the dorsal surface of the larva, where four distinctive cell types can be identified in each parasegment. These cell types have been designated 1°, 2°,3°, and 4°, from anterior to posterior, with hh transcription occurring in precursors of the 1° cells (J. Heemskerk and S. DiNardo, supra). Differentiation of the first three cell types was shown to be dependent upon hh gene function, and it has been proposed that the fates of these cells are determined by the concentration of Hh protein, with highest concentrations producing the 1° fate, intermediate concentrations producing the 2° fate, and the lowest concentrations producing the 3° fate (J. Heemskerk and S. DiNardo, supra). This proposal was supported by observations that the most anterior cell types display the greatest sensitivity to a reduction of hh expression, and that all of the 3° and some of the 4° bristles are replaced by naked cuticle characteristic of the more anterior 2° cell type when hh is expressed ubiquitously at high levels. We have reproduced suppression 3° and some 4° fates by heat shock induction of embryos that carry our wild-type construct (FIG. 6E), but find that the H329A mutant is unable to alter cell fates in the dorsal cuticle of the larva (FIG. 6F). Auto-proteolysis, or perhaps some other function blocked by the 11329A mutation, thus appears to be essential for the patterning influence of Hh protein upon the dorsal cuticle.

EXAMPLE 5

EFFECTS OF THE H329A MUTATION UPON SIGNALING IN IMAGINAL DISCS

Studies of H329A mutant protein were extended to the function to the patterning of adult structures and signaling within imaginal discs. In the eye imaginal disc hh function is required for appropriate development of pattern (J. Mohler, Genetics 120: 1061, 1988; J. J. Lee, supra; and J. Mohler and K. Vani, supra) and more recently has been shown to control progression of a wave of differentiation via induction of decapentaplegic (dpp) gene expression in the morphogenetic furrow of the eye (U. Heberlein, et al., Cell 75: 913 1993; and C. Ma, et al., Cell 75: 927, 1993). In leg and wing discs, ectopic expression of hh has also been shown to yield pattern duplications and defects and is associated with induction of ectopic expression of other signaling molecules normally expressed in a zone along the anterior/posterior compartment boundary (T. Tabata and T. B. Kornberg, Cell 76: 89, 1994; and K. Basler and G. Struhl, Nature 368: 208, 1994).

For studies of signaling in imaginal discs, a thermal cycler was utilized to subject larvae carrying heat shock-inducible hh constructs to successive rounds of heat shock and recovery. The effects of temperature cycling upon expression of dpp and wg in imaginal discs was examined by monitoring β-galactosidase expression from a reporter gene carrying dpp promoter sequences or from an enhancer detector P element inserted in the wg gene. In FIG. 7, X-gal staining was used to follow expression of wg FIG. 7 (A-C) or dpp FIG. 7 (D-L) in imaginal discs of late third-instar larvae that carry wg-lacZ or dpp-lacZ reporter genes. Leg (A-F), wing (G-I) and eye-antennal discs (J-L) from control larvae (A, D, G, J), larvae carrying the hshh transgene (B, E, H, K) and larvae carrying the hshh H329A transgene (C, F, I, L) are displayed. In all panels anterior is to the left. Arrows highlight the following features: an ectopic patch of dpp expression in the anterior compartment of wing discs in hshh H329A larvae (I); and an ectopic band of dpp expression in eye portion of the eye-antennal disc anterior to the morphogenetic furrow (marked by the other band of dpp expression more posteriorly) in hshh larvae (K). Expansion into the anterior compartment of wg expression in leg discs, and dpp expression in leg and wing discs in hshh larvae is similar to that described for the ectopic expression of hh. Morphological changes in the anterior compartment of leg (B and E) and wing discs (H) were also as described (K. Basler and G. Struhl, supra). In contrast, discs from hshh H329A and control larvae showed very little change in wg and dpp expression, even under prolonged heat shock conditions and morphological changes were never observed. (M-O) The eye phenotypes of adult control (M), hshh (N) and hshh H329A (O) flies that were shocked during larval development in a manner similar to that of the imaginal disc experiments above. Duplicated eye structures were observed in hshh flies, but never in hshh H329A flies. The arrow in (N) points to a thin strip of cuticle between the two eye structures. Other deformities were also seen in hshh flies (for example, compare the thorax in N to M).

Virgin female flies from the homozygous lines hshh (D. T. Chang et al., Development, 1994, in press), hshh H329A, and $y^1$ $w^{1118}$ were crossed to males from the homozygous BS3.0 line (bearing a P element dpp reporter construct on the 2nd chromosome, referred to as dpp-lacZ) (R. K. Blackman, et al., Development 111: 657, 1991) or the line y; Sco/CyO, enlacZll.:wg (bearing a wg reporter P element enhancer trap on a second chromosome balancer; called wg-lacZ) (J. A. Kassis, et al., Proc. Natl. Acad. Sci. U.S.A. 89: 1919, 1992). Progeny were grown at 25° C. in aerated 0.5-ml microcentrifuge tubes containing yeast paste until the late second instar or early third instar stage of larval development. The larvae were then cycled continuously at 37° C. for 30 minutes followed by 25° C. for 90 minutes in a Perkin-Elmer thermal cycler until they reached the late third instar stage. They were subsequently dissected and stained with X-gal as described (M. Ashburner, supra) or allowed to grow to adulthood for phenotypic analysis.

As shown in FIG. 7A, wg expression normally occurs in a ventral sector of the leg disc along the anterior/posterior compartment boundary while dpp is expressed in the dorsal portion of the disc along this boundary (FIG. 7D). Although thermal cycling of larvae carrying the wild-type hh gene produced abnormal leg disc morphology and extensive ectopic expression of both target genes, as previously reported for ectopic hh expression (FIGS. 7B and E), the H329A construct produced little if any detectable difference in these patterns of expression (FIGS. 7, C and F). Ectopic hh expression in the wing disc also leads to morphological changes and expanded expression of dpp (compare FIGS. 7, G and H), but the H329A construct produced only an occasional small patch of anterior ectopic expression (FIG. 7I).

Ubiquitous expression of wild-type hh also leads to ectopic expression of dpp in the eye-antennal disc (compare FIGS. 7, J and K). In the antennal portion of this disc the expansion of dpp expression resembles that observed in leg discs. In the eye portion of the disc dpp expression is observed at its normal location in the furrow; however, ectopic expression also occurs in the form of a second dorso-ventral band at a location somewhat anterior to the furrow, thus giving the appearance of an eye disc with two morphogenetic furrows (FIG. 7K). Indeed, in adults derived from temperature-cycled larvae that carry the wild-type hh construct, an apparently duplicated eye structure such as that in FIG. 7N can be observed, with two eye structures separated by a thin strip of cuticle (arrow). The H329A mutant protein, in contrast, did not induce expansion of dpp expression in either portion of the eye-antennal disc (FIG. 7L), and does not induce eye duplications or cuticle defects in the adult (FIG. 7O).

The experiments described thus far comprise multiple series of larvae subjected to two days of thermal cycling followed by immediate dissection for analysis of imaginal structures or further incubation at constant temperature for analysis of adult structures. Although the H329A protein appeared to have little activity in these experiments, the small patch of ectopic dpp expression induced in the wing disc (FIG. 7I, arrow) suggested that some residual activity remained. This suggestion was borne out in a similar experiment involving three days of cycling prior to dissection: the H329A protein clearly displayed some dpp-inducing activity in this experiment, presumably as a result of the higher amounts of protein that accumulated during the longer cycling period. The wing in particular, but also other imaginal discs, displayed low and variable amounts of ectopic dpp expression. This expression in all cases was far less extensive than that observed for the wild-type construct examined in parallel; furthermore, morphological deformations of the imaginal discs, although quite common with the wild-type protein, were extremely rare with the H329A protein. Although its potency is greatly reduced relative to wild-type, the H329A protein retained at least some activity in early embryonic and imaginal disc induction of wg and dpp expression; in contrast, even under heat shock conditions far more severe than those required for effects by the wild-type protein, the H329A mutant remained completely inert with respect to the re-specification of cell fates in the dorsal cuticle of the larva.

EXAMPLE 6

DIFFERENTIAL RELEASE OF N AND C INTO CULTURED CELL SUPERNATANTS

Figure 8A:
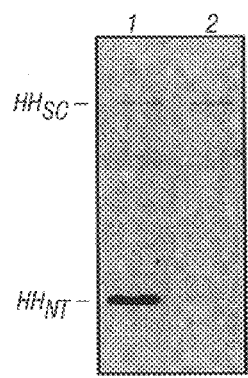
FIGS. 8(A) and (B) are immunoblots of cell pellets (lane 1) or supernatants (lane 2) from transfected S2 cell cultures expressing HH protein, developed with Ab1 (A) and Ab2 (B). Samples in each lane were from the same volume of resuspended total culture. Whereas N remained mostly associated with the cell pellet (compare lanes 1 and 2 in A)., C was nearly quantitatively released into the supernatant (compare lanes 1 and 2 in B). U displayed partitioning properties in between those of N and C (A and B). (C) demonstrates the heparin binding activity of various HH protein species generated by in vitro translations with microsomes (38). Samples were: total translation mix (lane 1); supernatant after incubation with heparin agarose or agarose (control) beads (lanes 2 and 4); and material eluted from heparin agarose or agarose beads after washing (lanes 3 and 5). F, U, $N_{SS}$ and N fragments are depleted from reactions incubated with heparin agarose but not agarose beads (compare lanes 2 and 4 to 1), and the same species subsequently can be eluted from the heparin agarose but not the agarose beads (compare lanes 3 and 5 with lane 1).
Figure 8B:
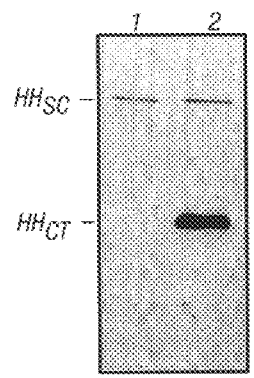

A puzzling feature of hh function is its apparent short-range action in settings such as embryonic and imaginal disc signaling to wg and dpp, and longer-range action in other settings, such as patterning of the dorsal larval cuticle. These observations and the existence of two major protein products in vivo prompted us to look for differences in the solubility or diffusibility of N and C expressed in S2 cultured cells. FIGS. 8(A) and (B) are immunoblots of cell pellets (lane 1) or supernatants (lane 2) from transfected S2 cell cultures expressing Hh protein, developed with Ab1 (A) and Ab2 (B). Samples in each lane were from the same volume of resuspended total culture. Whereas N remained mostly associated with the cell pellet (compare lanes 1 and 2 in A), C was nearly quantitatively released into the supernatant (compare lanes 1and 2 in B). U displayed partitioning properties in between those of N and C (A and B). (8C) demonstrates the heparin binding activity of various Hh protein species generated by in vitro translations with microsomes. Samples were: total translation mix (lane 1); supernatant after incubation with heparin agarose or agarose (control) beads (lanes 2 and 4); and material eluted from heparin agarose or agarose beads after washing (lanes 3 and 5). F, U, $N_{SS}$ and N fragments are depleted from reactions incubated with heparin agarose but not agarose beads (compare lanes 2 and 4 to 1), and the same species subsequently can be eluted from the heparin agarose but not the agarose beads (compare lanes 3 and 5 with lane 1). FIGS. 8, A and B indeed show that these proteins behave differently, with most of the N fragment remaining cell-associated and all, or nearly all, of C being released into the culture supernatant.

Figure 8C:
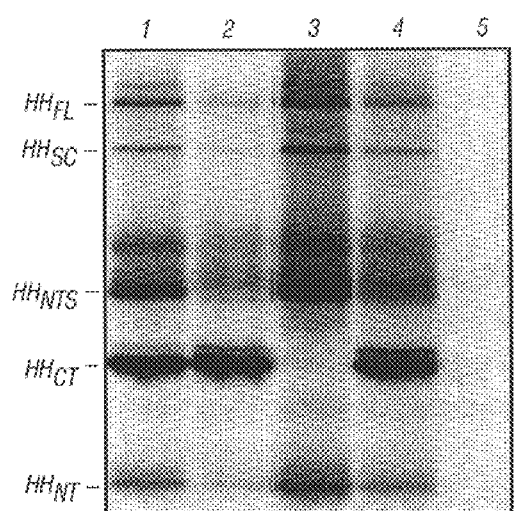

One possible explanation for this differential behavior might be association of the N fragment with extracellular matrix proteins on the surfaces of the S2 cells. Accordingly, the relative affinity of these two proteins for heparin agarose was examined, since heparin binding is a common property of proteins that associate with the extracellular matrix. Given the obvious difficulty in obtaining soluble N from cultured cells, in vitro translation in the presence of microsomes was used to generate soluble, labelled N and C. As shown in FIG. 8C, N but not C is depleted from these translation extracts by treatment with heparin agarose beads, while treatment with unmodified agarose beads did not deplete either fragment. Furthermore, N but not C was retained upon the heparin agarose beads upon extensive washing with a solution that contains 0.1% Triton X-100 and 150 mM NaCl; in contrast, neither fragment was retained by unmodified agarose. N, but not C, binds tightly to heparin, and this behavior suggests that the low concentration of N released into culture supernatants may be the result of binding to the extracellular matrix. Another mechanism that might contribute to the differential release of N and C into culture supernatant would be the expression in S2 cells of a receptor for N but not for C. Our current data can not distinguish these possibilities.

EXAMPLE 7

DISTINCT EMBRYONIC LOCALIZATIONS OF N AND C

The differential release of N and C into cultured cell supernatants suggested the possibility that these fragments might also be differentially localized in embryos. Previously reported hh protein localizations utilized either antibodies specific for N epitopes or antibodies unable to distinguish between N and C. FIG. 9 shows the differential localizations of N and C in embryos by in situ localization of the hh transcript. FIG. 9(A) is shown in comparison to the distribution of N and C epitopes detected with Ab1 and Ab2 in panels (9B) and (9C), respectively. Note that the distribution of N and C epitopes span approximately one-third and one-half of each segmental unit respectively, while the transcript is limited to approximately one-quarter of each unit. In (9D), the localization of C epitopes in embryos homozygous for the hh$^{13E}$ allele is detected with the use of Ab2. C epitopes in this mutant, which displays impaired auto-proteolytic activity are more restricted, and resemble the wild-type localization of N. Homozygous hh$^{13E}$ embryos were identified by loss of a marked balancer from a heterozygous parent stock. All embryos are at mid to late stage 9 (extended germ-band).

FIG. 9B shows in accordance with these reports, Ab1, which is specific for N epitopes, reveals a segmentally localized distribution that is slightly broader than that of the hh transcript at the same stage (FIG. 9A). Also consistent with these reports, we observed that N epitopes at later stages accumulate in large punctate structures. Our analysis here concentrates on the earlier stage, when antibody staining is weaker but before formation of the invaginations and grooves that later crease the epidermis and thereby complicate the interpretation. Ab2 was also utilized to detect C-specific epitopes with a variety of fixation and staining procedures. Although detection of C epitopes above background is more difficult than for N, we consistently observed a segmentally modulated pattern, albeit with a broader distribution than N (FIG. 9C). This localization is also distinctive in that C epitopes at early or late stages are not found in the punctate structures characteristic of N.

The hh$^{13E}$ mutation encodes a prematurely truncated protein that is missing 15 residues normally present at the COOH-terminus. Because this protein displays a much reduced efficiency in auto-proteolysis the distribution of C in this mutant background was examined. FIG. 9D shows that C epitopes in a homozygous hh$^{13E}$ embryo (identified by absence of a marked balancer) are distributed in a much tighter segmental pattern than in wild-type. This localization resembles that of N, and we thus conclude that the broad distribution of C epitopes normally seen is altered in hh$^{13E}$ by retention of the uncleaved precursor near the site of synthesis.

EXAMPLE 8

THE ROLE OF AUTO-PROTEOLYSIS IN BIOGENESIS OF ACTIVE HEDGEHOG PROTEIN

In addition to signal cleavage, the hh protein undergoes auto-proteolysis at an internal site to generate the predominant protein species observed in vivo. All or most of the amino acid residues required for this auto-proteolysis function map to C, the carboxy-terminal product of this internal cleavage. In an effort to determine the importance of auto-proteolysis for function, we introduced a single residue mutation (H329A) that blocks auto-proteolysis of the hh protein in vitro and demonstrated that both processing and function of this protein is impaired in vivo. Since similar levels of induced protein were detected from a strain carrying the wild-type construct or from several strains carrying independent insertions of the mutant construct (FIG. 5), the impaired function of the H329A protein relative to wild-type is not the result of reduced levels of expression. Further evidence in support of a role for auto-proteolysis derives from the effect of the hh$^{13E}$ mutation, which reduces but does not eliminate auto-proteolysis of the hh protein in vitro (FIG. 4). Correspondingly, the hh$^{13E}$ mutation is associated with a phenotype of intermediate strength in vivo (J. Mohler, supra).

Curiously, the H329A Hh protein appears to retain weak activity in embryonic signaling to induce ectopic wg expression and, to a lesser degree, can function in imaginal disc signaling for induction of ectopic wg and dpp expression. In contrast to its retention of at least some signaling functions in embryonic and imaginal tissues, the H329 protein is completely inert when assayed for the ability to reprogram cell fates in the dorsal cuticle of the larva.

Figure 10A:
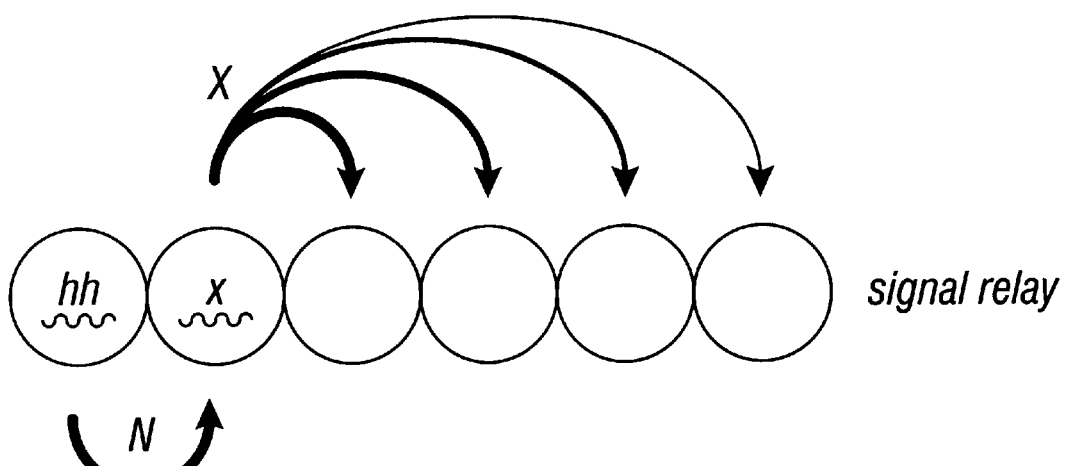
In FIG. 10(A), the long-range effects of hh signaling are achieved indirectly through short-range induction of a second signaling molecule (X). Based on its biochemical properties and its restricted tissue localization, N is presumed to represent the active short-range signal while the role of C would be limited to supplying the catalytic machinery required for biogenesis of N. In (B), the long- and short-range signaling functions of hh are supplied by the N and C proteins derived by internal auto-proteolysis of the U precursor. N is implicated in short-range signaling by retention near its cellular site of synthesis, while C is less restricted in its distribution and would execute long-range signaling functions. In both models, auto-proteolysis is required to generate fully active signaling proteins.
Figure 10B:
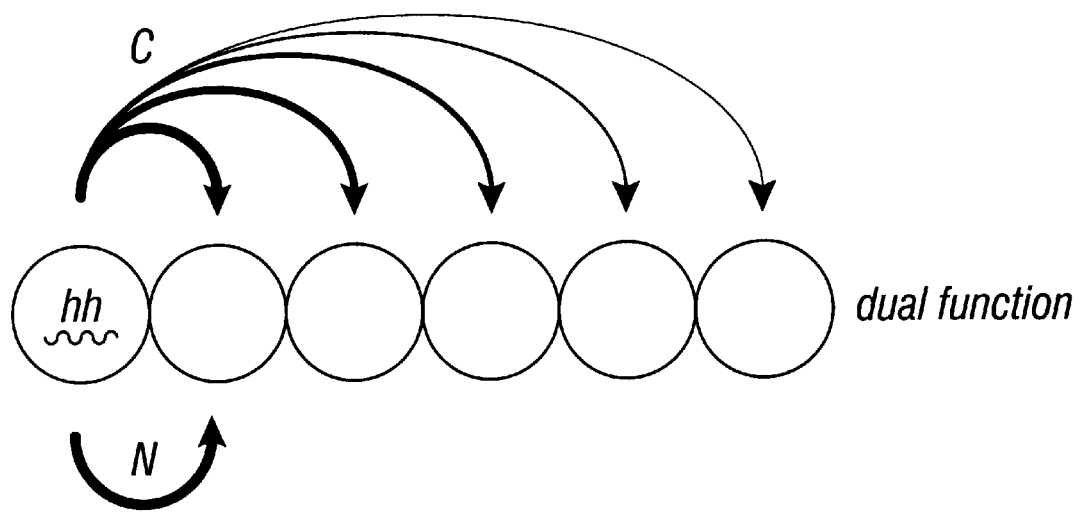
FIG. 10 shows a signal relay versus dual function models for hh protein action.
FIGS. 10C and D show an immunoblot of the N fragment synthesized from a wild type construct (C) or a construct lacking the C domain (D).

The assays in which the H329A protein is active or partially active involve short-range signaling that normally occurs across one or at most several cell diameters; in contrast, the H329A protein fails to exert any effect upon patterning of the dorsal cuticle, a long-range activity that normally operates across most of the segment. Previous proposals to account for long-range patterning activities have suggested that hh expression induces other signaling molecules which are then responsible for executing the patterning functions (the signal relay model; see FIG. 10A). FIG. 10 shows a signal relay versus dual function models for hh protein action. In FIG. 10(A), the long-range effects of hh signaling are achieved indirectly through short-range induction of a second signaling molecule (X). Based on its biochemical properties and its restricted tissue localization, N is presumed to represent the active short-range signal while the role of C would be limited to supplying the catalytic machinery required for biogenesis of N. In (10B), the long- and short-range signaling functions of hh are supplied by the N and C proteins derived by internal auto-proteolysis of the U precursor. N is implicated in short-range signaling by retention near its cellular site of synthesis, while C is less restricted in its distribution and would execute long-range signaling functions. In both models, auto-proteolysis is required to generate fully active signaling proteins. See text for further discussion.

These proposals seek to maintain a consistent mode of hedgehog action by rationalizing the apparent long-range activities of hh products as indirect consequences of short-range signaling. Based on the distribution observed, the active molecule in this model might be N and the role of C would then be limited to supplying the catalytic machinery required for biogenesis of N.

Our evidence suggests an alternative model, the dual function model (FIG. 10B), in which long- and short-range activities of the hh protein might be executed by N and C, the two predominant forms of the molecule observed in vivo. The nearly quantitative release of C fragment into the culture medium of hh-expressing S2 cells and its broad, though segmentally modulated distribution within embryos suggests that C might execute or contribute to long-range signaling functions. The N fragment, on the other hand, predominantly remains associated with the expressing S2 cells and also binds to heparin, which suggests a possible association with the extracellular matrix. These properties and the segmentally restricted embryonic distribution of N are suggestive of a role in the execution of short-range hh signaling activities. Since the vertebrate Hh proteins we tested also appear to be auto-processed and also carry predicted heparin binding sites just carboxy-terminal to their signal sequences (H. Roelink et al., supra), many aspects of the dual function model discussed here in the context of Drosophila development may also apply to hh protein function in vertebrate development.

Execution of short-range functions by N would be consistent with the observation that the H329A mutant protein has at least partial function in signaling for the induction of wg and dpp, since this mutation does not alter residues located in the amino-terminal portion of the protein that normally would give rise to N. The uncleaved H329A protein thus would carry all the residues that normally interact with a presumed receptor for N, although there might be some effect on the affinity of the interaction due to the presence of carboxy-terminal sequences, thus accounting for the decreased potency of the H329A protein. Alternatively, the partial function of H329A protein may derive from an extremely small fraction of protein that appears to be cleaved, a very faint band with identical mobility to C appears in in vitro translations with the H329A protein (FIG. 4, lane 3). Execution of long-range functions by C is also consistent with our observations because long-range signaling might require the release of the C fragment or otherwise require the H329 residue for some function other than for cleavage.

When N is synthesized from a native construct (wild type hh), it remains primarily cell-associated (FIG. 10C), however, N generated from a truncated construct in cultured cells predominantly enters the culture medium (FIG. 10D) (For constructs, see Porter, et al., *Nature*, 374:363, 1995). These results further confirm that autoprocessing by fragment C may regulate the degree of N association with the cell surface and therefore its range of action.

EXAMPLE 9

ISOLATION OF HEDGEHOG HOMOLOGUES

The mouse and human hh-like sequences were isolated by polymerase chain reaction (PCR) using primers degenerate for all possible coding combinations of the sequences underlined in FIG. 1 of Chang, et al., (*Development*, 120: 1994). PCR amplifications contained from 100 $\mu$g to 2 $\mu$g genomic DNA (depending upon the genome size of the species), 2 $\mu$M of each primer, 200 $\mu$M dNTPs (Pharmacia), 1×reaction buffer (Boehringer-Mannheim) and 2.5 units Taq polymerase (Boehringer-Mannheim) in 50 $\mu$l reactions. Amplification was as follows: 94° C. 5 min, addition of Taq polymerase at 75° C., followed by 94° C. 1 min, 52° C. 1.5 min and 72° C. 1 min for 30 cycles and a final extension of 72° C. for 5 min. All PCR products were cloned into pBluescript (Stratagene) prior to sequence determination.

Mouse clones obtained in this manner contained 144 bases of sequence between the primer ends and were labelled with [$\alpha^{-32}$P]dATP and used for high stringency screens of mouse cDNA libraries made from whole 8.5 dpc embryonic RNA and from 14.5 dpc embryonic brain in the λZAP vector (a gift from A. Lanahan). Several clones corresponding to Hhg-1 were isolated and the largest, 2629 bp in length (pDTC8.0), was chosen for sequence analysis using dideoxy chain termination (Sanger, et al., 1977) and Sequenase v2.0 (US Biochemicals). Compressions were resolved by using 7-deaza- guanosine (US Biochemicals). Sequence analysis made use of the Geneworks 2.0 (IntelliGenctics) and MacVector 3.5 (IBI) software packages.

One of the three mouse clones, Hhg-1, when used as a probe, yielded a 2.0 kb clone from a 8.5 dpc mouse embryonic cDNA library and a 2.7 kb clone from a 14.5 dpc embryonic cDNA library. The 2.7 kb cDNA appears to represent a nearly full length mRNA because it corresponds to a 2.7 kb band detected by hybridization on a Northern blot. The largest methionine-initiated open reading frame within this cDNA encompasses 437 codons, and is preceded by one in frame upstream stop codon. Sequence comparisons indicate that the protein encoded by Hhg-1 is identical to the independently characterized mouse Shh (Echelard, et al., *Cell*, 75:1417–1430, 1993) except for an arginine to lysine difference at residue 122. Hhg-1 also corresponds closely to the rat vhh-1 gene (97% amino acid identity; Roelink, et al., *Cell*, 76:761–775, 1994), the chicken Sonic hedgehog (81% identity; Riddle, et al., *Cell*, 75:1401–1416, 1993) and Shh from the zebrafish (68% identity; Krauss, et al., *Cell*, 75:1431–1444, 1993; Roelink, et al., *Cell*, 76:761–775, 1994). The PCR-generated fragments Hhg-2 and Hhg-3 appear to correspond to the Indian and Desert classes of mouse hedgehog genes, respectively (Echelard, et al., *Cell*, 75:1417–1430, 1993).

Alignment of the Hhg-1 open reading frame with the two Drosophila hh sequences showed that all three proteins contain hydrophobic amino acid sequences near their amino-termini; the hydrophobic stretches within the *D. melanogaster* protein (residues 64 to 83) and within the mouse protein are known to act efficiently as signal sequences for cleavage (Lee, et al, *Cell*, 71:33–50, 1992). Both Drosophila signal sequences are unusual in their internal locations, while the hydrophobic stretch of the mouse gene occurs at the extreme amino-terminus, a more conventional location for cleaved signal sequences. Although portions of sequence N-terminal to the Drosophila signal sequences are conserved, suggesting a functional role, the mouse gene lacks this region.

The overall level of amino acid identity between Hhg-1 and hh carboxy-terminal to the signal sequences is 46%. A closer examination shows that the amino terminal portion, from residues 25 to 187, displays 69% identity, while remaining residues in the carboxy-terminal portion display a much lower 31% identity. Like hh, the Hhg-1 coding sequence is divided into three exons, and the boundaries of these exons are at the same positions within coding sequence as those of the three Drosophila hh exons. Curiously, the boundary between coding sequences of the second and third exons occurs near the transition from high to low levels of overall sequence conservation. The coincidence of these two boundaries suggests a possible demarcation of functional domains within these proteins. This location within Hhg-1 coding sequence also coincides approximately with the site of a presumed proteolytic cleavage.

EXAMPLE 10

HUMAN CLONING OF hh GENES

Partial sequence for two human hh genes has been obtained by DNA sequencing of clones derived by PCR amplification from genomic DNA with hh-specific degenerate primers as outlined in Chang, et al., (*Development*, 120:3339, 1994) and EXAMPLE 9 (FIGS. 11A and B). More extensive screening by the same approach, either with the same primers or with other primers from the hh coding region or with the human hh fragments seen in FIGS. 11A and B, is expected to yield at the least a third gene, and possibly more, since at least three genes are found in the mouse. These segments of human hh genes can be used to obtain full coding sequences for human proteins by the following cloning method commonly used by those of skill in the art and which are extensively described in the literature.

For example, ready-made cDNA libraries or RNAs from a variety of human sources, including various fetal stages and organs (from abortuses) and specific infant or adult organs (from pathological or autopsy specimens), are being tested for the presence of hh sequences by PCR or RT-PCR using the primers described in Chang, et al., supra, and other primers derived directly from the sequence of the human fragments. Ready-made libraries containing hh sequences are being screened directly and, where necessary, new libraries are being constructed by standard methods from RNA sources containing hh sequences. The probe for these screens is a mixture of all the distinct human hh fragments. Sequences of cDNA clones can then be determined. Most clones containing the probe sequences, which are located in the N region, will also include a full C coding region since standard methods of library construction result in cDNA clones that are most complete at their 3' ends. All full length hh-coding sequences obtained previously in vertebrates and invertebrates contain N and C sequences encoded in a single RNA. Screening is continued until complete open reading frames that correspond to all of the fragments of human hh genes are obtained. Specifically, $1.2 \times 10^6$ clones from a human fetal brain library (Stratagene, La Jolla, Calif.) was screened using a mixture of the two human hh fragments (FIGS. 11A and B) as probes. Twenty-nine clones were identified as specifically hybridizing with these probes.

Second, the RNA sources identified as containing hh sequences can be used as templates from anchored PCR (also referred to in the literature as RACE, for rapid amplification of cDNA ends). Briefly, this method provides a means to isolate further mRNA sequence in either the 5' or 3' direction provided that sequence is known from an internal starting point. Anchored PCR can also be used to isolate sequences from cDNA library.

Third, genomic libraries can be screened with the probes described in the first technique. Where necessary, human hh exons and coding sequences are being identified by hybridization to previously isolated human and mouse coding sequences by sequence determination, and by exon-trapping methods to identify all hh coding sequences within genomic clones; these coding sequences can be "stitched" together by standard recombinant DNA methods to generate complete hh open reading frames.

Figure 12A:
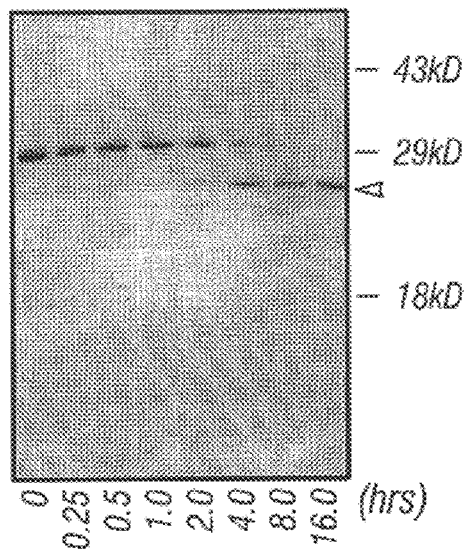
FIG. 12A and B show in vitro cleavage reactions of a Drosophila hh protein produced in E. coli and purified to homogeneity.
Figure 12B:
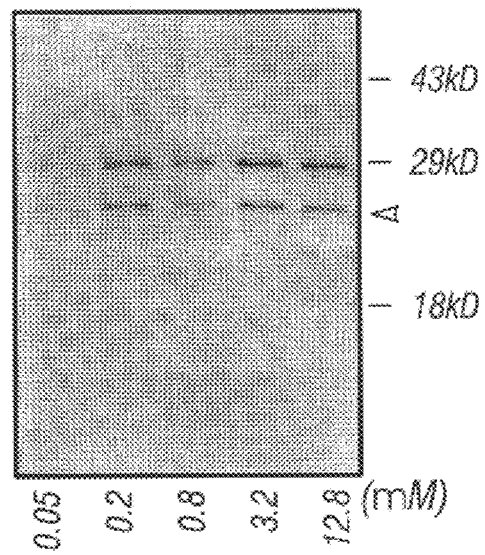
FIG. 12, Panel A shows a time course of cleavage after initiation by addition of DTT. Panel B shows incubations of concentrations ranging over three order of magnitude for a fixed time period (four hours), with no difference in the extent of conversion to the cleaved form. Panel C shows the sequence around the cleavage site as determined by amino-terminal sequence of the cleaved fragment C. The cleavage site is denoted by the arrow, and the actual residues sequenced by Edman degradation of the C fragment are underlined. Panel C also shows an alignment of all published vertebrate hh sequences plus some of unpublished sequences from fish and Xenopus. The sequences shown correspond to the region of Drosophila hh where the cleavage occurs, and demonstrates the absolute conservation of the Gly-Cys-Phe sequence at the site of cleavage. Panel D shows a SDS-PAGE gel loaded with in vitro transcription/translation reactions as described in the previous Examples, using various hh genes as templates. dhh is Drosophila, twhh and zfshh are the twiggy-winkle and sonic hh genes of the zebrafish, and mshh is the shh/Hgh-1/vhh-1 gene of the mouse. Panel E shows that Edman degradation of the C fragments releases $^{35}$S counts on the first but not subsequent rounds for all these proteins, indicating that the site of autoproteolytic cleavage for all of these hh proteins is the amide bond to the amino-terminal side of the Cys residue that forms the center of the conserved Gly-Cys-Phe sequence highlighted in panel C.
Figure 12D:
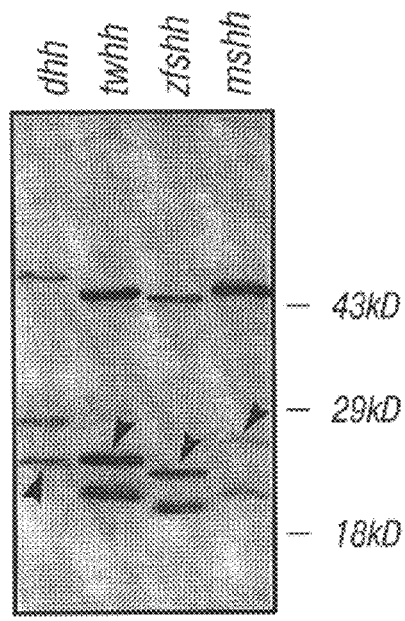

FIGS. 12A and B show in vitro cleavage reactions of a Drosophila hh protein produced in *E. coli* and purified to homogeneity. This protein has residues 89–254 deleted, rendering it more soluble and easier to purify. It also contains a $His_6$ purification tag appended to the N-terminus. Autoproteolysis of this protein is triggered by the addition of reducing agents (DTT), and the resulting product corresponds to the C fragment identified in vivo. FIG. 12, Panel A shows a time course of cleavage after initiation by addition of DTT. Panel B shows incubations of concentrations ranging over three order of magnitude for a fixed time period (four hours), with no difference in the extent of conversion to the cleaved form. This concentration-independent rate of cleavage indicates an intramolecular mechanism of cleavage. Panel C shows the sequence around the cleavage site as determined by amino-terminal sequence of the cleaved fragment C. The cleavage site is denoted by the arrow, and the actual residues sequenced by Edman degradation of the C fragment are underlined. Panel C also shows an alignment of all published vertebrate hh sequences plus some of unpublished sequences from fish and Xenopus. The sequences shown correspond to the region of Drosophila hh where the cleavage occurs, and demonstrates the absolute conservation of the Gly-Cys-Phe sequence at the site of cleavage. Panel D shows a SDS-PAGE gel loaded with in vitro transcription/translation reactions as described in the previous Examples, using various hh genes as templates. dhh is Drosophila, twhh and zfshh are the twiggy-winkle and sonic hh genes of the zebrafish, and mshh is the shh/Hgh-1/vhh-1 gene of the mouse. The translation mix included $^{35}S$-labelled cysteine, used to visualize the resulting products by autoradiography. Note that each gene give a larger product (the precursor or U) and two smaller products of cleavage (N and C). The larger species is C for each of the vertebrate genes, whereas the Drosophila N is larger than C due to the presence of ~60 residues occurring amino-terminal to the signal sequence that are present in the vertebrate open reading frame. This panel shows that vertebrate hh proteins are processed similarly to the Drosophila protein. Panel E shows that Edman degradation of the C fragments releases $^{35}S$ counts on the first but not subsequent rounds for all these proteins, indicating that the site of autoproteolytic cleavage for all of these hh proteins is the amide bond to the amino-terminal side of the Cys residue that forms the center of the conserved Gly-Cys-Phe sequence highlighted in panel C. This is a generalizable approach to establish the composition of protein fragments from any other hh family members.

EXAMPLE 11

DIFFERENTIAL EXPRESSION OF TWO hh GENES IN AXIAL MESODERM AND IN NEURAL PROGENITORS

Partial sequences corresponding to five distinct zebrafish hh-like genes were isolated and the complete coding sequences for two of these genes were obtained from an embryonic cDNA library. One of these two sequences is identical to that of the zebrafish nhh-I gene (Roelink, et al., *Cell*, 76:761, 1994), and appears to correspond to the shh gene reported by Krauss, et al., (*Cell*, 75:1431, 1993) (See FIG. 13 description); the other gene, tiggy-winkle (Potter, B., The Tale of Mrs. Tiggy-Winkle, *The Penguin Group*, London, 1905), represents a novel vertebrate hh. Coding sequences for both are shown in alignment to mouse and chicken sequences of the sonic/vhh-1 class (FIG. 13b). Like other vertebrate hh homologues, the twhh and shh proteins contain an amino-terminal stretch of hydrophobic residues. These residues function as signal sequences since cleavage is observed when coding sequences are translated in the presence of microsomoses; vertebrate hh genes thus appear to encode secreted proteins, as previously reported for Drosophila hh (Kimmel C. B. & Warga, R. M., *Developmental Biology*, 124:269–280, 1987; Warga, R. M., & Kimmel, C. B., *Development*, 108:569–580, 1990).

The first four sequences were isolated from zebrafish genomic DNA (a gift from J. Pellegrino) using degenerate primers in polymerase chain reactions as described (Chang, et al., supra). twhh and shh clones were isolated from a 20–28 hour cDNA library (a gift from R. Riggleman, K. Helde, D. Grunwald and J. Pellegrino) using the first three sequences as probes. The translational reading frames for twhh and shh were closed 12 and 16 codons, respectively, upstream of the putative initiating methionine.

FIG. 13 shows the predicted amino acid sequences are shown in single letter code. 13(*a*) shows sequences common to five distinct hh-like genes arc shown with a dot indicating identity with the corresponding residue of zebrafish twiggy-winkle (twhh; Potter 1905; supra), hh[zfB] and hh[zfC] is more diverged and appears to represent a novel class. 13(*b*) shows amino acid sequences of twhh and shh are aligned to those of the soniclvhh-1 class from chick and mouse (Riddle, et al., *Cell*, 75:1401–1416, 1993; Chang, D. T., et al., *Development*, supra; Echelard, Y., et al., *Cell*, 75:1431–1444, 1993). Zebrafish sonic hedgehog (shh) is identical in sequence to z-vhh-1 reported by Roelink, et al., *Cell*, 76761–775, 1994. Based on expression and extensive sequence identity throughout most of the coding region, vhh-1 and the sonic sequence reported here probably correspond to shh of Krauss, et al., *Cell*, 75:1431–1444, 1993, diverges dramatically throughout a 26 residue stretch near the carboxy-terminus. Rat vhh-1/sonic hh (Roelink, et al., supra.) was excluded in this alignment because of its 97% sequence identity to the predicted mouse protein. Residues identical in all four sequences are boxed, and a dash indicates a gap in the alignment. The arrow indicates the predicted signal sequence cleavage site (von Heijine, G. , *Nucleic Acids Res.*, 14, 4683–4690, 1986) for twhh. The amino-terminal hydrophobic stretch common to all four hh genes is shaded. 13(c) shows percent identity of residues carboxy-terminal to the hydrophobic region.

FIG. 14 shows a comparative expression of twhh, shh, and pax-2 during zebrafish embryogenesis. Whole mount in situ hybridizations on 0–36 hour embryos were performed using a modification of the procedure of Tautz and Pfeifle, *Chronosoma*, 98:81–85, 1989, with antisense probes. Transcript localization is revealed by the purple product of an alkaline phosphatase enzymatic reaction. Staging of the embryos is according to Westerfield, M., (*The Zebrafish Book*, University of Oregon Press, Eugene, 1993). Transcripts were visualized by in situ hybridization to whole embryos. (a, b) twhh expression in a single late shield stage embryo. (a) Dorsal view, animal pole is to the top. The triangular shape of expression is characteristic of axial mesoderm-forming cells of the hypoblast (Statchel, S. E., et al, *Development*, 117:1261–1274, 1993). (b) Lateral view: the thicker layer of cells on the left (dorsal) side of the embryo is the embryonic shield; the two arrows indicate the twhh-expressing hypoblast cells and the non-expressing epiblast. Anterior is to the left in all subsequent embryos. Dorsal is to the top in all lateral views. (c, d) A single embryo at the end of gastrulation (100% epiboly) with twhh-expressing cells. (d) Caudal-dorsal view. Note the wide patch of stain in the presumptive tailbud which narrows anteriorly. (e, j) Early somitogenesis (11.5 hour, 3–4 somite) embryos, optic vesicles have not begun to evaginate from the wall of the diencephalon. (e, h, k) Lateral views of developing brain. (f, i, l) Dorsal views of developing brain. (e, f, g) Localization of twhh-expressing in a single row of cells that will form the flood plate. The arrowhead marks a parch of twhh-expressing cells lateral to the tailbud. (h, i, j) Localization of shh. shh is also expressed strongly in the protuberance. (j) Lateral view of the developing tail. shh is also expressed strongly in the protuberance. (j) Lateral view of developing tail. shh is expressed in cells that will form both floor plate and notochord. (k, l, m) Localization of pax-2 during early optic vesicle formation; (m) also shows twhh expression. (k) 12 hour (4–5 somites) embryo. (l) 12.5 hour (5–6 somites) embryo. Expression of pax-2 in the developing optic vesicle is in a gradient away from the protuberance. Note the expression of pax-2 (asterisk) at the future midbrain-hindbrain border. (m) twhh (arrow) and pax-2 expression in a 6–7 somite (13 hour) stage embryo. Note differential expression of twhh in ventral neural keel (corresponding to neural tube in other vertebrates). (n–s) Embryos at end of somitogenesis (22–24 hours). (n, o, p) Localization of twhh. (n, o) Developing brain. Note isolated groups of cells staining in the diencephalon (filled triangles) and the protuberance (arrowhead), and floor plate expression underlying the midbrain and hindbrain. The floor plate expression is contiguous caudally along the axis. (n) Lateral view. (o) Dorsal view. (p) Lateral view of tail. Expression is restricted to the floor plate. (q, r, s) Localization of shh. (q, r) Developing brain (q) Lateral view. pax-2 expression in the otic vesicle is indicated. (r) Dorsal view. Expression in the protuberance (arrowhead) and in the neural keel. (s) Lateral view of tail. Expression is strongest in the floor plate, but contrary to the report of Krauss, et al., supra., is still also in the notochord. Abbreviations: white e—epiblast; h—hypoblast; tb—tailbud; p—protuberance; c—eye; ov—optic vesicle; ot—otic vesicle; fp—floor plate; nc—notochord; asterisk—midbrain-hindbrain boundary or pax-2-labeled prospective midbrain-hindbrain boundary; t—telencephalon.

Figures 14A, 14B, 14C, 14D:
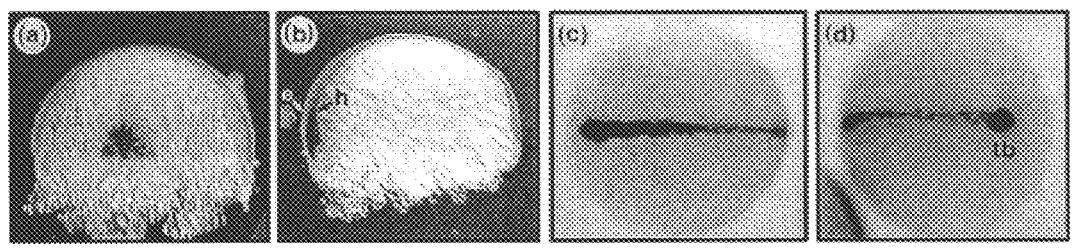
FIG. 14 shows a comparative expression of twhh, shh, and pax-2 during zebrafish embryogenesis.
Figures 14E, 14F, 14G:
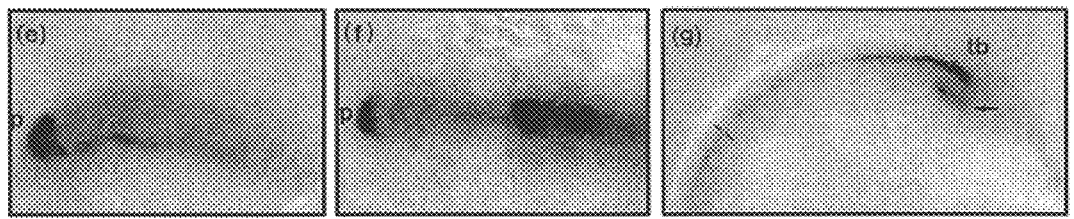
Figure 14H:
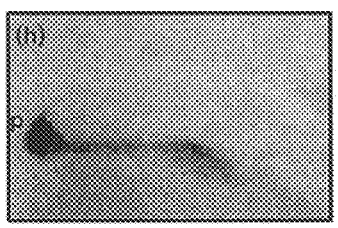
Figure 14I:
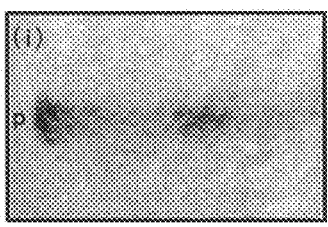
Figure 14J:
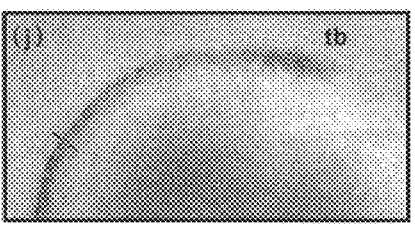

Comparison of twhh and shh expression patterns (Krauss, et al, supra), reveals that both gene are predominantly expressed in midline structures, albeit with notable differences in regard to timing, rostra-caudal extent, and tissue restriction. Expression of twhh is first detected during gastrulation in the dorsal mesoderm (FIGS. 14a, b); this expression occurs in a band corresponding to a subset of the embryonic shield, a structure, analogous to Spemann's organizer in Xenopus (Stachel, et al., *Dev.*, 117:1261–1274, 1993, and reference therein; Ho., R., *Seminars in Developmental Biology*, pg.3, 1992). In concert with the movements of convergence and extension, this band of twhh expression shortens along the equatorial plane and extends along the incipient embryonic axis until, by the end of gastrulation, expression occurs throughout the entire axis (FIGS. 14c,d). Early in somitogenesis, twhh RNA is found restricted to presumptive ventral neural tissue along the entire body (FIGS. 14e, f, g), the only exception being cells in and near the tailbud (FIG. 14g). In contrast to the neural restriction of twhh, shh is localized both to presumptive neural and notochordal cells (FIG. 14j).

As somitogenesis proceeds, ventral midline expression of shh and twhh is reduced in most of the prospective forebrain, but remains strong in an anterior patch of midline cells within the floor of the prospective diencephalon (FIGS. 14e, f, for twhh; FIGS. h, i for shh), This patch later will give rise to the protuberance (Schmitt, E. A. and Dowling, J. D., *J Comp. Neur.*, 344:532–542, 1994), an anterior extension of the diencephalon. This structure, which is medial and just rostral to the developing optic stalks, is the site we propose as the focus of early patterning activity for the developing eyes (see below). By the end of somitogenesis, both twhh and shh are strongly expressed in the floor plate (FIGS. 14p, s), although shh transcripts remain detectable in the notochord at this stage and at 36 hours of development (FIG. 14s; later stage not shown). At 28 hours, twhh transcripts are also found in a small cluster of cells within the first gill arch (not shown), as also reported for shh at 33 hours of development (Krauss, et al., supra).

Differences between twhh and shh expression are apparent from the beginning of gastrulation, since twhh RNA can be detected as early as the shield stage while shh is first detected later, at about 60% epiboly (not shown; (Krauss, et al., supra). In addition, twhh transcripts are restricted to neural tissues early in development, and are never detected in the notochord (compare FIG. 14g to FIG. 14j). Later differences in expression include differential rostra-caudal restriction within the diencephalon and midbrain and weaker and more restricted expression of twhh in the protuberance (compare FIGS. 14n and 14q), such that the later domain of twhh expression in the brain appears to constitute a subset of the shh domain. In addition, shh but not twhh is expressed in the developing fin bud (Krauss, et al., supra). Comparison of shh and twhh expression patterns to this previously reported for hh homologues in zebrafish and other vertebrate species indicates that shh is the zebrafish homologue of the sonic/vhh-I class while twhh represents a novel class of vertebrate hh.

EXAMPLE 12

DEVELOPMENTAL CONSEQUENCES OF ECTOPIC hh EXPRESSION DURING ZEBRAFISH EMBRYOGENESIS

To gain insight into the potential roles of hh products in development, synthetic twhh and shh mRNA was injected into 1–8 cell embryos. This technique yields a mosaic but fairly uniform pattern of expression, as determined for the control mRNA encoding β-galactosidase (not shown). Uniformity of expression is in good agreement with fate mapping studies of the early zebrafish embryo (Kimmel & Warga, supra; Warga & Kimmel, supra; Heide, et al., Science, 265:517–520, 1994), which indicate that blastomeres undergo extensive cell mixing during the cleavages prior to gastrulation. We note that mosaicism of expression caused surprisingly little variation in the phenotypes of the hh injected embryos, possibly due to secretion of hh gene products.

Embryos injected with synthetic twhh or shh mRNA (hh RNA) exhibited numerous yet highly reproducible abnormalities in comparison to control embryos injected with lacZ mRNA. These abnormalities, discussed below, are primarily defects in the brain and eyes. Although the effects of ectopic twhh and shh expression were qualitatively similar, the incidence and severity were greater with twhh RNA (see text below, FIG. 15 and FIG. 16). The proteins encoded by these two genes have qualitatively similar biological activities, but apparent differences in potency.

FIG. 15 shows the effects of ectopic hh on zebrafish development. Wild type zebrafish, Danio rerio, Ekkwill Waterlife Resources) were maintained at 28.5° C., some embryos were then cultured overnight at RT. Zebrafish embryos were injected at the 1–8 cell stage with twhh, shh, or lacZRNA and examined at 28 h of development. (a–c) Dorsal view of the midbrain-hindbrain region; anterior is left. (a) lacZ. (b) twhh. (c) shh. (d–f) Frontal optical section of the forebrain region; anterior is up. (d) lacZ. (h) twhh. (f) shh. (g-1) Lateral view of the eye region; anterior is left. (g) lacZ. (h) twhh. (i) twhh. At levels caudal to the prospective brain, the notochord, somites, and neural keel formed by most hh-injected embryos appeared grossly normal except for an overall shortening and dorsal curvature of the axis. A minority of hh-injected embryos (15% are not shown) displayed partially bifurcated axes, containing duplicated axial mesoderm and parallel neural keels, each neural keel comprising ventral midline cells and some bilaterally symmetric lateral cells (not shown). Although we have not determined the primary cause of these axial defects, analysis of late gastrulation stage embryos suggests hat the bifurcation may result from difficulties in epiboly and convergence. Abbreviations: mv—mesencaphalic ventricle; rv—rhombencephalic rentricle; asterisk—midbrain-hindbrain boundary; ot—otic vesicle; v—third (diencephalic) ventricle; r—retina or retina-like structure; 1—lens or lens-like structure; pe—pigmented retinal epithelium.

Morphological defects in the brain and other rostral neural derivatives occur at high frequency in hh-injected embryos. The three ventricles of the fish brain normally apparent at 28 hours of development—the rhombencephalic, mesencephalic (FIG. 15a), and diencephalic (third ventricle; FIG. 15d)—are not formed in the brains of hh injectees (FIGS. 15b, c; FIGS. 15e, f)), despite the obvious presence of a lumen. The prominent construction normally present at the midbrain-hindbrain boundary also is absent (compare FIG. 15a to FIGS. 15b, c). Formation of this constriction requires function of pax-2 (Krauss, et al., Nature, 353:267–270, 1991; Krauss, et al., Nature, 360:87–89, 1992), which normally is expressed in a band at the midbrain-hindbrain boundary (Krauss, et al., supra; Krauss, et al., Development, 113:1193–1206, 1991) pax2 expression at this boundary is not disrupted by hh RNA injection, however, indicating that this phenotype does not result from disruption of rostra-caudal information.

Defects in eye development also occur at high frequency in embryos injected with hh RNA. Thus, while at 28 hours the normal zebrafish eye has a lens and a retina with pigmented epithelium (FIGS. 15d, g), hh-injected embryos usually fail to develop lenses and retinal pigmentation (FIGS. 15e, h). Eye duplications are also observed at low frequencies (FIG. 15i). The poorly developed eyes do not appear to result from a simple delay in development since pigmentation elsewhere in injected embryos appears in its normal time course. Examined at three days of development, the consequences of hh RNA injection include defects that range from complete absence of eyes to partially formed eyes lacing a ventral portion of the retina.

The eye phenotypes caused by hh RNA injection resemble those produced by treatment of zebrafish and Xenopus laevis embryos with retinoic acid. InXenopus, phenotypes range from reduction of the eye and absence of the lends to eyes with retinal folds (resembling duplicated dyes) and multiple small lenses (Manns, M. & Fritzsch, B., Neurosci. Lett., 127:150–154, 1991). In zebrafish, exposure to retinoic acid during gastrulation interferes with the formation of the eye (Holder, N. & Hill, J., Development, 113:1159–1170, 1991), while exposure during formation of the optic primordia induces formation of duplicated retinas and extra lenses (Hyatt, et al., Proc. Natl. Acad. Sci. USA, 89:8293–8297, 1992). Patterning effects of retinoic acid upon the developing chick limb appear to be mediated through ectopic activation of the endogenous sonic hh gene (Riddle, et al., supra), these results with ectopic hh expression suggest the possibility of a similar mechanism underlying the patterning effects of retinoid acid treatment in the vertebrate eye.

EXAMPLE 13 hh EXPRESSION IN THE OPTIC VESICLE SPECIFIES PROXIMAL FATES AT THE EXPENSE OF DISTAL FATES

Figure 14K:
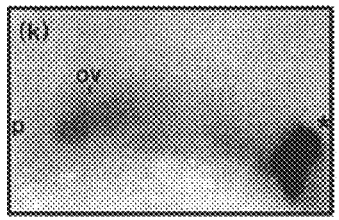
Figure 14L:
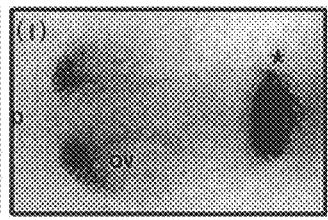
Figure 14M:
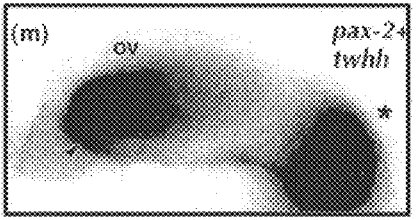

To further elucidate the role of hh in eye development we utilized pax-2 and pax-6 (Krauss, et al., EMBO J., 10:3609–3619, 1991; Pitischel, et al., Development, 114:643–651, 1992) were utilized as positional markers to examine the effects of ectopic hh expression on the optic vesicle. As the optic vesicle evaginates from the lateral walls of the zebrafish forebrain (Schmitt, E. A. & Dowling, J. D., J. Comp. Neur., 344:532–542, 1994),pax-2 is expressed in a gradient, with highest RNA levels in the anterior and ventral regions of the optic vesicle (Krauss, et al., supra; FIGS. 14k, l, m). Immediately adjacent to the maximum of this pax-2 expression gradient is the region of the diencephalon termed the protuberance (Schmitt & Dowling, supra), where both twhh and shh but not pax-2 are strongly expressed (FIGS. 14e, f, h, i, m). The concentration gradient of pax-2 expression in the eptic vesicle thus appears to incline downward from its maximum at a location adjacent to the site of twhh and shh expression in the protuberance. Superposition of developmental fate within the optic vesicle (Schmitt, et al., supra), upon the pattern of pax-2 expression suggests that the gradient of pax-2 RNA prefigures the future proximal/distal axis of the eye.

Ectopic hh alters the expression of pax-2, pax-6, and F-spondin. Zebrafish embryos were injected at the 1–8 cell stage with twhh or shh RNA and the pattern of pax-2, pax-6, or F-spondin expression was examined by whole mount in situ hybridization. Control embryos injected with lacZ RNA were performed in every case and displayed wild-type expression patterns. At embryo stage, the anterior-posterior axis of the optic vesicle corresponds to the future proximal-distal axis of the eye. During the next hour of development, the posterior edge of the optic vesicle will separate from the diencephalon (Schmitt and Dowling, *Comp. Neur.*, 344:532–542, 1994).

Injection of either hh RNA causes uniform initiation of pax-2 expression along both the proximal-distal and dorsal-ventral axes of the optic vesicle as it begins to evaginate. The ectopic pax-2 expression appears at the same time as normal pax-2 expression is initiated in the eye, and in some cases, is also seen in the diencephalon between the optic vesicles. At the end of somitogenesis, a time when pax-2 would normally be restricted to the optic stalk, pax-2 RNA in hh injected embryos is detected in all but the most distal portion of the optic vesicle.

The effects of ectopic hh on expression of pax-6, which encodes a transcription factor critical for eye development was also studied. At 22 hours of zebrafish development, pax-6 is normally expressed in the lens and in most of the distal part of the optic cup (Krauss, et al., supra; Puschel, et al., *Development*, 114:643–651, 1992). In hh-injected embryos, pax-6 is repressed in the optic vesicle, although many embryos retain pax-6 expression in the most distal cells. With regard to pax-2 and pax-6 as markers of positional identity, hh expression in the optic vesicle can be characterized as inducing proximal fates and repressing distal fates.

The distal part of the optic vesicle is the most refractory to hh-induced changes in both pax-2 and pax-6 gene expression. Due to a later rotation, this distal portion of the optic vesicle will give rise to the dorsal portion of the mature eye (Schmitt, et al., supra); interestingly, this is the portion of the eye that remains in 3-day old injected embryos with intermediate phenotypes (see above).

Lesions in the pax-6 gene have been assigned as the basis for the Aniridia (Ton, et al., *Cell*, 67:1059–1074, 1991; Glaser, et al., *Nat. Genetics*, 2:232–239,1992), Small eye (Hill, et al., *Nature*, 354:522–525, 1992), and eyeless mutations (Quiring, et al., *Science* 265:785–789, 1994), in humans, mice and Drosophila, respectively; pax-6 function thus appears to be critically required for eye development in Drosophila and mammals. As we argue here, hh-encoded activities also appear to play a role in vertebrate eye development, and this suggests a further molecular parallel between vertebrates and insects, since the role of hh in Drosophila eye development is well established (Mohler, et al., supra; Ma, et al., supra; Heberlein, et al., supra; Lee, et al., supra). The reciprocal and non-overlapping patterns of hh and pax-6 expression in the developing Drosophila eye (Ma, et al., supra; Quiring, et al., *Science*, 265:785–789, 1994), suggest the possibility of pax-6 repression by hh, but whether hh functions by similar mechanisms in vertebrate and Drosophila eye development is a questions that requires further investigation.

In mice, the dosage of pax-6 protein is crucial for normal eye development (Hill, et al., supra). Small eye heterozygotes develop an abnormally small lens (Hogan, et al., *J. Embryol. Exp. Morph.*, 97:95–110, 1986; Hogan, et al., *Development*, 103 Suppl., 115–119, 1988), as do hh-injected embryos with weaker phenotypes (FIG. 14*f*). Small eye homozygotes lacking lenses eventually generate and the animals lack eyes at birth (Hogan, et al., supra; Hogan, et al., supra), as do many of the hh-injected embryos at three days of development. These parallels suggest that many of the later eye defects observed in hh-injected zebrafish may be caused by partial or complete repression of pax-6 during eye development.

EXAMPLE 14

GENETIC ABLATION OF hh FOREBRAIN EXPRESSION CAUSES LOSS OF PROXIMAL FATES IN THE OPTIC VESICLE

The patterns of twhh and shh expression (FIG. 14) and the effects of ectopic hh expression (FIG. 15) are consistent with a normal role for shh and twhh in eye development. If hh activities indeed play a normal role in promoting proximal fates within the developing eye, removal of hh activities would be expected to result in a loss of proximal fates. In embryos homozygous for the cyclops mutation ventral neural structures fail to form and the developing eyes fuse at the midline, yielding an embryo with a single eye (Hatta, et al., *Nature*, 350:339–341, 1991). The missing ventral structures in cyclops mutants include the regions where we observe expression of twhh and shh, and we therefore examined the effects of the Cyclops mutation on hh expression. $cyc^{b16}$ (Hatta, et al., *Nature*, 350:339–341, 1991), heterozygous adults (a kind gift of R. Riggleman) were spawned and their offspring analyzed by whole mount in situ hybridization. Detection of pax-2 and either twhh or shh RNAs in embryos homozygous for the cyc mutation or their wild-type siblings. twhh RNA is only expressed in the presumptive tailbud (caret) of cyc embryos. As reported by Krauss, et al., *Cell*, supra, neural expression of shh is abolished in cyc embryos. Strong pax-2 expression was observed in the optic vesicles of wild-type embryos which is significantly reduced in cyc mutant embryos.

twhh RNA in Cyclops embryos is found only in a small patch of cells at the presumptive tailbud and neural expression was not detected at any later stage examined. Neural expression of shh is also lost in eye mutants, although expression in the notochord is reunited (Krauss, et al., supra; data not shown).

Since the eye mutation appears to ablate hh-expressing cells in the developing brain, this mutation can be used as a genetic tool to examine the requirement for hh function in eye development. liatta, et al., Hatta, et al., *Proc. Natl. Acad. Sci. USA*, 91:2061–2065, 1994), recently demonstrated that pax-6 expression is fused at the midline due to loss of ventral midline cells that normally do not express pax-6 and, in addition, pax-2 expression in the fused eye of eye mutant embryos is reduced. We extended these observations to an earlier stage when the optic vesicles first form and found that pax-2 expression is weak and fails to extend within the vesicles in eye mutants. In conjunction with the results of ectopic hh expression, these observations suggest that hh signaling that activity promotes and is required for the induction of proxima fates within the eye vesicle. In this model, we propose that the protuberance acts as a proximal patterning center for the developing zebrafish eye by providing a localized source of hh activity.

EXAMPLE 15 hh ACTIVITY VENTRALIZES THE DEVELOPING BRAIN

Previous work has established an important role of signals from the floor plate and notochord in ventral patterning of the neural tube (Jessell, T. M., & Dodd, J., *Cell*, 69:95–110, 1992). For example, Goulding, et al., *Development*, 117:1001–1016, 1993, recently demonstrated that notochord and floor plate grafts can repress the normal lateral expression of pax-6 in the neural tube. Other recent work has implicated hh activity in at least some aspects of ventral neural tube patterning (Echelard, et al., *Cell*, 75:1417–1430, 1993; Krauss, et al., supra; Roelink, et al, supra); consequently, we examined hh-injected embryos for effects on pax-6 expression in the brain.

In the zebrafish at 22 hours of development, pax-6 is expressed in dorso-lateral regions of the diencephalon and in a ventro-lateral domain of the hindbrain and spinal cord that excludes the floor plate and adjacent cells (Krauss, et al., supra; Puschel, et al., supra). This pattern of expression is reciprocal to that of both twhh and shh in the diencephalon (compare FIGS. 14q and 14i) and in the hindbrain. hh RNA injection caused repression of pax-6 in the more ventral domain in the diencephalon, while more dorsal expression persisted. In addition, pax-6 expression was significantly reduced ventrally in rhombomeres 1, 2, and 4 and, in some cases, was completely abolished in these rhombomeres. The repressing effect of ectopically expressed hh and pax-6 in normal embryos are due to repression of pax-6 by nearby hh expressing cells.

Since absence of pax-6 expression is a feature of the ventral midline, repression of pax-6 in lateral positions suggests ventralization. Consequently, twhh was injected into embryos for analysis of induction of a floor plate marker, F-spondin (Riddle, et al., supra). As described above, ectopic twhh induces F-spondin expression at more dorsal levels in the midbrain and anterior hindbrain. The effects of hh upon expression of both pax-6 and F-spondin indicate a ventralization of the brain. Adoption of ventral cell identity by lateral cells might explain their failure to form ventricles (FIGS. 15a–f).

The ventralizing activities of twhh confirm and extend those previously reported for shh/vhh-1 class genes of chicken, zebrafish, and rat (Echelard, et al., supra; Krauss, et al., supra; Roelink et al., supra). The early restriction of twhh to midline neural progenitors, however, suggests that it may play a specific role in the homeogentic mechanisms of floor plate maintenance and expansion (Placzek, et al., *Dev.*, 117:205–218, 1993). In the zebrafish, wild type cells in Cyclops hosts can contribute to and induce adjacent cells to form floor plate, but only when the transplanted cells populate the neural plate and not the notochord (Hatta, et al., *Nature*, 350:339–341, 1991). We have demonstrated that, in Cyclops mutants, midline expression of twhh is lost while shh expression is maintained in the notochord (FIG. 18; Krauss, et al., supra for shh); taken together, these results suggest that the homogenetic floor plate signal lost in the Cyclops mutant may be encoded by the twhh gene. In the chick and rat, the floor plate retains auto-inductive potential long after the loss of floor plate inducing properties by the notochord, despite continued expression of shh/vhh1 in the notochord (Roelink, et al., supra; Placzek, et al., supra; Yamada, et al., *Cell*, 73:673–686, 1993). Although no homologues of the twhh class have been reported in other vertebrates, expression of other hh homologues in patterns more like those of twhh might help explain these discrepancies.

EXAMPLE 16

TWO DISTINCT SIGNALING PROTEINS DERIVE FROM THE twhh-ENCODED PRECURSOR

Endogenous hh protein in Drosophila is found predominantly as an amino- and a carboxy-terminal fragment (N and C, respectively) derived by an internal auto-proteolytic cleavage of a larger precursor (U for uncleaved), which also occurs in vivo but at lower levels (Lee, et al., supra). Determinants within the amino-terminal domain appear not to be required for auto-proteolytic activity, whereas mutations affecting the carboxy-terminal domain can block auto-proteolysis and reduce activity in vivo (Lee, et al., supra). The auto-proteolysis is blocked by a substitution of alanine for the histidine normally present at position 329. This histidine is absolutely invariant in alignments of all known hh genes, and its sequence context suggests a catalytic role in auto-proteolysis (Lee, et al., supra).

Figure 17A:
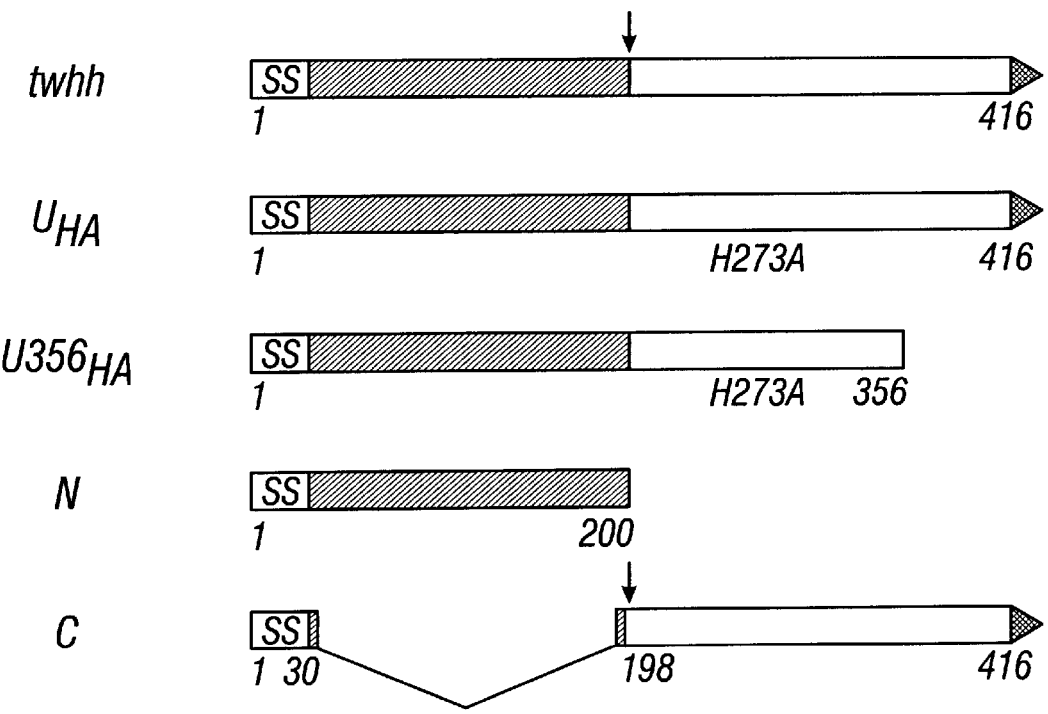
FIG. 17 shows zebrafish twiggy-winkle hedgehog derivatives. 17(a) Cartoons of various twhh open reading frames. SS (shaded) is the predicted N-terminal signal sequence for secretion of these proteins and encompasses the first 27 amino acids of each open reading frame. The arrow indicates the predicted internal site of auto-proteolytic cleavage. Amino acid residue numbers are according to FIG. 13b. The filled triangle denotes the normal termination codon for the twhh open reading frame. Construct $U_{HA}$ contains a mutation that blocks auto-proteolysis (the histidine at residue 273 is changed to an alanine; see Lee, J. J., et al., supra.).
Figure 17B:
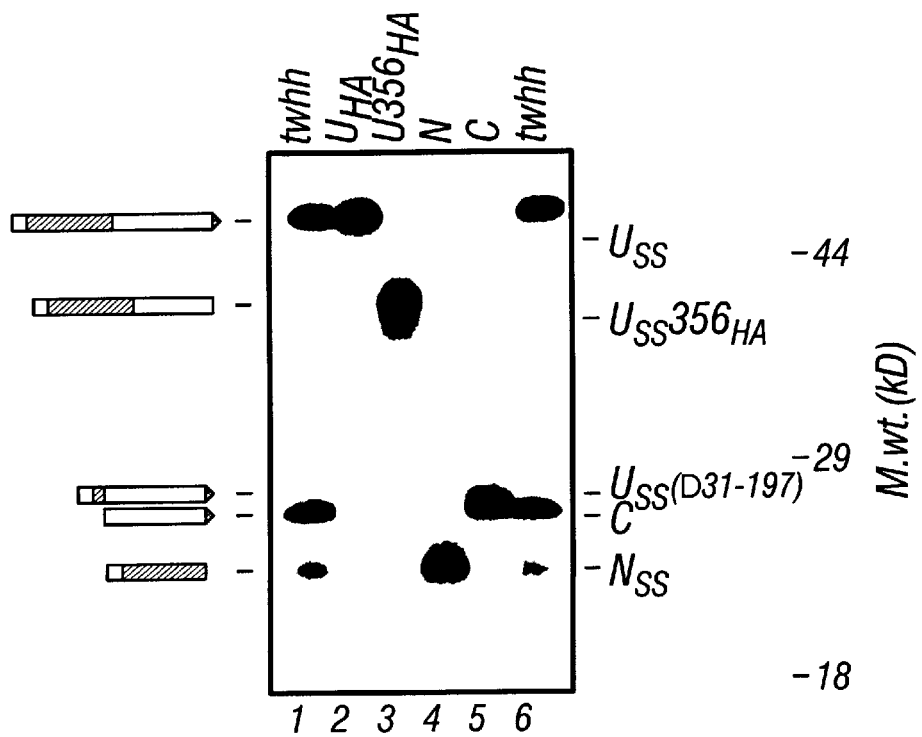

FIG. 17 shows zebrafish twiggy-winkle hedgehog derivatives. 17(a) Cartoons of various twhh open reading frames. SS (shaded) is the predicted N-terminal signal sequence for secretion of these proteins and encompasses the first 27 amino acids of each open reading frame. The arrow indicates the predicted internal site of auto-proteolytic cleavage. Amino acid residue numbers are according to FIG. 13b. The filled triangle denotes the normal termination codon for the twhh open reading frame. Construct $U_{HA}$ contains a mutation that blocks auto-proteolysis (the histidine at residue 273 is changed to an alanine; see Lee, J. J., et al., supra.). Construct $U356_{HA}$. A contains a stop codon in place of amino acid residue 357 as well as the H273A mutation in $U_{HA}$. Construct N encodes just the first 200 amino acids of twhh. Construct C has had the codons for residues 31–197 deleted. 17(b) shows in vitro translation of the expression constructs shown schematically in part a. Constructs were translated in vitro in the presence of $^{35}S$ methionine and analyzed by autoradiography after SDS-PAGE. The protein products are shown schematically to the left. Lanes 1 and 6: Auto-proteolysis of the full-length ($U_{SS}$) protein creates two fragments, an N-terminal fragment ($N_{SS}$) and a C-terminal fragment (C). Lane 2: Construct $U_{HA}$ only makes an uncleaved form of twhh protein that comigrates with $U_{SS}$ twhh via auto-cleavage. Lane 5: Construct C encodes processed and unprocessed forms which are visible as two bands migrating closely together. The bottom band is the C protein made from auto-proteolysis of the $U_{SS}$ (Δ31–197). All constructs were made by in vitro mutagenesis of expression construct T7TStwhh (see FIG. 15) using the method of RPCR. The sequence of all constructs were confirmed by dideoxy sequencing. In vitro translations were performed according to manufacturer's instructions (Promega).

The vertebrate hh proteins encoded by shh, twhh and mouse-shh/Hhg-1 also undergo auto-proteolysis to yield two smaller species from a single larger precursor (Lee, et al., supra; Chang, et al., supra; see lanes 1 and 6 in FIG. 17b). The invariant histidine to alanine mutation to generate a construct encoding a form of the twhh protein that is not auto-proteolytically cleaved ($U_{HA}$). We have also introduced a nonsense codon and deleted a segment of coding sequence to generate constructs that produce either the amino- or the carboxy-terminal domains of twhh (N and C, respectively; see lanes 4 and 5 in FIG. 17b); constructs are schematically diagrammed in FIG. 17a). To target these proteins to the secretory pathway, all constructs retained the normal twhh signal sequence.

Synthetic mRNAs transcribed from these constructs were injected to examine the role of processing and to assay the activities of individual protein fragments; the results are summarized in Table I and are based on the activities presented in FIG. 15. The most striking conclusion from these experiments is that N and C both exhibit activity, and that these activities are distinguishable. Thus, although both N and C are capable of ectopically activating pax-2 in the developing eye, thereby providing an internal injection control, only N was capable of efficiently repressing pax-6 (FIG. 16). Later effects on lens development were also more extreme for N, consistent with the role of pax-6 in lens development suggested by its mutant phenotypes in mice. (See Ton, C. C., et al., *Cell* 67:1059–1074, 1991; Glaser, T., etal., *Nat. Genetics* 2:232–239, 1992; Hill, R. E., et al., *Nature* 354:522–525, 1991; Hogan, B. L., et al., *J. Embryol. Exp. Morph.*, 97:95–110, 1986; and Hogan, B. L., et al., *Development*, 103Suppl.:115–119, 1988.)

In considering the activity of delta N–C, it is important to recognize the activity of endogenous hh genes in these experiments, which are inhibited by delta N–C and fragments thereof. (see Example 18 and FIG. 18 for further discussion)

The uncleaved $U_{HA}$ protein is only somewhat less active than C in inducing pax-2, but it also was not able to repress pax6 efficiently (FIG. 16). The latter is particularly notable since the $U_{HA}$ protein ($U356_{HA}$; see FIGS. 17a, b) has activities not significantly different from N (FIG. 16). Thus, in addition to carrying determinants important for autoproteolysis and pax-2induction, the C-terminus also contains a domain inhibitory to N-terminal function when in the context of the uncleaved hh protein. The C-terminus can also inhibit N action by an intermolecular mechanism (Lai, et al., supra). The existence of such an inhibitory domain in C suggests that if autoproteolysis can be modulated, such modulation might regulate the activity of hh in vivo. This possibility highlights the importance of ascertaining the processed state of hh proteins expressed in any particular patterning center to understand the potential hh activities generated.

EXAMPLE 17

DUAL ROLES OF hh SIGNALING PROTEINS IN EARLY EYE AND BRAIN PATTERNING

In understanding the normal roles of N and C in eye and brain patterning, the N and C derivatives of the Drosophila hh gene may offer some insight. The Drosophila N derivative is retained close to its embryonic site of synthesis in a segmentally striped pattern (Tabata and Kornberg, *Cell*, 76:89–102, 1994; Taylor, et al., *Mech. Dev.*, 42 89–96, 1993), is cell-associated when expressed in cultured cells, and is effectively bound by heparin agarose in vitro, suggesting the possibility of extracellular matrix association. The C-terminal fragment, in contrast, is not bound effectively by heparin agarose, is almost quantitatively released into the culture supernatant of expressing cultured cells, and is only diffusely localized in embryos. Although the activities of individual fragments have not been assayed, the biochemical differences and tissue distributions of Drosophila N and C may account for the short and long range nature of the functions associated with hh during Drosophila development.

Although the tissue distributions of zebrafish N and C are not known, their activities in ectopic expression assays are also suggestive of short- and long-range functions when considered in the context of normal expression patterns of hh, pax-2 and pax-6. The normal gradient ofpax-2 expression in the optic vesicle extends a substantial distance from its maximum adjacent to the site of hh expression in the protuberance; the ability of ectopic C to activate pax-2 therefore suggests that, consistent with the distribution of C in Drosophila, zebrafish C may carry out a long-range function. Repression of endogenous pax-6 expression, in contrast, appears to be a short-range function since pax-6 expression occurs close to endogenous hh expression. Efficient repression of pax-6 is an attribute of constructs producing N, and a short-range function for N would be consistent with the distribution of N in Drosophila.

Two types of hh-dependent activity have been reported for hh-transfected cultured cells. One is the apparent contact-dependent induction of floor plate markers (Roelink, H., et al., *Cell* 76:761–775, 1994); the second induction of sclerotome markers in presomitic mesoderm, is diffusible and acts at long-range.

EXAMPLE 18

CHARACTERIZATION OF XENOPUS hh

1. Materials and Methods cDNAs encoding full-length Xenopus hedgehogs, or encoding amino terminal or carboxy terminal domains linked to secretory leader sequences were transcribed in vitro to yield translatable messenger RNA. The synthetic messenger RNAs, and control mRNAs, were microinjected into the animal poles of cleavage stage Xenopus embryos, which were allowed to develop to the blastula stage, at which time the animal cap explants were prepared from the upper one fourth of the embryo. These blastula cap explants were then cultured in vitro in physiological saline in the presence or absence of the transforming growth factor beta family member, recombinant human activin A. All explants were allowed to develop until control embryos had grown to neurula stage, or to tadpole stage. Importantly, blastula caps left untreated differentiate from ectoderm into atypical epidermis. Blastula caps treated with activin differentiate into mesodermal and neural cell types. Thus, the question was whether hedgehog, or its proteolytic derivatives, would change the differentiation of cells away from becoming epidermis, and into another cell type. A second question was whether hedgehog can work with activin to alter the normal response of the tissue to either factor by itself.

Explants were then extracted to yield mRNA by methods commonly used by those of skill in the art, which was used as template with reverse transcriptase to yield cDNA. The cDNA was then used as template with various sets of primers for PCR for specific genes, reverse-transcriptase-polymerase chain reaction, or RT-PCR. This results in specific amplification of radioactive products which are diagnostic for the presence and level of the messenger RNAs which were present in the explants. Samples were separated on polyacrylamide gels, which were exposed to X-ray film to yield the bands shown in the figures. Thus, the darker bands correspond to a greater level of the specific mRNA.

Figure 18A:
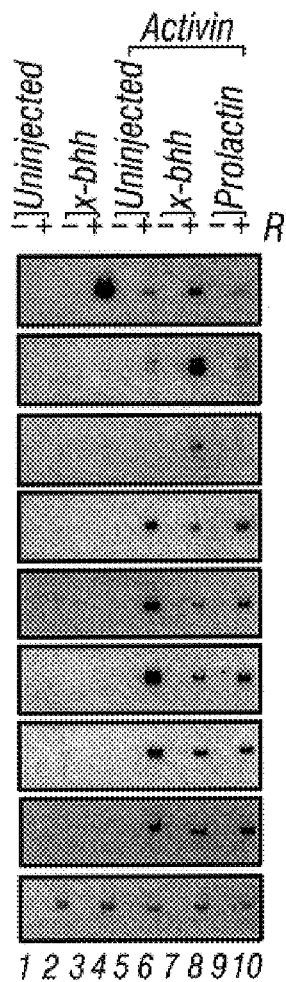

FIGS. 18A and B demonstrate that hedgehog induces pituitary and anterior brain genes, and can cooperate with activin or with neural inducers such as noggin and follistatin which are induced by activin to elevate expression of these genes in explanted embryonic tissue. All odd numbered lanes lack reverse transcriptase in the RT-PCR reaction and are negative controls. All even numbered lanes have this enzyme, and thus give specific bands to mRNA. In Panel A, Lanes 1–2 are control blastula caps, lanes 3–4 are Xenopus hedgehog-expressing blastula caps, lanes 5–6 are control blastula caps treated with activin, lanes 7–8 are hedgehog-expressing blastula caps treated with activin, and 9–10 are prolactin-expressing blastula caps treated with activin to serve as a control for simply expressing a secreted protein in the blastula cap. The primers used for the assay are shown to the left of each panel, i.e., XAG 1 is a cement gland marker, XANF1B is a pituitary marker, otx-A is an anterior brain marker, en-2 is a midbrain-hindbrain boundary marker, krox 20 is a rhombomere-specific hindbrain marker, HIHbox 6 is a posterior hindbrain marker, NCAM is a general neural marker, activin is a control for mesoderm induction, and elongation factor is a positive control to shown that all even numbered lanes did in fact have cDNA present.

The panel labelled XANF1B detects a pituitary gene. Lane 4 (panel A) shows that hedgehog induces this pituitary marker, and thus likely pituitary cell types, in blastula cap explants (see also FIG. 20, lane 6, for a stronger signal showing this), when compared to control explants in the absence of hedgehog (lane 2), which do not express this gene.

Lane 6 shows that explants treated with activin, in the absence of hedgehog, also express the pituitary gene. Lane 8 shows that explants treated with both hedgehog, and with activin, give highest levels of the pituitary gene. Lane 10 proves that this effect of hedgehog is specific, since prolactin, another secreted protein, does not lead to this elevated level of pituitary gene.

The panel labelled OTX-A detects this anterior brain gene. Lane 4 (and 6 in FIG. 20) shows that hedgehog can induce this neural-specific gene. Lane 8 shows that the level of this neural gene is highest in tissue treated with both activin and hedgehog, relative to hedgehog alone (lane 4), or activin along (lane 6), and control explants do not express this gene (lane 2). Again, this effect is specific to hedgehog, since prolactin (lane 10) did not lead to elevated expression of this gene. The panel labelled XAG-1 detects a cement gland-specific gene, and lane 4 shows that hedgehog induces this gene at high level.

Figure 18B:
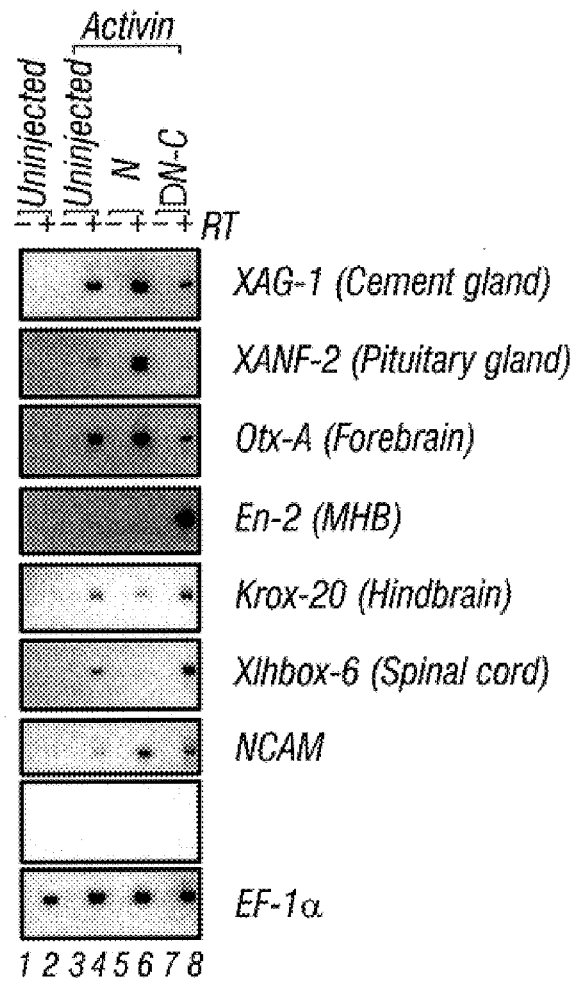

In panel 18B, embryos were injected with N or ΔN–C, and some animal cap explants were treated with activin before culturing until sibling embryos reached tailbud stage. Lanes 1, 2: control animal caps from uninjected embryos. Lanes 3, 4: control animal caps from uninjected embryos, treated with activin. Lanes 5, 6: animal caps from embryos injected with N and treated with activin. Lanes 7, 8: animal caps from embryos injected with ΔN–C and treated with activin. Whereas N displays activities in activin-treated explants similar to those of X-bhh (see B) ΔN–C produces the opposite effect, decreasing anterior and increasing posterior neural marker expression. As shown in FIG. 18B, N behaves like X-bhh in that it induces elevated levels of XANF-2 and Otx-A (lane 6) relative to control activin-treated animal caps (lane 4). Moreover, N also leads to a decrease in the expression of more posterior markers, such as krox-20 and X/Hbox-6, as observed following injection of X-bhh. In contrast to the activity of N (FIG. 4C, lane 6), ΔN–C decreases the expression of the anterior neural genes XANF-2 or Otx-A (FIG. 4C, lane 8) in activin-treated animal caps when compared to uninjected controls (lane 4). Moreover, ΔN–C also leads to an increase in the expression of more posterior markers, such as En-2 and Xlhbox-6.

FIG. 19 shows X-bhh modifies the anteroposterior pattern of neural gene expression in explants under the influence of endogenous neural inducers. (A) Isolation of dorsal explants from injected embryos for the preparation of Keller sandwiches (Keller and Danilchik, 1988; Doniach, et al., 1992; redrawn from Doniach, 1993). (B) Keller sandwiches were made from uninjected (lanes 1 and 2) and X-bhh-injected (lanes 3 and 4) embryos, total RNA was isolated when control embryos reached stage 20, and RT-PCR was used to analyze the expression of XAG-1 and neural markers. XAG-1 is a cement gland marker, XANF-2 is an anterior pituitary marker, Otx-A is a forebrain marker, En-2 demarcates the midbrain-hindbrain boundary, Krox-20 marks rhombomeres 3 and 5 of the hindbrain and XlHbox-6 is a spinal cord marker. N-CAM is a general neural marker whose expression is not restricted along the anteroposterior axis. The EF-1α control demonstrates that a comparable amount of RNA was assayed in each set. Note that expression of XAG-1 and anterior neural markers is stimulated by X-bhh treatment, whereas expression of posterior neural markers is suppressed.

FIG. 20 demonstration of differential activities of N and C domains of hedgehog proteins. As in FIG. 18 above, odd numbered lanes are negative control lanes, and positive numbered lanes show specific gene expression for the markers described above. The N domain of hedgehog is encoded in the construct called Xhh 1208 (lane 8), and the C domain is encoded in the construct called Xhh 1 delta 27–208 (lane 10). The construct Xhh11-1270A (lane 12) is specifically mutated so that it is unable to undergo self-processing. The ability of the N and C domains to induce the genes described above is compared to control blastula cap explants (lane 4), entire embryos as a positive control (lane 2), blastula cap explants expressing a mutated hedgehog as a negative control (lane 14), blastula caps expressing the entire hedgehog 1 (lane 6), and blastula cap explants treated with an independent neural inducer, noggin (lane 16) (discovered by Richard Harland at University of California at Berkeley).

Examining the first panel for the cement gland marker XAG-1 clearly shows that intact hedgehog (lane 6) and the N domain (lane 8) and the processing defective hedgehog (lane 12) are much better than inducing the cement gland than is the C domain (lane 1). Examining the second panel demonstrates that the C domain (lane 10) is better at inducing the pituitary gene XANF1B than is the N domain (lane 8). Since the N domain induces the XAG-1 marker better, described in point A above, the two results together clearly demonstrate that the N and C domains have distinguishable activities. Examination of the remaining panels shows that all described activities of the normal hedgehog (lane 6) can be defined in terms of the activities of the N and C domain.

Examining the third panel, for the forebrain gene otx-A, shows that both the N domain (lane 8) and C domain (lane 10) induce similar levels of this gene, but the processing defective hedgehog (lane 12) is better than either at inducing this gene.

Examining the fourth panel of this figure (NCAM), (as well as the FIG. 18 panels EN-2, krox20, XIHbox6, and NCAM), shows that hedgehog does not induces these more posterior neural genes. Notably, noggin (lane 16) is able to induce pituitary gene and forebrain gene, but it also induces the general neural gene, NCAM, which hedgehog does not. This clearly shows that hedgehog is a distinct activity from the neural inducer noggin, and has a more restricted ability to induce neural genes.

Experiments in the Xenopus embryo were conducted by injecting full-length hedgehog RNA, and immunoprecipitating with a C-domain specific antibody, which proves that full length hedgehog does in fact get processed in vivo in vertebrates, consistent with the data shown in earlier Examples in Drosophila. Thus, the ideas for the utility of detecting hedgehog N and C domains is based on knowledge that such domains do appear through hedgehog processing in vertebrates. Moreover, the knowledge that hedgehog processing does occur in vivo naturally raised the question of whether the resulting N and C domains have independent activity.

The results in FIG. 18 are novel insofar as they establish that the activity of hedgehog in inducing a pituitary gene, and an anterior brain gene, may be enhanced by the TGFβ family of growth factors. This enhancement likely applies to the N and C domains described in FIG. 20, since the genes analyzed are the same. This enhancement is due to hh synergizing with neural inducing factors which are themselves induced by TGF-β family members, including but not limited to such molecules as noggin and follistatin.

The data in FIG. 20 makes several important points. First, the data show that the N and C domains have different though somewhat overlapping activities, and that the N and C activities added together account for all of the observed activity of the intact hedgehog protein. Thus, any clinical or diagnostic uses of hedgehog might be improved by use of the N or C domain, as one generally wishes to use the smallest protein which has an activity for clinical work, as it is less likely to evoke adverse immune responses, or other adverse side effects. Second, the data show that the C domain is better than the N domain in inducing pituitary gene expression and, since it has less induction of cement gland genes that intact hedgehog, or N domain, it suggests that the C domain might be useful in clinical situations where one wishes to enhance the development or expression of the pituitary as specifically as possible. As the pituitary is the source of a number of hormones, any treatment for enhancing pituitary cell growth and activity would ideally have as few side effects as possible, and the C domain is thus a viable candidate for therapies with enhanced pituitary cell growth and function in mind. Third, relating to studies regarding noggin, FIG. 20 shows clearly that while both hedgehog and noggin can induce pituitary gene expression, hedgehog is more specific, since hedgehog does not induce the general neural marker NCAM, whereas noggin induces NCAM as well as pituitary. Fourth, the hedgehog which was mutated to prevent processing (lane 12) is as active as full-length and wild-type hedgehog (lane 6) in inducing pituitary gene expression, but the processing defective hedgehog is better at inducing the forebrain marker otx-A. Thus, for some clinical applications of hedgehog in inducing specific cell types, it is possible that the processing-defective hedgehog will be superior compared to normal hedgehog.

FIG. 21 shows ΔN–C interferes with X-bhh and N activity in animal cap explants. Embryos were injected with various RNAs, animal cap explants were cultured until sibling embryos reached tailbud (stage 25), at which time RT-PCR was used to analyze the expression of the cement gland marker XAG-1 and the control RNA, EF-1α. Lanes 1, 2: control animal caps from uninjected embryos. Lanes 3, 4: animal caps from embryos injected with both X-bhh and prolactin RNAs. Lanes 5, 6: animal caps from embryos injected with box X-bhh and ΔN–C. Lanes 7, 8: animal caps from embryos injected with both N and prolacting RNAs. Lanes 9, 10: animal caps from embryos injected with both N and ΔN–C. The N and X-bhh experiments were conducted independently and thus absolute levels in lanes 3–6 should not be compared to those in lanes 7–10. Note that the induction of XAG-1 expression by X-bhh or N is reduced by co-injection of ΔN–C.

An internal deletion of X-bhh (ΔN–C) blocked the activity of X-bhh and N in explants and reduced dorsoanterior structures in embryos. As elevated hh activity increases the expression of anterior neural genes, and as ΔN–C reduces dorsoanterior structures, these complementary data support a role for hh in neural induction and anteroposterior patterning.

ΔN–C deletes amino acids 28–194 of X-bhh. The primary translation product is predicted to undergo signal sequence cleavage removing amino acids 1–23, and to undergo autoproteolysis. Based on the cleavage site in Drosophila hh (Porter, et al., *Nature*, 374:363, 1995) autoproteolysis would generate a C domain of X-bhh amino acids 198–409, as well as a predicted seven amino acid polypeptide, representing amino acids 24–27, and 195–197 (Lai, et al., *Development* 121:2349, 1995). Analysis of the effect of ΔN–C on neural markers was by standard methods including Northern blot analysis and in situ hybridization (Lai, et al., supra, incorporated herein by reference).

Although ΔN–C does not induce the cement gland marker XAG-1, it decreases the expression of anterior ectodermal and neural markers in activin-treated animal caps. Thus, ΔN–C has the capacity to affect neural patterning. ΔN–C also promotes an increase in posterior neural markers in activin-treated animal caps. Mixing ΔN–C with N or full length X-bhh at a 1:1 ratio led to a dramatic inhibition of the induction of cement gland in animal cap assays, supporting the hypothesis that ΔN–C interfered with X-hh.

EXAMPLE 19

CHOLESTEROL MODIFICATION OF HEDGEHOG POLYPEPTIDE

In addition to peptide bond cleavage, Hh autoprocessing causes the covalent attachment of a lipophilic adduct to the COOH-terminus of Hh-$N_p$ (J. A. Porter et al., *Cell* 86, 21, 1996). This modification is critical for the spatially restricted tissue localization of the Hh signal; in its absence, the signaling domain exerts an inappropriate influence beyond its site of expression (J. A. Porter et al., *Cell* 86, 21, 1996). Physical and biochemical characterization of this lipophilic adduct indicates that it is not the glycosyl phosphatidyl inositol (GPI) anchor, the only other known lipophilic modification associated with secreted cell surface proteins in eukaryotes (S. Udenfriend and K. Kodukula, *A nnu.Rev.Biochem.* 64, 563, 1995; and P. J. Casey, *Science* 268, 221, 1995).

In vitro studies of Hh autoprocessing were performed using a bacterially expressed derivative of the Drosophila protein, $His_6$Hh-C, in which the majority of the $NH_2$-terminal signaling domain and the signal sequence are replaced by a hexa-histidine tag. Cleavage of this protein occurs between residues corresponding to Gly 257 and Cys 258 (J. A. Porter et al., *Nature* 374, 363, 1995) and likely proceeds through a labile thioester intermediate formed by the cysteine thiol and the glycine carbonyl carbon. In the presence of high concentrations of thiols or other small molecules with strongly nucleophilic properties at neutral pH, cleavage of the peptide results from nucleophilic attack upon the thioester carbonyl, causing displacement of the thiol group and formation of an adduct to Gly 257 by the attacking nucleophilic (FIG. 22A). Thus, in reactions with 50 mM dithiothreitol, in vitro cleavage of $His_6$Hh-C proceeded to greater than 50% completion within three hours at 30° C. (FIG. 22B). At 1 mM dithiothreitol, however, the reaction yielded no visible cleavage product (FIG. 22B).

FIG. 22 shows lipid stimulation of Hh autoprocessing in vitro. Panel A illustrates the mechanism of Hh processing. The reaction is initiated by formation of a thioester between the thiol side chain of cysteine 258 and the carbonyl carbon of glycine 257, and N to S shift. This activated intermediate then undergoes a nucleophilic attack by DTT in vitro or by a piophilic nucleophilic in vivo resulting in cleavage as well as a formation of a covalent adduct at the carboxy-terminus of the amino-terminal product, X denotes the attacking nucleophilic. Panel B shows a coomassie blue stained SDS-polyacrylamide gel showing in vitro autocleavage reactions of the bacterially expressed His6Hh-C protein (~29 kD) incubated for 3 hours at 30° C. with no additions (lane 1), 50 mMDTT (lane 2), 1 mMDTT (lane 3), or 1 mMDTT plus bulk S2 cell lipids (lane 4). The Hh-C product of the autoprocessing reaction migrates as an ~25 kD species (lanes 2 and 4); the ~5 kD NH2-terminal product is not resolved in this gel.

The in vivo reaction resulted in lipophilic modification of the $NH_2$-terminal signaling domain. The most direct mechanism by which this could occur, by analogy to the in vitro mechanism (FIG. 22A), would be for a lipid to function as the displacing nucleophilic in attack of the thioester. To explore this possibility, bulk lipids extracted from Drosophila S2 cultured cells (I.Schneider, *J Embryol Exp Morph* 27, 353 (1972); and F. M. Ausubel et al., *Current protocols in molecular biology* (Greene Publishing Associates and Wiley-Interscience, New York, 1995) were added to the in Vitro processing reaction in the presence of 1 mM dithiothreitol. Cleavage was observed and the reaction proceeded to 20% completion in a three hour period (FIG. 22B). The reaction continues beyond this time and reaches ~50% completion by 18 hours.

To identify the components active in the reaction, the bulk S2 lipids were separated into two classes, neutral and complex, by silicic acid column chromatography (W. W. Christie, Lipid analysis (Pergamon, Oxford, ed.2nd, 1982). FIG. 23A is a thin layer chromatography (TLC) plate coated with silica gel G (Merck) showing the fractionation of bulk S2 cell lipids using a heptane:ether:formic acid solvent (80:20:2). Six major spots are visualized by acid charring and are indicated by letters A–F. FIG. 23B is a Coomassie blue-stained SDS-polyacrylamide gel showing in vitro autocleavage reactions of the bacterial expressed $His_6$Hh-C protein incubated with 1 mMDTT plus either unfractionated S2 cell lipids (lane 1), or spots A through F (lanes 2–7, respectively). Addition of lipid spot B but no other resulted in processing of $His_6$Hh-C protein. FIG. 23C is TLC of S2 cell lipids (lane 1) along with selected lipid standards: phosphatidylcholine (lane 2), a diacylglycerol (lane 3), cholesterol (lane 4), stearic acid (lane 5), a triacylglycerol (lane 6), and cholesteryl ester (lane 7). Lipid spot B comigrates with cholesterol, as also demonstrated by mixing radio-labeled cholesterol with S2 lipids before TLC fractionation. FIG. 23D is a Coomassie blue stained SDS-polyacrylamide gel showing that relative to 1 mMDTT alone (lane 1) cholesterol (0.35 mM)+1 mMDTT (lane 2) stimulates $His_2$Hh-C autocleavage in vitro. FIG. 23E is an autoradiogram of electrophoretically-resolved products of $His_6$Hh-C autocleavage reactions driven by 20 mMDTT (lane 1) or 1 mMDTT+0.35 mM cholesterol (lane 2). For lane 1 [$^3$H]cholesterol (3 μCi) was added at the end of the incubation period just prior to electrophoresis; for lane 2[$^3$H]cholesterol was present throughout the incubation period and is incorporated into the amino-terminal product of the reaction. To resolve the ~5 kD product of His6Hh-C autocleavage, reaction products were separated in 17% SDS-polyacrylamide gels.

The activity was found exclusively in the neutral class, so the lipids were subjected to preparative thin layer chromatography (TLC) using a solvent system that resolved neutral lipids (W. W. Christie, *Lipid analysis* (Pergamon, Oxford, ed.2nd, 1982) (FIG. 23A). Lipid spots were visualized with iodine vapor or acid charring, and adsorbent at the corresponding positions of identical uncharred plates was excised and extracted with chloroform/methanol/water. Only lipids extracted from spot B displayed stimulatory activity in the in vitro cleavage reaction (FIG. 23B).

With the use of various lipid standards, it was found that spot B comigrated with cholesterol (FIG. 23C). In addition, the active S2 cell-derived lipid displayed the same mobility as cholesterol in two other solvent systems and gave a positive color test when sprayed with a specific reagent that reacts with sterols; W. W. Christie, *Lipid* analysis (Pergamon, Oxford, ed.2nd, 1982); and R. R. Lowry, *Journal of Lipid Research* 9, 397, 1968). Taken together these results imply that the active lipid component is in the sterol fraction of the S2 lipids. Indeed, it was found that cholesterol, which is the principal sterol in eukaryotic cell membranes (W. W. Christie, *Lipid analysis* (Pergamon, Oxford, ed.2nd, 1982)), displayed stimulatory activity similar to that observed with lipids extracted from spot B when added in pure form to the in vitro processing reaction (FIG. 23D). To establish that the stimulatory activity of cholesterol is a result of its participation as a modifying group, it was shown that $^3$H-labeled cholesterol added to the 1 mM dithiothreitol reaction was incorporated into the $NH_2$-terminal product (FIG. 23E). No incorporation was seen, however, when [$^3$H]cholesterol was added just prior to electrophoresis to a reaction incubated for 3 hours with 20 mM dithiothreitol (FIG. 23E). Also consistent with covalent cholesterol addition, the $NH_2$-terminal fragment of $His_6$Hh-C generated by the cholesterol-driven reaction migrated just beneath the 6 kD marker, whereas the product of the reaction driven by 20 mM dithiothreitol migrated just above this marker (FIG. 24A). Such a shift in mobility, thought to result from an increase capacity for SDS binding to the covalently linked lipid (M. L. Cardoso de Almeida and M. J. Turner, *Nature* 302, 349, 1983),was also noted for Hh-$N_p$ as compared to the precisely truncated $NH_2$-terminal fragment (Hh-N, truncated following Gly 257).

The part of the sterol most likely to act as attacking is the 3β hydroxyl. Such an attack would leave cholesterol as a covalent adduct in ester linkage to the carboxylate of the terminal residue of the NH2-terminal fragment (GLY 257). FIG. 24A shows Coomassie stained gels of $His_6$Hh-C autocleavage reactions carried out in the presence of 20 mMDTT (lane 1), or 1 mMDTT+0.35 mM cholesterol (lanes 2). Lane 3 contains a mixture of the samples loaded in lanes 1 and 2. The amino-terminal product of the cholesterol driven reaction migrates approximately 2 kD faster than the DTT-driven reaction fragment. FIG. 24B is Coomassie stained gels showing protein products of $His_6$Hh-C autocleavage reactions carried out in the presence of 1 mM DTT+0.35 mM cholesterol (lanes 1 and 2) or with 20 mM DTT (lane 3). Prior to loading the gel, samples in lane 2 and 3 were incubated for 60 minutes with 50 mMKOH in 90% methanol (M. C. Field and A. K. Menon, in *Lipid modification of proteins* N. M. Hooper, A. J. Turner, Eds. (Oxford University Press, New York 1992) pp.155). Base treatment causes the cholesterol-driven amino-terminal reaction product to comigrate with the corresponding DTT-driven reaction product. FIG. 24C is an autoradiogram of immunoblotted Hh aminoterminal domains purified from cultured S2 cells. Aminoterminal domains were derived either from a construct truncated after glycine 257 (Hh-N lanes 1,3,4,8, and 9) or from a construct encoding wild-type Hh that produces the amino-terminal domain via the processing reaction (Hh-Np, lane 2,3,5,6,7,8, and 9). Proteins were either directly loaded (lanes 1 and 2) or base-treated (M. C. Field and A. K. Menon, in *Lipid modification of proteins* N. M. Hooper, A. J. Turner, Eds. (Oxford University Press, New York 1992) pp.155) for 5 minutes (lane 5), 20 minutes (lane 6) or 1 hour (lanes 7 and 4) prior to electrophoresis. Lane 3 contains a mixture of the samples loaded in lanes 1 and 2, lane 8 contains a mixture of the samples loaded in lanes 7 and 4, and lane 9 contains a mixture of the samples loaded in lanes 7 and 2. Upon base treatment, Hh-$N_p$ undergoes a shift in mobility from 18.5 kD to 19.5 kD, the mobility of the unmodified Hh-N protein.

Ester bonds are subject to hydrolysis in alkaline conditions and base treatment prior to electrophoresis indeed reduced the migration of the cholesterol-driven reaction product to a position coinciding with that of the dithiothreitol-driven reaction product. These results are consistent with stimulation of the in vitro processing reaction by direct nucleophilic attack of cholesterol on the thioester intermediate to form an ester-linked adduct. If processing of Hh also results in formation of an ester-linked cholesterol adduct in vivo, then the protein-lipid linkage should be subject to base hydrolysis with a concomitant shift in electrophoretic mobility of the protein (normally 18.5 kD). The immunoblot in FIG. 24C shows the base-induced appearance of a species of reduced mobility (19.5 kD), which increased in abundance from ~⅓ of the total after five minutes of treatment to most of the immunoreactive protein after one hour. This novel species comigrated with truncated, unprocessed Hh-N, which is not affected by base treatment. These data are consistent with an ester bond as the protein-lipid linkage in Hh-$N_p$.

To confirm the involvement of cholesterol in formation of the Hh-$N_p$ adduct in vivo, S2 cells containing an inducible wild-type Hh construct were metabolically labeled with [$^3$H]cholesterol. FIG. 25A is an autoradiogram of a gel loaded with total cell proteins from S2 cells containing a stably integrated Cu++-inducible hedgehog gene. Prior to harvesting, these cells were grown in media supplemented with [$^3$H]cholesterol in the absence (lane 1) or presence (lane 2) of 1 mM CuSO4. [$^3$H]cholesterol incorporation is dependent upon Cu++ induction (lane 2) and is restricted to a single protein species migrating at a position corresponding to Hh-$N_P$. FIG. 25B is an HPLC profile of sterols separated on a C18 column by isocratic elution with a solvent containing methanol:ethanol:water (86:10:4) (R. J. Rodriguez and L. W. Parks, *Methods of Enzymology* 111, 37, 1985). ~5 μg of each sterol was mixed, loaded, and elution monitored by absorbance at 210 nM. The structure of cholesterol is shown above cholesterol peak. Other sterols include: 1) 10 desmosterol, which contains one additional double bond between carbon 24 and 25; 2) 20 7-dehydrocholesterol, which contains one additional double bond between carbon 7 and 8; 3) campesterol which contains an additional methyl group on carbon 24; and 4) sitosterol, which contains an additional ethyl group on carbon 24. FIG. 25C shows HPLC analysis as in (B) of the adduct released by base treatment of Hh-$N_p$ metabolically labeled with [$^3$H]cholesterol (A). The radioactive species recovered from the metabolically labeled protein collates with cholesterol. FIG. 25D shows metabolic labeling of vertebrate Sonic hedgehog protein with [$^3$H]cholesterol. Autoradiogram of a gel loaded with total cell proteins from COS-7 cells transferred with a wild-type Sonic hedgehog expression construct (Shh, lane 1) or a construct that generates an unprocessed amino-terminal protein truncated after the conserved glycine at the site of autocleavage (Shh-N, lane 2). The COS-7 cells were incubated in culture medium supplemented with [$^3$H]cholesterol for 24 hours prior to and 36 hours after transfection (COS-7 cells grown at 37° C. in DMEM supplemented with 10% fetal calf serum were plated at ~35% confluence onto two 35 mm dishes in 1 ml of Optimem media (Gibco) containing 1.5% fetal bovine sera and 25 μCi of [$^3$H]cholesterol, giving ~40 μg/ml as the final concentration of cholesterol with a specific activity of 2 Ci/mmol (labeling medium). After 24 hours the labeling medium was removed and the cells were transfected for 6 hours with Shh or Shh-N expression constructs using lipofectamine (Gibco) and serum-free DMEM media. After transfection, 1 ml of fresh labeling medium was added to each dish and the cells were incubated for 36 hours at 37° C. The cells were then harvested without washing, lysed on the plate with Tris buffered saline plus 1% Triton X-100 and the total cell proteins were precipitated with acetone, washed and analyzed as described above for the S2 cell proteins). A strongly labeled species with the Shh but not Shh-N construct. Several other less heavily labeled species are apparent in both lanes, and may represent other cholesterol-modified proteins.

After 48 hours of growth in the presence of [$^{-3}$H] cholesterol, induced and uninduced cultured cells were detergent extracted and total cell proteins were subjected to SDS-PAGE followed by fluorography (Metabolic labeling of S2 cultured cells with [$^{-3}$H]cholesterol was performed essentially as described (Silberkang, et al., *J Biol. Chem.* 258:8503, 1983). Briefly, cells containing a stably integrated Cu++-inducible hedgehog gene were grown at 23° C. for two weeks in Schneider cell media (Gibco) containing a 5% fetal bovine serum depleted of lipoprotein (low cholesterol media,~20 μg/ml cholesterol). These cells were then plated at 40% confluence onto two 35 mm tissue culture dishes (Nunc) in 1 ml of low cholesterol media supplemented with 300 μCi of labeled cholesterol, [1.2.6.7-$^3$H (N)] 65 Ci/mM (NEN) giving a specific activity for cholesterol in this medium of ~5 Ci/mmol. After 24 hours (1 doubling time) one plate of cells was induced to express Hh protein by the addition of $CuSO_4$ (1 mM final concentration). After an additional 24 hours the cells from both dishes were harvested, lysed in Tris buffered saline containing 1% Triton X-100, and total cell protein was precipitated with 5 volumes of cold acetone. The protein pellet was resuspended in 2% SDS in $H_2O$ and reprecipitated with acetone several times to remove unincorporated radioactivity prior to loading onto SDS polyacrylamide gels for analysis. Initial labeling experiments in which 25 μCi of cholesterol was added resulted in ~10 fold decrease in extent of label incorporated into the inducible Hh-$N_p$ protein). Whereas uninduced cells showed no incorporation of [$^3$H]cholesterol into cellular proteins, cells induced to express Hh showed a single strong band with a mobility corresponding to that of Hh-$N_P$ (FIG. 25A). Given the hydrophobic character of Hh-$N_p$, these results suggest that either cholesterol itself or a sterol derivative constitutes the lipophilic adduct of Hh-$N_p$. To determine whether cholesterol is the final form of the adduct, radio-labeled Hh-$N_p$ protein excised from a gel was base-treated to release the adduct, which was then isolated by either extraction (HPLC analysis of the Hh-$N_p$ adduct involved gel isolation of the radioactive band, KOH/methanol treatment of the band to break the ester linkage as described, followed by neutralization of the solution with acetic acid, drying in a speedvac, resuspension in $H_2O$ and extraction of the hydrophobic radioactivity with ether. After evaporation of the ether the sample was resuspended in isopropanol and applied to the C18 column for analysis. Radio-labeled adduct was then subjected to analysis by HPLC with a method specifically designed to resolve various sterols (R. J. Rodriguez and L. W. *Parks, Methods of Enzymology* 111, 37, 1985) (FIG. 25B). The radioactive adduct released from Hh-$N_p$ eluted at the same position as the cholesterol standard, and no radioactivity was detected in any other fraction (FIG. 25C).

The amount of radioactive cholesterol incorporated is consistent with that expected if all of the Hh-$N_p$ synthesized upon induction received a cholesterol adduct (The specific activity of [$^3$H]cholesterol in the S2 cell labeling medium was ~5 Ci/mmol. Assuming after a 24 hour doubling time that this concentration approximately represents that within the S2 cell membrane, then any protein subsequently expressed and receiving cholesterol as an adduct would also be labeled at the same specific activity. As determined by standardized coomassie blue staining, ~50–100 ng or 2.5 to 5 picomoles of Hh-$N_p$ is produced by one 35 mm dish of S2 cells containing the Cu++-inducible Hh construct during 24 hours of induction with 1 mM $CuSO_4$ (13). This predicts ~12.5 to 25 nCi or $2.75 \times 10^4$ to $5.5 \times 10^4$ dpm of radioactivity would be incorporated into Hh-$N_p$ protein produced in our labeling experiment assuming it is cholesterol modified. Total incorporation of radioactivity into Hh-$N_p$ during the in vivo labeling experiment described above was measured at ~$5 \times 10^4$ dpm by excision and scintillation counting of an Hh-$N_p$ gel band), suggesting that other cellular components do not complete effectively as nucleophilic adducts in the in vivo autoprocessing reaction. Also consistent with a homogenous adduct, the mass of cholesterol is consistent with the mass previously measured by mass spectrometry of processed protein purified from cultured cells. A recent MALDI mass spectral analysis gave a mass of ~430 daltons for the Hh-$N_p$ adduct, ~9% larger than the mass of cholesterol (386.6). Detection of this modification required that Hh-$N_p$ be treated with CNBr/70% formic acid, i.e. full length Hh-$N_p$ could not be detected. The mass discrepancy noted above could be accounted for by the net addition of formic acid (45 daltons) during CNBr digestion. This reaction could involve the addition of $H_2O$ across the 5,6 double bond of cholesterol, a common reaction of secondary alkenes in strong acids [R. T. Morrison, R. N. Boyd, *Organic Chemistry* (Allyn and Bacon, Boston, ed.3rd, 1973)], followed by esterification of formate via this newly formed alcohol [B. I. Cohen, G. S. Tint, T. Kuramoto, E. H. Mosbach, *Steroids* 25, 365–378, 1975. To test whether the sterol backbone could be modified by the CNBr treatment, a positively charged cholesterol derivative (3β(N-(N',N'-dimethylamino) ethanecarbamoyl)-cholesterol, Sigma) detectable by MALDI was examined. It was found that incubation of this sterol derivative in 70% formic acid alone resulted in the addition of 45 mass units to the sterol (13), a mass consistent with the net addition of a formic acid molecule). These in vitro and in vivo results show that the Hh-C processing domain functions as a cholesterol transferase; as a result of this activity, a cholesterol adduct is attached via an ester linkage to the COOH-terminus of the $NH_2$-terminal signaling domain of the Hh protein.

To test whether processing of vertebrate hedgehog proteins results in the incorporation of cholesterol as a covalent adduct to the signaling domain, cultured green monkey kidney cells (COS-7) were metabolically labeled with [$^3$H] cholesterol and transfected with expression constructs containing (i) the full length murine Sonic hedgehog (Shh) open reading frame, leading to production of an autocatalytically processed signaling domain (Shh-$N_p$) or (ii) Shh coding sequences precisely truncated at the site of cleavage, thus producing an unprocessed amino terminal signaling domain (Shh-N) (COS-7 cells grown at 37° C. in DMEM supplemented with 10% fetal calf serum were plated at ~35% confluence onto two 35 mm dishes in 1 ml of Optimem media (Gibco) containing 1.5% fetal bovine sera and 25 µCi of [$^3$H]cholesterol, giving ~40 µg/ml as the final concentration of cholesterol with a specific activity of 2 Ci/mmol (labeling medium). After 24 hours the labeling medium was removed and the cells were transfected for 6 hours with Shh or Shh-N expression constructs using lipofectamine (Gibco) and serum-free DMEM media. After transfection, 1 ml of fresh labeling medium was added to each dish and the cells were incubated for 36 hours at 37° C. The cells were then harvested without washing, lysed on the plate with Tris buffered saline plus 1% Triton X-100 and the total cell proteins were precipitated with acetone, washed and analyzed as described above for the S2 cell proteins). Cells expressing the full length construct contained a prominent radio-labeled species migrating at ~19 kD, suggesting that cholesterol is covalently added to Shh-$N_p$ (FIG. 25D). This band was not present in cultures expressing the truncated Shh-N protein (FIG. 25D), indicating that the incorporation of [$^3$H]cholesterol is dependent on the presence of the Shh processing domain. These data strongly suggest that the ability to attach cholesterol as a covalent adduct during autocatalytic processing and cleavage is a universal property of Hh proteins. Several other protein species in addition to the Shh amino terminal domain also appeared to incorporate cholesterol in cells transfected with either construct, suggesting that covalent modification by cholesterol extends to proteins beyond the Hh family. This possibility is consistent with the recently reported occurrence of several sequences homologous to the Hh processing domain in association with amino terminal sequences distinct from hedgehog.

The above disclosure generally describes the present invention. A more complete understanding can be obtained by reference to the following specific examples which are provided herein for purposes of illustration only and are not intended to limit the scope of the invention.

What is claimed is:

1. A method for inducing proliferation or differentiation of non-post mitotic neuronal cells, comprising contacting said neuronal cells with an effective amount of N-terminal fragment of a vertebrate hedgehog polypeptide produced by specific cleavage of a Gly↓Cys Phe cleavage site contained within the vertebrate hedgehog polypeptide and wherein the N-terminal fragment has at the carboxyl terminus a Gly residue and has a molecular weight of about 19 kd by non-reducing SDS-PAGE, wherein said non-post mitotic neuronal cells are derived from floor plate neuronal cells or are motor neurons.

2. The method of claim 1, wherein said vertebrate hedgehog polypeptide is a mammalian hedgehog polypeptide.

3. The method of claim 2, wherein said mammalian hedgehog polypeptide is a human hedgehog polypeptide.

4. A method for inducing proliferation or differentiation of non-post mitotic neuronal cells, comprising contacting said neuronal cells with a C-terminal fragment of a vertebrate hedgehog polypeptide produced by specific cleavage of a Gly↓Cys Phe cleavage site contained within the vertebrate hedgehog polypeptide and wherein the C-terminal fragment has at the amino terminus Cys Phe residues and has a molecular weight of about 25 kd by non-reducing SDS-PAGE, wherein said non-post mitotic neuronal cells are derived from floor plate neuronal cells or are motor neurons.

5. The method of claim 4, wherein said hedgehog polypeptide is a mammalian hedgehog polypeptide.

6. The method of claim 5, wherein said mammalian hedgehog polypeptide is a human hedgehog polypeptide.

7. The method of claim 2 or 4, wherein said hedgehog polypeptide contains an amino acid sequence comprising SEQ ID NO: 21 or SEQ ID NO: 22.

8. The method as in claim 1 or 4 wherein the neuronal cells are vertebrate neuronal cells.

9. The method of claim 8, wherein the vertebrate neuronal cells are human neuronal cells.

10. The method as in claim 1 or 4 wherein the neuronal cells are derived from floor plate neuronal cells.

11. The method of claim 1 or 4, wherein the neuronal cells are motor neurons.

12. The method as in claim 1 or 4 further comprising contacting the cells with a member of the TGF-β family.

13. The method of claim 12, wherein the member of the TGF-β family is activin.

14. The method of claim 1 or 4, further comprising contacting the cells with a neural inducer selected from the group consisting of noggin, follistatin, and a neurotoxin.

* * * * *

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 144 base pairs
      (B) TYPE: nucleic acid
      (C) STRANDEDNESS: both
      (D) TOPOLOGY: both (ii) MOLECULE TYPE: cDNA (ix) FEATURE:
            (A) NAME/KEY: Coding Sequence
            (B) LOCATION: 1...141

(xi) SEQUENCE DESCRIPTION: SEQ ID NO:1:

GTG AAA CTG CGG GTG ACC GAG CCC TGG GAC GAA GAT GGC CAC CAC TCA    48
Val Lys Leu Arg Val Thr Glu Pro Trp Asp Glu Asp Gly His His Ser
 1               5                  10                  15

CAG GAG TCT CTG CAC TAC GAG GGC CGC GCA GTG GAC ATC ACC ACG TCT    96
Gln Glu Ser Leu His Tyr Glu Gly Arg Ala Val Asp Ile Thr Thr Ser
                20                  25                  30

GAC CGC GAC CGC AGC AAG TAC GGC ATG CTG GCC CGC CTG GCG GTG         141
Asp Arg Asp Arg Ser Lys Tyr Gly Met Leu Ala Arg Leu Ala Val
            35                  40                  45

GAG                                                                 144

(2) INFORMATION FOR SEQ ID NO:2:

(i) SEQUENCE CHARACTERISTICS:
            (A) LENGTH: 144 base pairs
            (B) TYPE: nucleic acid
            (C) STRANDEDNESS: both
            (D) TOPOLOGY: both (ii) MOLECULE TYPE: cDNA (ix) FEATURE:
            (A) NAME/KEY: Coding Sequence
            (B) LOCATION: 1...141

(xi) SEQUENCE DESCRIPTION: SEQ ID NO:2:

GTG AAG CTG CGG GTG ACC GAG GGC TGG GAC GAG GAC GGC CAC CAC TCA    48
Val Lys Leu Arg Val Thr Glu Gly Trp Asp Glu Asp Gly His His Ser
 1               5                  10                  15

GAG GAG TCC CTG CAT TAT GAG GGC CGC GCG GTG GAC ATC ACC ACA TCA    96
Glu Glu Ser Leu His Tyr Glu Gly Arg Ala Val Asp Ile Thr Thr Ser
                20                  25                  30

GAC CGC GAC CGC AAT AAG TAT GGA CTG CTG GCG CGC TTG GCA GTG         141
Asp Arg Asp Arg Asn Lys Tyr Gly Leu Leu Ala Arg Leu Ala Val
            35                  40                  45

GAG                                                                 144

(2) INFORMATION FOR SEQ ID NO:3:

(i) SEQUENCE CHARACTERISTICS:
            (A) LENGTH: 14 amino acids
            (B) TYPE: amino acid
            (D) TOPOLOGY: both (ii) MOLECULE TYPE: protein (xi) SEQUENCE DESCRIPTION: SEQ ID NO:3:

Ile Ser Ser His Val His Gly Cys Phe Thr Pro Glu Ser Thr
 1               5                  10

(2) INFORMATION FOR SEQ ID NO:4:

(i) SEQUENCE CHARACTERISTICS:
            (A) LENGTH: 14 amino acids
            (B) TYPE: amino acid
            (D) TOPOLOGY: both (ii) MOLECULE TYPE: protein (xi) SEQUENCE DESCRIPTION: SEQ ID NO:4:

```
Ser Ile Ser His Met His Gly Cys Phe Thr Pro Glu Ser Thr
  1               5                  10
```

(2) INFORMATION FOR SEQ ID NO:5:

(i) SEQUENCE CHARACTERISTICS:
        (A) LENGTH: 14 amino acids
        (B) TYPE: amino acid
        (D) TOPOLOGY: both (ii) MOLECULE TYPE: protein (xi) SEQUENCE DESCRIPTION: SEQ ID NO:5:

```
Val Ala Ala Lys Ser Gly Gly Cys Phe Pro Gly Ser Ala Thr
  1               5                  10
```

(2) INFORMATION FOR SEQ ID NO:6:

(i) SEQUENCE CHARACTERISTICS:
        (A) LENGTH: 14 amino acids
        (B) TYPE: amino acid
        (D) TOPOLOGY: both (ii) MOLECULE TYPE: protein (xi) SEQUENCE DESCRIPTION: SEQ ID NO:6:

```
Val Ala Ala Lys Ser Asp Gly Cys Phe Pro Gly Ser Ala Thr
  1               5                  10
```

(2) INFORMATION FOR SEQ ID NO:7:

(i) SEQUENCE CHARACTERISTICS:
        (A) LENGTH: 14 amino acids
        (B) TYPE: amino acid
        (D) TOPOLOGY: both (ii) MOLECULE TYPE: protein (xi) SEQUENCE DESCRIPTION: SEQ ID NO:7:

```
Val Ala Ala Lys Ser Gly Gly Cys Phe Pro Gly Ser Ala Leu
  1               5                  10
```

(2) INFORMATION FOR SEQ ID NO:8:

(i) SEQUENCE CHARACTERISTICS:
        (A) LENGTH: 14 amino acids
        (B) TYPE: amino acid
        (D) TOPOLOGY: both (ii) MOLECULE TYPE: protein (xi) SEQUENCE DESCRIPTION: SEQ ID NO:8:

```
Val Ala Ala Lys Ser Gly Gly Cys Phe Pro Gly Ser Gly Thr
  1               5                  10
```

(2) INFORMATION FOR SEQ ID NO:9:

(i) SEQUENCE CHARACTERISTICS:
        (A) LENGTH: 15 amino acids
        (B) TYPE: amino acid
        (D) TOPOLOGY: both (ii) MOLECULE TYPE: protein (xi) SEQUENCE DESCRIPTION: SEQ ID NO:9:

```
Val Ala Ala Lys Ser Gly Gly Cys Phe Pro Ala Gly Ala Arg Thr
  1               5                  10                  15
```

(2) INFORMATION FOR SEQ ID NO:10:

(i) SEQUENCE CHARACTERISTICS:
        (A) LENGTH: 14 amino acids
        (B) TYPE: amino acid
        (D) TOPOLOGY: both (ii) MOLECULE TYPE: protein (xi) SEQUENCE DESCRIPTION: SEQ ID NO:10:

Val Ala Ala Lys Thr Gly Gly Cys Phe Pro Ala Gly Ala Gln
 1               5                  10

(2) INFORMATION FOR SEQ ID NO:11:

(i) SEQUENCE CHARACTERISTICS:
        (A) LENGTH: 14 amino acids
        (B) TYPE: amino acid
        (D) TOPOLOGY: both (ii) MOLECULE TYPE: protein (xi) SEQUENCE DESCRIPTION: SEQ ID NO:11:

Val Ala Ala Lys Thr Gly Gly Cys Phe Pro Gly Glu Ala Leu
 1               5                  10

(2) INFORMATION FOR SEQ ID NO:12:

(i) SEQUENCE CHARACTERISTICS:
        (A) LENGTH: 14 amino acids
        (B) TYPE: amino acid
        (D) TOPOLOGY: both (ii) MOLECULE TYPE: protein (xi) SEQUENCE DESCRIPTION: SEQ ID NO:12:

Leu Gly Val Arg Ser Gly Gly Cys Phe Pro Gly Thr Ala Met
 1               5                  10

(2) INFORMATION FOR SEQ ID NO:13:

(i) SEQUENCE CHARACTERISTICS:
        (A) LENGTH: 14 amino acids
        (B) TYPE: amino acid
        (D) TOPOLOGY: both (ii) MOLECULE TYPE: protein (xi) SEQUENCE DESCRIPTION: SEQ ID NO:13:

Leu Ala Val Arg Ala Gly Gly Cys Phe Pro Gly Asn Ala Thr
 1               5                  10

(2) INFORMATION FOR SEQ ID NO:14:

(i) SEQUENCE CHARACTERISTICS:
        (A) LENGTH: 8 amino acids
        (B) TYPE: amino acid
        (D) TOPOLOGY: both (ii) MOLECULE TYPE: protein (xi) SEQUENCE DESCRIPTION: SEQ ID NO:14:

His Gly His Gly Cys Phe Thr Pro
 1               5

(2) INFORMATION FOR SEQ ID NO:15:

(i) SEQUENCE CHARACTERISTICS:
        (A) LENGTH: 8 amino acids

```
            (B) TYPE: amino acid
            (D) TOPOLOGY: both (ii) MOLECULE TYPE: protein (xi) SEQUENCE DESCRIPTION: SEQ ID NO:15:

His Gly His Gly Cys Phe Thr Pro
 1               5

(2) INFORMATION FOR SEQ ID NO:16:

(i) SEQUENCE CHARACTERISTICS:
         (A) LENGTH: 8 amino acids
         (B) TYPE: amino acid
         (D) TOPOLOGY: both (ii) MOLECULE TYPE: protein (xi) SEQUENCE DESCRIPTION: SEQ ID NO:16:

Lys Ser Gly Gly Cys Phe Pro Gly
 1               5

(2) INFORMATION FOR SEQ ID NO:17:

(i) SEQUENCE CHARACTERISTICS:
         (A) LENGTH: 416 amino acids
         (B) TYPE: amino acid
         (D) TOPOLOGY: linear (ii) MOLECULE TYPE: protein (xi) SEQUENCE DESCRIPTION: SEQ ID NO:17:

Met Asp Val Arg Leu His Leu Lys Gln Phe Ala Leu Leu Cys Phe Ile
 1               5                  10                  15

Ser Leu Leu Leu Thr Pro Cys Gly Leu Ala Cys Gly Pro Gly Arg Gly
                20                  25                  30

Tyr Gly Lys Arg Arg His Pro Lys Lys Leu Thr Pro Leu Ala Tyr Lys
            35                  40                  45

Gln Phe Ile Pro Asn Val Ala Glu Lys Thr Leu Gly Ala Ser Gly Lys
        50                  55                  60

Tyr Glu Gly Lys Ile Thr Arg Asn Ser Glu Arg Phe Lys Glu Leu Ile
65                  70                  75                  80

Pro Asn Tyr Asn Pro Asp Ile Ile Phe Lys Asp Glu Glu Asn Thr Asn
                85                  90                  95

Ala Asp Arg Leu Met Thr Lys Arg Cys Lys Asp Lys Leu Asn Ser Leu
            100                 105                 110

Ala Ile Ser Val Met Asn His Trp Pro Gly Val Lys Leu Arg Val Thr
        115                 120                 125

Glu Gly Trp Asp Glu Asp Gly His His Leu Glu Glu Ser Leu His Tyr
130                 135                 140

Glu Gly Arg Ala Val Asp Ile Thr Thr Ser Asp Arg Asp Lys Ser Lys
145                 150                 155                 160

Tyr Gly Met Leu Ser Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Gly Thr Val
        195                 200                 205

Thr Leu Gly Asp Gly Thr Arg Lys Pro Ile Lys Asp Leu Lys Val Gly
        210                 215                 220
```

-continued

```
Asp Arg Val Leu Ala Ala Asp Glu Lys Gly Asn Val Leu Ile Ser Asp
225                 230                 235                 240

Phe Ile Met Phe Ile Asp His Asp Pro Thr Thr Arg Arg Gln Phe Ile
            245                 250                 255

Val Ile Glu Thr Ser Glu Pro Phe Thr Lys Leu Thr Leu Thr Ala Ala
            260                 265                 270

His Leu Val Phe Val Gly Asn Ser Ser Ala Ala Ser Gly Ile Thr Ala
            275                 280                 285

Thr Phe Ala Ser Asn Val Lys Pro Gly Asp Thr Val Leu Val Trp Glu
290                 295                 300

Asp Thr Cys Glu Ser Leu Lys Ser Val Thr Val Lys Arg Ile Tyr Thr
305                 310                 315                 320

Glu Glu His Glu Gly Ser Phe Ala Pro Val Thr Ala His Gly Thr Ile
                325                 330                 335

Ile Val Asp Gln Val Leu Ala Ser Cys Tyr Ala Val Ile Glu Asn His
                340                 345                 350

Lys Trp Ala His Trp Ala Phe Ala Pro Val Arg Leu Cys His Lys Leu
                355                 360                 365

Met Thr Trp Leu Phe Pro Ala Arg Glu Ser Asn Val Asn Phe Gln Glu
370                 375                 380

Asp Gly Ile His Trp Tyr Ser Asn Met Leu Phe His Ile Gly Ser Trp
385                 390                 395                 400

Leu Leu Asp Arg Asp Ser Phe His Pro Leu Gly Ile Leu His Leu Ser
                405                 410                 415
```

(2) INFORMATION FOR SEQ ID NO:18:

(i) SEQUENCE CHARACTERISTICS:
        (A) LENGTH: 418 amino acids
        (B) TYPE: amino acid
        (D) TOPOLOGY: linear (ii) MOLECULE TYPE: protein (xi) SEQUENCE DESCRIPTION: SEQ ID NO:18:

```
Met Arg Leu Leu Thr Arg Val Leu Leu Val Ser Leu Leu Thr Leu Ser
1               5                   10                  15

Leu Val Val Ser Gly Leu Ala Cys Gly Pro Gly Arg Gly Tyr Gly Arg
                20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
        50                  55                  60

Lys Ile Thr Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ser Leu Ala Ile Ser
                100                 105                 110

Val Met Asn His Trp Pro Gly Val Lys Leu Arg Val Thr Glu Gly Trp
                115                 120                 125

Asp Glu Asp Gly His His Phe Glu Glu Ser Leu His Tyr Glu Gly Arg
            130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
```

|          |          |          |          |          |          |          |          |          |          |          |          |
|---|---|---|---|---|---|---|---|---|---|---|---|
|     | 165 |     |     | 170 |     |     |     | 175 |     |     |     |

Ser Lys Ala His Ile His Cys Ser Val Lys Ala Glu Asn Ser Val Ala
            180                 185                 190

Ala Lys Ser Gly Gly Cys Phe Pro Gly Ser Ala Leu Val Ser Leu Gln
        195                 200                 205

Asp Gly Gly Gln Lys Ala Val Lys Asp Leu Asn Pro Gly Asp Lys Val
    210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Val Phe Tyr Val Ile Glu
                245                 250                 255

Thr Gln Glu Pro Val Glu Lys Ile Thr Leu Thr Ala Ala His Leu Leu
            260                 265                 270

Phe Val Leu Asp Asn Ser Thr Glu Asp Leu His Thr Met Thr Ala Ala
                275                 280                 285

Tyr Ala Ser Ser Val Arg Ala Gly Gln Lys Val Met Val Val Asp Asp
    290                 295                 300

Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
                325                 330                 335

Asp Arg Ile Leu Ala Ser Cys Tyr Ala Val Ile Glu Asp Gln Gly Leu
            340                 345                 350

Ala His Leu Ala Phe Ala Pro Ala Arg Leu Tyr Tyr Tyr Val Ser Ser
        355                 360                 365

Phe Leu Phe Pro Gln Asn Ser Ser Ser Arg Ser Asn Ala Thr Leu Gln
370                 375                 380

Gln Glu Gly Val His Trp Tyr Ser Arg Leu Leu Tyr Gln Met Gly Thr
385                 390                 395                 400

Trp Leu Leu Asp Ser Asn Met Leu His Pro Leu Gly Met Ser Val Asn
                405                 410                 415

Ser Ser (2) INFORMATION FOR SEQ ID NO:19:

(i) SEQUENCE CHARACTERISTICS:
        (A) LENGTH: 425 amino acids
        (B) TYPE: amino acid
        (D) TOPOLOGY: both (ii) MOLECULE TYPE: protein (xi) SEQUENCE DESCRIPTION: SEQ ID NO:19:

Met Val Glu Met Leu Leu Leu Thr Arg Ile Leu Leu Val Gly Phe Ile
1               5                   10                  15

Cys Ala Leu Leu Val Ser Ser Gly Leu Thr Cys Gly Pro Gly Arg Gly
            20                  25                  30

Ile Gly His Arg Arg His Pro Lys Lys Leu Thr Pro Leu Ala Tyr Lys
        35                  40                  45

Gln Phe Ile Pro Asn Val Ala Glu Lys Thr Leu Gly Ala Ser Gly Arg
    50                  55                  60

Tyr Glu Gly Lys Ile Thr Arg Asn Ser Glu Arg Phe Lys Glu Leu Ile
65                  70                  75                  80

Pro Asn Tyr Asn Pro Asp Ile Ile Phe Lys Asp Glu Glu Asn Thr Gly
                85                  90                  95

```
Ala Asp Arg Leu Met Thr Cys Arg Cys Lys Asp Lys Leu Asn Ala Leu
            100                 105                 110

Ala Ile Ser Val Met Asn Cys Trp Pro Gly Val Met Leu Arg Val Thr
            115                 120                 125

Glu Gly Trp Asp Glu Asp Gly His His Ser Lys Glu Ser Leu His Tyr
            130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
            165                 170                 175

Tyr Tyr Glu Ser Lys Ala His Ile Cys Ser Val Lys Ala Glu Asn Ser
            180                 185                 190

Val Ala Ala Lys Ser Gly Gly Cys Phe Pro Gly Ser Ala Thr Val His
            195                 200                 205

Leu Glu His Gly Gly Thr Lys Leu Val Lys Asp Leu Ser His Gly Asp
            210                 215                 220

Arg Val Leu Ala Ala Asp Ala Asp Gly Arg Leu Leu Val Ser Asp Phe
225                 230                 235                 240

Leu Leu Thr Phe Leu Asp Arg Met Asp Ser Ser Arg Lys Leu Phe Tyr
            245                 250                 255

Val Ile Glu Thr Arg Gln Pro Arg Ala Arg Leu Leu Leu Thr Ala Ala
            260                 265                 270

His Leu Leu Phe Val Ala Pro Gln His Asn Gln Ser Glu Ala Thr Gly
            275                 280                 285

Ser Thr Ser Gly Gln Ala Leu Phe Ala Ser Asn Val Lys Pro Gly Gln
            290                 295                 300

Pro Val Val Val Leu Gly Glu Gly Gly Gln Gln Leu Leu Pro Ala Ser
305                 310                 315                 320

Val His Ser Val Ser Leu Arg Glu Glu Ala Ser Gly Ala Tyr Ala Pro
            325                 330                 335

Thr Thr Ala Cys Gly Thr Ile Leu Ile Asn Arg Val Leu Ala Ser Cys
            340                 345                 350

Tyr Ala Val Ile Glu Glu His Ser Trp Ala His Ala Ala Phe Ala Pro
            355                 360                 365

His Arg Leu Ala Gln Gly Leu Leu Ala Ala Leu Cys Pro Asp Gly Ala
            370                 375                 380

Ile Pro Thr Ala Ala Thr Thr Thr Gly Ile His Trp Tyr Ser Arg
385                 390                 395                 400

Leu Leu Tyr Arg Ile Gly Ser Trp Val Leu Asp Gly Asp Ala Leu His
            405                 410                 415

Pro Leu Gly Met Val Ala Pro Ala Ser
            420                 425

(2) INFORMATION FOR SEQ ID NO:20:

(i) SEQUENCE CHARACTERISTICS:
        (A) LENGTH: 437 amino acids
        (B) TYPE: amino acid
        (D) TOPOLOGY: linear (ii) MOLECULE TYPE: protein (xi) SEQUENCE DESCRIPTION: SEQ ID NO:20:

Met Leu Leu Leu Leu Ala Arg Cys Phe Leu Val Ile Leu Ala Ser Ser
  1               5                  10                  15

Leu Leu Val Cys Pro Gly Leu Ala Cys Gly Pro Gly Arg Gly Phe Gly
```

-continued

```
                20                      25                      30
Lys Arg Arg His Pro Lys Lys Leu Thr Pro Leu Ala Tyr Lys Gln Phe
            35                      40                  45
Ile Pro Asn Val Ala Glu Lys Thr Leu Gly Ala Ser Gly Arg Tyr Glu
        50                      55                  60
Gly Lys Ile Thr Arg Asn Ser Glu Arg Phe Lys Glu Leu Thr Pro Asn
65                      70                  75                  80
Tyr Asn Pro Asp Ile Ile Phe Lys Asp Glu Asn Thr Gly Ala Asp
                    85                  90                  95
Arg Leu Met Thr Gln Arg Cys Lys Asp Lys Leu Asn Ala Leu Ala Ile
                100                 105                 110
Ser Val Met Asn Gln Trp Pro Gly Val Lys Leu Arg Val Thr Glu Gly
            115                 120                 125
Trp Asp Glu Asp Gly His His Ser Glu Glu Ser Leu His Tyr Glu Gly
        130                 135                 140
Arg Ala Val Asp Ile Thr Thr Ser Asp Arg Asp Arg Ser Lys Tyr Gly
145                 150                 155                 160
Met Leu Ala Arg Leu Ala Val Glu Ala Gly Phe Asp Trp Val Tyr Tyr
                165                 170                 175
Glu Ser Lys Ala His Ile His Cys Ser Val Lys Ala Glu Asn Ser Val
            180                 185                 190
Ala Ala Lys Ser Gly Gly Cys Phe Pro Gly Ser Ala Thr Val His Leu
        195                 200                 205
Glu Gln Gly Gly Thr Lys Leu Val Lys Asp Leu Arg Pro Gly Asp Arg
    210                 215                 220
Val Leu Ala Ala Asp Asp Gln Gly Arg Leu Leu Tyr Ser Asp Phe Leu
225                 230                 235                 240
Thr Phe Leu Asp Arg Asp Glu Gly Ala Lys Lys Val Phe Tyr Val Ile
                245                 250                 255
Glu Thr Leu Glu Pro Arg Glu Arg Leu Leu Leu Thr Ala Ala His Leu
            260                 265                 270
Leu Phe Val Ala Pro His Asn Asp Ser Gly Pro Thr Pro Gly Pro Ser
        275                 280                 285
Ala Leu Phe Ala Ser Arg Val Arg Pro Gly Gln Arg Val Tyr Val Val
    290                 295                 300
Ala Glu Arg Gly Gly Asp Arg Arg Leu Leu Pro Ala Ala Val His Ser
305                 310                 315                 320
Val Thr Leu Arg Glu Glu Ala Gly Ala Tyr Ala Pro Leu Thr Ala
                325                 330                 335
His Gly Thr Ile Leu Ile Asn Arg Val Leu Ala Ser Cys Tyr Ala Val
            340                 345                 350
Ile Glu Glu His Ser Trp Ala His Arg Ala Phe Ala Pro Phe Arg Leu
        355                 360                 365
Ala His Ala Leu Leu Ala Ala Leu Ala Pro Ala Arg Thr Asp Gly Gly
    370                 375                 380
Gly Gly Gly Ser Ile Pro Ala Ala Gln Ser Ala Thr Glu Ala Arg Gly
385                 390                 395                 400
Ala Glu Pro Thr Ala Gly Ile His Trp Tyr Ser Gln Leu Leu Tyr His
                405                 410                 415
Ile Gly Thr Trp Leu Leu Asp Ser Glu Thr Met His Pro Leu Gly Met
            420                 425                 430
Ala Val Lys Ser Ser
            435
```

(2) INFORMATION FOR SEQ ID NO:21:

(i) SEQUENCE CHARACTERISTICS:
        (A) LENGTH: 47 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:21:

```
Val Lys Leu Arg Val Thr Glu Pro Trp Asp Glu Asp Gly His His Ser
 1               5                  10                  15

Gln Glu Ser Leu His Tyr Glu Gly Arg Ala Val Asp Ile Thr Thr Ser
            20                  25                  30

Asp Arg Asp Arg Ser Lys Tyr Gly Met Leu Ala Arg Leu Ala Val
        35                  40                  45
```

(2) INFORMATION FOR SEQ ID NO:22:

(i) SEQUENCE CHARACTERISTICS:
        (A) LENGTH: 47 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:22:

```
Val Lys Leu Arg Val Thr Glu Gly Trp Asp Glu Asp Gly His His Ser
 1               5                  10                  15

Glu Glu Ser Leu His Tyr Glu Gly Arg Ala Val Asp Ile Thr Thr Ser
            20                  25                  30

Asp Arg Asp Arg Asn Lys Tyr Gly Leu Leu Ala Arg Leu Ala Val
        35                  40                  45
```

(2) INFORMATION FOR SEQ ID NO:23:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:23:

```
Leu Thr Val Thr Pro Ala His
 1               5
```

(2) INFORMATION FOR SEQ ID NO:24:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:24:

```
Leu Leu Leu Thr Ala Ala His
 1               5
```

(2) INFORMATION FOR SEQ ID NO:25:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:25:

Leu Leu Leu Thr Pro Trp His
  1               5

(2) INFORMATION FOR SEQ ID NO:26:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:26:

Leu Ala Leu Thr Pro Ala His
  1               5

(2) INFORMATION FOR SEQ ID NO:27:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:27:

Trp Val Val Thr Ala Ala His
  1               5

(2) INFORMATION FOR SEQ ID NO:28:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:28:

Trp Val Val Ser Ala Ala His
  1               5

(2) INFORMATION FOR SEQ ID NO:29:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:29:

Trp Val Met Thr Ala Ala His
  1               5

(2) INFORMATION FOR SEQ ID NO:30:

(i) SEQUENCE CHARACTERISTICS:
            (A) LENGTH: 7 amino acids
            (B) TYPE: amino acid (D) TOPOLOGY: linear (ii) MOLECULE TYPE: peptide (xi) SEQUENCE DESCRIPTION: SEQ ID NO:30:

Trp Val Ile Ser Ala Thr His
 1               5

(2) INFORMATION FOR SEQ ID NO:31:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:31:

Trp Ile Leu Thr Ala Ala His
 1               5

(2) INFORMATION FOR SEQ ID NO:32:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:32:

Trp Val Leu Thr Ala Ala His
 1               5

(2) INFORMATION FOR SEQ ID NO:33:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:33:

Phe Val Leu Thr Ala Ala His
 1               5

(2) INFORMATION FOR SEQ ID NO:34:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:34:

Tyr Val Leu Thr Ala Ala His
 1               5

(2) INFORMATION FOR SEQ ID NO:35:

(i) SEQUENCE CHARACTERISTICS:
        (A) LENGTH: 7 amino acids
        (B) TYPE: amino acid
        (D) TOPOLOGY: linear (ii) MOLECULE TYPE: peptide -continued

```
    (xi) SEQUENCE DESCRIPTION: SEQ ID NO:35:

Trp Ile Leu Ser Ala Ala His
 1               5

(2) INFORMATION FOR SEQ ID NO:36:

(i) SEQUENCE CHARACTERISTICS:
         (A) LENGTH: 8 amino acids
         (B) TYPE: amino acid
         (D) TOPOLOGY: linear (ii) MOLECULE TYPE: peptide (ix) FEATURE:
         (B) LOCATION: 1...1
         (D) OTHER INFORMATION: where Xaa at position 1 is any amino
             acid
         (B) LOCATION: 3...4
         (D) OTHER INFORMATION: where Xaa at positions 3-4 is any amino
             acid
         (B) LOCATION: 7...8
         (D) OTHER INFORMATION: where Xaa at positions 7-8 is any amino
             acid (xi) SEQUENCE DESCRIPTION: SEQ ID NO:36:

Xaa Thr Xaa Xaa His Leu Xaa Xaa
 1               5

(2) INFORMATION FOR SEQ ID NO:37:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (xi) SEQUENCE DESCRIPTION: SEQ ID NO:37:

Leu Gly Val Arg Ser Gly Gly Cys Phe Pro Gly Thr Ala Met
 1               5                  10
```